(12) United States Patent
Jacobson et al.

(10) Patent No.: US 9,217,144 B2
(45) Date of Patent: Dec. 22, 2015

(54) ASSEMBLY OF HIGH FIDELITY POLYNUCLEOTIDES

(75) Inventors: Joseph Jacobson, Newton, MA (US); Larry Li-Yang Chu, Brighton, MA (US)

(73) Assignee: Gen9, Inc., Cambridge, MA (US)

( * ) Notice: Subject to any disclaimer, the term of this patent is extended or adjusted under 35 U.S.C. 154(b) by 0 days.

(21) Appl. No.: 13/520,383

(22) PCT Filed: Jan. 6, 2011

(86) PCT No.: PCT/US2011/020335
§ 371 (c)(1),
(2), (4) Date: Oct. 1, 2012

(87) PCT Pub. No.: WO2011/085075
PCT Pub. Date: Jul. 14, 2011

(65) Prior Publication Data
US 2013/0059761 A1 Mar. 7, 2013

Related U.S. Application Data

(60) Provisional application No. 61/293,192, filed on Jan. 7, 2010, provisional application No. 61/310,076, filed on Mar. 3, 2010, provisional application No. 61/334,416, filed on May 13, 2010.

(51) Int. Cl.
*C12Q 1/68* (2006.01)
*C12N 15/10* (2006.01)

(52) U.S. Cl.
CPC .......... *C12N 15/1031* (2013.01); *C12Q 1/6811* (2013.01); *C12Q 1/6837* (2013.01)

(58) Field of Classification Search
CPC ........... C12Q 1/6811; C12Q 2525/301; C12Q 2565/525; C12Q 1/6837; C12N 15/1031
USPC .................................................. 435/91.2, 6.1
See application file for complete search history.

(56) References Cited

U.S. PATENT DOCUMENTS

| | | |
|---|---|---|
| 4,500,707 A | 2/1985 | Caruthers et al. |
| 4,683,195 A | 7/1987 | Mullis |
| 4,683,202 A | 7/1987 | Mullis |
| 4,689,405 A | 8/1987 | Frank |
| 4,725,677 A | 2/1988 | Koster et al. |
| 4,800,159 A | 1/1989 | Mullis |
| 4,965,188 A | 10/1990 | Mullis |
| 4,999,294 A | 3/1991 | Looney |
| 5,047,524 A | 9/1991 | Andrus et al. |
| 5,104,789 A | 4/1992 | Permar |
| 5,104,792 A | 4/1992 | Silver |
| 5,132,215 A | 7/1992 | Jayaraman |
| 5,143,854 A | 9/1992 | Pirrung et al. |
| 5,288,514 A | 2/1994 | Ellman |
| 5,356,802 A | 10/1994 | Chandrasegaran |
| 5,384,261 A | 1/1995 | Winkler et al. |
| 5,405,783 A | 4/1995 | Pirrung |
| 5,424,186 A | 6/1995 | Fodor |
| 5,436,150 A | 7/1995 | Chandrasegaran |
| 5,436,327 A | 7/1995 | Southern |
| 5,445,934 A | 8/1995 | Fodor |
| 5,459,039 A | 10/1995 | Modrich |
| 5,474,796 A | 12/1995 | Brennan |
| 5,498,531 A | 3/1996 | Jarrell |
| 5,508,169 A | 4/1996 | Deugau |
| 5,510,270 A | 4/1996 | Fodor et al. |
| 5,512,463 A | 4/1996 | Stemmer |
| 5,514,789 A | 5/1996 | Kempe |
| 5,527,681 A | 6/1996 | Holmes |
| 5,541,061 A | 7/1996 | Fodor |
| 5,605,793 A | 2/1997 | Stemmer |
| 5,624,711 A | 4/1997 | Sundberg |
| 5,639,603 A | 6/1997 | Dower et al. |
| 5,641,658 A | 6/1997 | Adams |
| 5,653,939 A | 8/1997 | Hollis |
| 5,674,742 A | 10/1997 | Northrup |
| 5,679,522 A | 10/1997 | Modrich |
| 5,695,940 A | 12/1997 | Drmanac |
| 5,700,637 A | 12/1997 | Southern |
| 5,700,642 A | 12/1997 | Monforte et al. |

(Continued)

FOREIGN PATENT DOCUMENTS

| | | |
|---|---|---|
| EP | 0259160 | 3/1988 |
| EP | 1015576 | 3/1999 |

(Continued)

OTHER PUBLICATIONS

Gu et al., Analysts, vol. 135, No. 3, pp. 441-451, published online Dec. 2009.*
Duggan et al. (1999) "Microarrays: Making Them and Using Them in Microarray Bioinformatics", Nat. Genet. S21:10 ; Cambridge University Press, 2003.
Golz and Kemper, "Enzymatic mutation detection: enrichment of heteroduplexes from hybrid DNA mixtures by cleavage-deficient GST-tagged endonuclease VII" Nucleic Acids Research, 27(15):e7 (1999).
McGall et al. (1996) "Light-directed synthesis of high-density oligonucleotide arrays using semiconductor photoresists", Proc. Natl. Acad. Sci. U.S.A. 93:13555.
Markham, N. R. & Zuker, M. (2005) DINAMelt web server for nucleic acid melting prediction. *Nucleic Acids Res.*, 33, W577-W581.
Oleykowski CA et al. (1998), "Mutation detection using a novel plant endonuclease." Nucleic Acids Res. 26: 4596-4602.
Zielke and Szymczyk (2009), "Experimental investigation of the motion and deformation of droplets on surfaces with a linear wettability gradient "Eur. Phys. J. Special Topics, 166, 155-158.
Blanchard, A.(1998) "Synthetic DNA Arrays" In Genetic Engineering, vol. 20:111-123, Plenum Press.
Kong D. et al. "Parallel gene synthesis in a microfluidic device" Nucleic Acids Research, vol. 35, No. 8, pp. E61-1, 2007.
Zhou X. et al. "Microfluidic PicoArray synthesis of oligodeoxynucleotides and simultaneous assembling of multiple DNA sequences" , Nucleic Acids Research, vol. 32, No. 18, pp. 5409-5417, 2004.

(Continued)

*Primary Examiner* — Cynthia B Wilder
(74) *Attorney, Agent, or Firm* — Greenberg Traurig, LLP; Natalie Salem; Fang Xie

(57) ABSTRACT

Methods and apparatus relate to the synthesis of high fidelity polynucleotides and to the reduction of sequence errors generated during synthesis of nucleic acids on a solid support. Specifically, design of support-bound template oligonucleotides is disclosed. Assembly methods include cycles of annealing, stringent wash and extension of polynucleotides comprising a sequence region complementary to immobilized template oligonucleotides. The error free synthetic nucleic acids generated therefrom can be used for a variety of applications, including synthesis of biofuels and value-added pharmaceutical products.

25 Claims, 18 Drawing Sheets

(56) References Cited

U.S. PATENT DOCUMENTS

| | | |
|---|---|---|
| 5,702,894 A | 12/1997 | Modrich |
| 5,738,829 A | 4/1998 | Kempe |
| 5,739,386 A | 4/1998 | Holmes |
| 5,750,335 A | 5/1998 | Gifford |
| 5,766,550 A | 6/1998 | Kaplan et al. |
| 5,770,358 A | 6/1998 | Dower et al. |
| 5,780,272 A | 7/1998 | Jarrell |
| 5,795,714 A | 8/1998 | Cantor |
| 5,830,655 A | 11/1998 | Monforte |
| 5,830,721 A | 11/1998 | Stemmer |
| 5,834,252 A | 11/1998 | Stemmer |
| 5,858,754 A | 1/1999 | Modrich |
| 5,861,482 A | 1/1999 | Modrich |
| 5,871,902 A | 2/1999 | Weininger |
| 5,877,280 A | 3/1999 | Wetmur |
| 5,916,794 A | 6/1999 | Chandrasegaran |
| 5,922,539 A | 7/1999 | Modrich et al. |
| 5,928,905 A | 7/1999 | Stemmer |
| 5,929,208 A | 7/1999 | Heller |
| 5,942,609 A | 8/1999 | Hunkapiller |
| 5,953,469 A | 9/1999 | Zhou |
| 6,008,031 A | 12/1999 | Modrich et al. |
| 6,013,440 A | 1/2000 | Lipshutz |
| 6,017,696 A | 1/2000 | Heller |
| 6,042,211 A | 3/2000 | Hudson et al. |
| 6,093,302 A | 7/2000 | Montgomery |
| 6,103,463 A | 8/2000 | Chetverin |
| 6,136,568 A | 10/2000 | Hiatt |
| 6,150,102 A | 11/2000 | Mills |
| 6,150,141 A | 11/2000 | Jarrell |
| 6,165,793 A | 12/2000 | Stemmer |
| 6,177,558 B1 | 1/2001 | Brennan et al. |
| 6,242,211 B1 | 6/2001 | Peterson |
| 6,248,521 B1 | 6/2001 | Van Ness et al. |
| 6,261,797 B1 | 7/2001 | Sorge |
| 6,271,957 B1 | 8/2001 | Quate |
| 6,277,632 B1 | 8/2001 | Harney |
| 6,280,595 B1 | 8/2001 | Montgomery |
| 6,284,463 B1 | 9/2001 | Hasebe |
| 6,287,825 B1 | 9/2001 | Weissman |
| 6,287,861 B1 | 9/2001 | Stemmer |
| 6,291,242 B1 | 9/2001 | Stemmer |
| 6,315,958 B1 | 11/2001 | Singh-Gasson |
| 6,322,971 B1 | 11/2001 | Chetverin |
| 6,333,153 B1 | 12/2001 | Fishel |
| 6,346,399 B1 | 2/2002 | Weissman |
| 6,358,712 B1 | 3/2002 | Jarrell |
| 6,365,355 B1 | 4/2002 | McCutchen-Maloney |
| 6,372,434 B1 | 4/2002 | Weissman |
| 6,372,484 B1 | 4/2002 | Ronchi |
| 6,375,903 B1 | 4/2002 | Cerrina et al. |
| 6,406,847 B1 | 6/2002 | Cox |
| 6,410,220 B1 | 6/2002 | Hodgson et al. |
| 6,416,164 B1 | 7/2002 | Stearns et al. |
| 6,426,184 B1 | 7/2002 | Gao |
| 6,444,111 B1 | 9/2002 | Montgomery |
| 6,444,175 B1 | 9/2002 | Singh-Gasson |
| 6,479,652 B1 | 11/2002 | Crameri |
| 6,480,324 B2 | 11/2002 | Quate |
| 6,489,146 B2 | 12/2002 | Stemmer |
| 6,495,318 B2 | 12/2002 | Harney |
| 6,506,603 B1 | 1/2003 | Stemmer |
| 6,511,849 B1 | 1/2003 | Wang |
| 6,514,704 B2 | 2/2003 | Bruce et al. |
| 6,521,427 B1 | 2/2003 | Evans |
| 6,534,271 B2 | 3/2003 | Furste |
| 6,537,776 B1 | 3/2003 | Short |
| 6,565,727 B1 | 5/2003 | Shenderov et al. |
| 6,586,211 B1 | 7/2003 | Stahler et al. |
| 6,596,239 B2 | 7/2003 | Williams et al. |
| 6,605,451 B1 | 8/2003 | Marmaro |
| 6,610,499 B1 | 8/2003 | Fulwyler et al. |
| 6,613,581 B1 | 9/2003 | Wada |
| 6,632,641 B1 | 10/2003 | Brennan |
| 6,650,822 B1 | 11/2003 | Zhou |
| 6,658,802 B2 | 12/2003 | Lucas, Jr. et al. |
| 6,664,112 B2 | 12/2003 | Mulligan |
| 6,664,388 B2 | 12/2003 | Nelson |
| 6,670,127 B2 | 12/2003 | Evans |
| 6,670,605 B1 | 12/2003 | Storm |
| 6,800,439 B1 | 10/2004 | Mcgall et al. |
| 6,802,593 B2 | 10/2004 | Ellson et al. |
| 6,824,866 B1 | 11/2004 | Glazer et al. |
| 6,830,890 B2 | 12/2004 | Lockhart et al. |
| 6,833,450 B1 | 12/2004 | Mcgall et al. |
| 6,846,655 B1 | 1/2005 | Wagner et al. |
| 6,897,025 B2 | 5/2005 | Cox |
| 6,911,132 B2 | 6/2005 | Pamula et al. |
| 6,921,818 B2 | 7/2005 | Sproat |
| 6,932,097 B2 | 8/2005 | Ellson et al. |
| 6,969,587 B2 | 11/2005 | Taylor |
| 6,969,847 B2 | 11/2005 | Davis |
| 7,090,333 B2 | 8/2006 | Mutz et al. |
| 7,133,782 B2 | 11/2006 | Odedra |
| 7,169,560 B2 | 1/2007 | Lapidus et al. |
| 7,179,423 B2 | 2/2007 | Bohm |
| 7,183,406 B2 | 2/2007 | Belshaw et al. |
| 7,262,031 B2 | 8/2007 | Lathrop et al. |
| 7,273,730 B2 | 9/2007 | Du Breuil Lastrucci |
| 7,303,320 B1 | 12/2007 | Ashley |
| 7,303,872 B2 | 12/2007 | Sussman |
| 7,323,320 B2 | 1/2008 | Oleinikov |
| 7,399,590 B2 | 7/2008 | Piepenburg |
| 7,432,055 B2 | 10/2008 | Pemov |
| 7,498,176 B2 | 3/2009 | McCormick et al. |
| 7,563,600 B2 | 7/2009 | Oleinikov |
| 7,820,412 B2 | 10/2010 | Belshaw |
| 7,879,580 B2 | 2/2011 | Carr |
| 8,053,191 B2 | 11/2011 | Blake |
| 8,058,004 B2 | 11/2011 | Oleinikov |
| 8,173,368 B2 | 5/2012 | Staehler |
| 8,716,467 B2 | 5/2014 | Jacobson |
| 8,808,986 B2 | 8/2014 | Jacobson |
| 9,023,601 B2 | 5/2015 | Oleinikov |
| 9,051,666 B2 | 6/2015 | Oleinikov |
| 2001/0012537 A1 | 8/2001 | Anderson et al. |
| 2001/0031483 A1 | 10/2001 | Sorge |
| 2001/0049125 A1 | 12/2001 | Stemmer |
| 2002/0012616 A1 | 1/2002 | Zhou |
| 2002/0037579 A1 | 3/2002 | Ellson et al. |
| 2002/0058275 A1 | 5/2002 | Fishel |
| 2002/0081582 A1 | 6/2002 | Gao et al. |
| 2002/0127552 A1 | 9/2002 | Church |
| 2002/0132259 A1 | 9/2002 | Wagner |
| 2002/0132308 A1 | 9/2002 | Liu |
| 2002/0133359 A1 | 9/2002 | Brown |
| 2003/0017552 A1 | 1/2003 | Jarrell |
| 2003/0044980 A1 | 3/2003 | Mancebo |
| 2003/0047688 A1 | 3/2003 | Faris |
| 2003/0050437 A1 | 3/2003 | Montgomery |
| 2003/0050438 A1 | 3/2003 | Montgomery |
| 2003/0054390 A1 | 3/2003 | Crameri |
| 2003/0068633 A1 | 4/2003 | Belshaw et al. |
| 2003/0068643 A1 | 4/2003 | Brennan |
| 2003/0082630 A1 | 5/2003 | Kolkman |
| 2003/0087298 A1 | 5/2003 | Green |
| 2003/0091476 A1 | 5/2003 | Zhou |
| 2003/0099952 A1 | 5/2003 | Green |
| 2003/0118485 A1 | 6/2003 | Singh-Gasson |
| 2003/0118486 A1 | 6/2003 | Zhou |
| 2003/0120035 A1 | 6/2003 | Gao |
| 2003/0134807 A1 | 7/2003 | Hardin |
| 2003/0143550 A1 | 7/2003 | Green |
| 2003/0143724 A1 | 7/2003 | Cerrina |
| 2003/0170616 A1 | 9/2003 | Wang |
| 2003/0171325 A1 | 9/2003 | Gascoyne et al. |
| 2003/0175907 A1 | 9/2003 | Frazer |
| 2003/0186226 A1 | 10/2003 | Brennan et al. |
| 2003/0198948 A1 | 10/2003 | Stahler |
| 2003/0215837 A1 | 11/2003 | Frey |
| 2003/0215855 A1 | 11/2003 | Dubrow |
| 2003/0215856 A1 | 11/2003 | Church |
| 2004/0002103 A1 | 1/2004 | Short |
| 2004/0005673 A1 | 1/2004 | Jarrell |

(56) References Cited

U.S. PATENT DOCUMENTS

| | | | |
|---|---|---|---|
| 2004/0009479 A1 | 1/2004 | Wohlgemuth et al. |
| 2004/0009520 A1 | 1/2004 | Albert |
| 2004/0014083 A1 | 1/2004 | Yuan |
| 2004/0101444 A1 | 5/2004 | Sommers |
| 2004/0101894 A1 | 5/2004 | Albert et al. |
| 2004/0101949 A1 | 5/2004 | Green |
| 2004/0106728 A1 | 6/2004 | McGall et al. |
| 2004/0110211 A1 | 6/2004 | McCormick |
| 2004/0110212 A1 | 6/2004 | McCormick |
| 2004/0126757 A1 | 7/2004 | Cerrina |
| 2004/0132029 A1 | 7/2004 | Sussman |
| 2004/0166567 A1 | 8/2004 | Santi |
| 2004/0171047 A1 | 9/2004 | Dahl et al. |
| 2004/0185484 A1 | 9/2004 | Costa et al. |
| 2004/0241655 A1 | 12/2004 | Hwang |
| 2004/0259146 A1 | 12/2004 | Friend |
| 2005/0053997 A1 | 3/2005 | Evans |
| 2005/0069928 A1 | 3/2005 | Nelson |
| 2005/0079510 A1 | 4/2005 | Berka et al. |
| 2005/0106606 A1 | 5/2005 | Parker |
| 2005/0118628 A1 | 6/2005 | Evans |
| 2005/0202429 A1 | 9/2005 | Trau et al. |
| 2005/0227235 A1 | 10/2005 | Carr |
| 2005/0255477 A1 | 11/2005 | Carr |
| 2006/0008833 A1 | 1/2006 | Jacobson |
| 2006/0040297 A1 | 2/2006 | Leamon et al. |
| 2006/0054503 A1 | 3/2006 | Pamula et al. |
| 2006/0127920 A1 | 6/2006 | Church |
| 2006/0127926 A1 | 6/2006 | Belshaw et al. |
| 2006/0134638 A1 | 6/2006 | Mulligan et al. |
| 2006/0160138 A1 | 7/2006 | Church |
| 2006/0194214 A1 | 8/2006 | Church |
| 2007/0004041 A1 | 1/2007 | Church et al. |
| 2007/0122817 A1 | 5/2007 | Church et al. |
| 2007/0231805 A1 | 10/2007 | Baynes |
| 2007/0281309 A1 | 12/2007 | Kong et al. |
| 2008/0009420 A1 | 1/2008 | Schroth |
| 2008/0014589 A1* | 1/2008 | Link et al. ............ 435/6 |
| 2008/0105829 A1 | 5/2008 | Faris |
| 2008/0274513 A1 | 11/2008 | Shenderov et al. |
| 2008/0300842 A1 | 12/2008 | Govindarajan |
| 2009/0016932 A1 | 1/2009 | Curcio |
| 2009/0878840 | 4/2009 | Baynes et al. |
| 2009/0137408 A1 | 5/2009 | Jacobson |
| 2009/0311713 A1* | 12/2009 | Pollack et al. ............ 435/6 |
| 2010/0015614 A1 | 1/2010 | Beer et al. |
| 2010/0015668 A1 | 1/2010 | Staehler et al. |
| 2010/0016178 A1 | 1/2010 | Sussman et al. |
| 2011/0008775 A1* | 1/2011 | Gao et al. ............ 435/6 |
| 2011/0117625 A1 | 5/2011 | Lippow et al. |
| 2012/0028843 A1 | 2/2012 | Ramu |
| 2012/0220497 A1 | 8/2012 | Jacobson |
| 2012/0270754 A1 | 10/2012 | Blake |
| 2012/0283110 A1 | 11/2012 | Shendure |
| 2012/0283140 A1 | 11/2012 | Chu |
| 2012/0315670 A1 | 12/2012 | Jacobson |
| 2012/0322681 A1 | 12/2012 | Kung |
| 2013/0059296 A1 | 3/2013 | Jacobson et al. |
| 2013/0059761 A1 | 3/2013 | Jacobson |
| 2013/0244884 A1 | 9/2013 | Jacobson |
| 2013/0252849 A1 | 9/2013 | Hudson |
| 2013/0281308 A1 | 10/2013 | Jacobson |
| 2013/0296192 A1 | 11/2013 | Jacobson |
| 2013/0296194 A1 | 11/2013 | Jacobson |
| 2013/0309725 A1 | 11/2013 | Jacobson |
| 2014/0141982 A1 | 5/2014 | Jacobson |
| 2014/0309119 A1 | 10/2014 | Jacobson |
| 2015/0065393 A1 | 3/2015 | Jacobson |
| 2015/0159204 A1* | 6/2015 | Drmanac ............ C12Q 1/682 506/16 |

FOREIGN PATENT DOCUMENTS

| | | |
|---|---|---|
| EP | 1159285 | 9/2000 |
| EP | 1180548 | 2/2002 |
| EP | 1205548 | 5/2002 |
| WO | WO90/00626 | 1/1990 |
| WO | WO93/17126 | 9/1993 |
| WO | WO93/20092 | 10/1993 |
| WO | WO94/18226 | 8/1994 |
| WO | WO97/35957 | 10/1997 |
| WO | WO98/05765 | 2/1998 |
| WO | WO98/20020 | 5/1998 |
| WO | WO98/38326 | 9/1998 |
| WO | WO99/19341 | 4/1999 |
| WO | WO99/25724 | 5/1999 |
| WO | WO 99/42813 | 8/1999 |
| WO | WO00/29616 | 5/2000 |
| WO | WO00/40715 | 7/2000 |
| WO | WO 00/46386 | 8/2000 |
| WO | WO00/49142 | 8/2000 |
| WO | WO01/88173 | 11/2001 |
| WO | WO02/04597 | 1/2002 |
| WO | WO 02/24597 | 3/2002 |
| WO | WO02/081490 | 10/2002 |
| WO | WO02/095073 | 11/2002 |
| WO | WO02/101004 | 12/2002 |
| WO | WO03/010311 | 2/2003 |
| WO | WO03/033718 | 4/2003 |
| WO | WO 03/040410 | 5/2003 |
| WO | WO 03/046223 | 5/2003 |
| WO | WO03/054232 | 7/2003 |
| WO | WO03/060084 | 7/2003 |
| WO | WO03/064611 | 7/2003 |
| WO | WO 03/064026 | 8/2003 |
| WO | WO 03/064027 | 8/2003 |
| WO | WO 03/064699 | 8/2003 |
| WO | WO 03/065038 | 8/2003 |
| WO | WO 03/066212 | 8/2003 |
| WO | WO 03/100012 | 12/2003 |
| WO | WO2004/002627 | 1/2004 |
| WO | WO2004/024886 | 3/2004 |
| WO | WO 2004/029586 | 4/2004 |
| WO | WO 2004/031351 | 4/2004 |
| WO | WO 2004/031399 | 4/2004 |
| WO | WO2004/034028 | 4/2004 |
| WO | WO2004/090170 | 10/2004 |
| WO | WO2005059096 | 6/2005 |
| WO | WO2005/071077 | 8/2005 |
| WO | WO2005/089110 | 9/2005 |
| WO | WO 2005/107939 | 11/2005 |
| WO | WO2005/123956 | 12/2005 |
| WO | WO2006/044956 | 4/2006 |
| WO | WO2006/049843 | 5/2006 |
| WO | WO2006/076679 | 7/2006 |
| WO | WO2006/127423 | 11/2006 |
| WO | WO2007/008951 | 1/2007 |
| WO | WO2007/009082 | 1/2007 |
| WO | WO2007/075438 | 7/2007 |
| WO | WO2007/087347 | 8/2007 |
| WO | WO2007/113688 | 10/2007 |
| WO | WO2007/117396 | 10/2007 |
| WO | WO2007/120624 | 10/2007 |
| WO | WO2007/123742 | 11/2007 |
| WO | WO 2007/136736 | 11/2007 |
| WO | WO2007/136833 | 11/2007 |
| WO | WO2007/136834 | 11/2007 |
| WO | WO2007/136835 | 11/2007 |
| WO | WO2007/136840 | 11/2007 |
| WO | WO2008/024319 | 2/2008 |
| WO | WO2008/045380 | 4/2008 |
| WO | WO2008/054543 | 5/2008 |
| WO | WO2008/076368 | 6/2008 |
| WO | WO2008/130629 | 10/2008 |
| WO | WO2010/025310 | 3/2010 |
| WO | WO2010/025310 | 7/2010 |
| WO | WO2011/066185 | 6/2011 |
| WO | WO 2011/066186 | 6/2011 |
| WO | WO2011/066186 | 6/2011 |
| WO | WO2011/085075 | 7/2011 |

(56) References Cited

FOREIGN PATENT DOCUMENTS

| WO | WO 2011/056872 | 11/2011 |
|---|---|---|
| WO | WO 2012/064975 | 5/2012 |
| WO | WO 2012/174337 | 12/2012 |
| WO | WO 2013/032850 | 4/2013 |
| WO | WO 2013/163263 | 10/2013 |
| WO | WO 2014/004393 | 1/2014 |
| WO | WO 2014/151696 | 9/2014 |
| WO | WO 2014/160004 | 10/2014 |
| WO | WO 2014/160059 | 10/2014 |

OTHER PUBLICATIONS

Gulati S. et al. "Opportunities for microfluidic technologies in synthetic biology" Journal of the Royal Society, vol. 6, Suppl. 4, pp. S493-S506, 2009.
International Search Report for International Patent Application PCT/US2011/020335 mailed on Jul. 19, 2011.
Adessi et al., "Solid phase DNA amplification: characterisation of primer attachment and amplification mechanisms," Nucleic Acids Research, 28(20):E87, (Oct. 15, 2000).
Afshari et al. "Application of Complementary DNA Microarray Technology to Carcinogen Identification, Toxicology, and Drug Safety". Cancer Research, 59, 4759-4760, Oct. 1, 1999.
Akhundova A.A. et al. "RNA synthesis on immobilized DNA templates in vitro." Biochemistry-Moscow, 43(5):626-628 (1978).
Altschul, S. & Koonin, E. "Iterated profile searches with PSI-BLAST—a tool for discovery in protein databases," Trends Biochem. Sci., 23:444-447, (1998).
Altschul, S., et al. "Basic local alignment search tool," J Mol Biol., 215(3):403-10, (1990).
Beer, N., et al., "On-chip, real time single-copy polymerase chain reaction in picoliter droplets," Analytical Chemistry, 79(22):8471-8475, (Nov. 15, 2007).
Beier M. and Hohseil J.D. "Analysis of DNA-microarray produced by inverse in situ oligonucleotide synthesis." J. Biotechnology, 94:15-22 (2002).
Bethell, D., et al. "From monolayers to nanostructured materials: an organic chemist's view of self-assembly," J. Electroanal. Chem., 409:137-143, (1996).
Binkowski B. F. et al. "Correcting erros in synthetic DNA through consensus shuffling" Nucl. Acids Res., vol. 33, No. 6, e55, 2005.
Booth, P.M., et al. "Assembly and cloning of coding sequences for neurotrophic factors directly from genomic DNA using polymerase chain reaction and uracil DNA glycosylase," Gene 146:303-308 (1994).
Brown, Chappell "BioBricks to help reverse-engineer life," URL.
Carr, P., et al. "Protein-mediated error-correction for de novo DNA synthesis," Nucleic Acids Research, 32(20), e162 (9 pages), (2004).
Caruthers et al., "CXV. Total synthesis of the structural gene for an alanine transfer RNA from yeast. Enzymic joining to form the total DNA duplex," J Mol Biol., 72(2):475-92, (Dec. 28, 1972).
Chalmers, F.P., et al. "Scaling Up the Ligase Chain Reaction-Based Approach to Gene Synthesis" BioTechniques 30:249-252 (2001).
Chan, L. et al. "Refactoring bacteriophage T7," Molecular Systems Biol., doi:10.1038/msb4100025, (Published online Sep. 13, 2005).
Chang, C., et al. "Evolution of a cytokine using DNA family shuffling," Nature Biotechnology, 17: 793-797(1999).
Che, A. "BioBricks++: Simplifying Assembly of Standard DNA Components," [Online] XP002412778, URL:http://austinche.name/docs/bbpp.pdf (Jun. 9, 2004).
Chen, H.B., et al. "A new method for the synthesis of a structural gene," Nucleic Acids Research 18(4):871-878 (1990).
Cherepanov A "Joining of short DNA oligonucleotides with base pair mismatches by T4 DNA ligase" J Biochem. Jan. 2001;129(1):61-8.
Cho, S., et al. "Creating, transporting, cutting and merging liquid droplets by electrowetting-based actuation for digital microfluidic circuits," J. of Microelectromechanical Systems, 12(1):70-80, (Feb. 2003).
Christians, F., et al. "Directed evolution of thymidine kinase for AZT phosphorylation using DNA family shuffling," Nature Biotechnology, 17:259-264(1999).

Crameri, A, et al. "DNA shuffling of a family of genes from diverse species accelerates directed evolution," Nature, 391:288-291(1998).
Crameri, A, et al. "Improved Green Fluorescent Protein by Molecular Evolution Using DNA Shuffling," Nature Biotechnology, vol. 14, Mar. 1996, pp. 315-319.
Crameri, A, et al. "Molecular evolution of an arsenate detoxification pathway by DNA shuffling," Nature Biotechnology, 15:436-438 (1997).
Cui T. et al. "Sepharose-supported DNA as template for RNA synthesis" J. Biotechnology, 66: 225-228 (1998).
Duggan et al., "Expression profiling using cDNA microarrays" Nature Genetics, 21: 10-14, 1999.
Engler C. et al. "A one pot, one step, precision cloning method with high throughput capability" PLoS One, 3: e36471, 2008.
Engler C. et al. "Golden Gate Shuffling: a one-pot DNA shuffling method based on type IIS restriction enzymes" PLoS One, 4:e5553, 2009.
Evans, E. & Alani, E. "Roles for Mismatch Repair Factors in Regulating Genetic Recombination," Molecular & Cellular Biology, 20(21):7839-7844 (Nov. 2000).
Fair, R., "Digital microgluidics: is a true lab-on-a-chip possible?" Microfluid Nonofluid, 3:245-281, (2007).
Ferretti, L. et al. "Total synthesis of a gene for bovine rhodopsin," PNAS, 83:599-603 (Feb. 1986).
Ferrin, L.J., et al. "Sequence-specific ligation of DNA using RecA protein," Proc. Natl. Acad. Sci. USA, 95: 2152-2157 (1998).
Fidalgo, L., et al., "Surface induced froplet fusion in microfluidic devices," Lab on Chip, 7(8)984-986, (2007).
Fleck, O. & Nielsen O. "DNA Repair," J. Cell Science, 117:515-517 (2004).
Fodor et al. (1991) Science 251:767.
Gao, X. et al. "Thermodynamically balanced inside-out (TBIO) PCR-based gene synthesis: a novel method of primer design for high fidelity assembly of longer gene sequences," Nucleic Acids Research, 31(22):e143 (11 pages) (2003).
Goler, J. "BioJADE: A Design and Simulation Tool for Synthetic Biological Systems," MIT Computer Science and Artificial Intelligence Laboratory, AI Technical Report, [Online] URL: http://dspace.mit.edu/bitstream/1721.1/30475/2/MIT-CSAIL-TR-2004-036.pdf, (May 2004).
Grifith, E. and Aklella, S. "Coordinating Multiple Droplets in Planar Array Digital Microfluidic Systems," The International Journal of Robotics Research, 24(11):933-949, (Nov. 2005).
Hacia J.G. "Resequencing and mutational analysis using oligonucleotide microarrays", Nature Genetics, 21(1 suppl):42-47, 1999.
Hacia J.G. et al. "Applications of DNA chips for genomic analysis". Mol Psychiatry. Nov. 1998;3(6):483-92.
Haeberle, S. and Zengerle, R., "Microfluidic platforms for lab-on-chip applications," Lab on a Chip 7(9):1094-1110, (2007).
Hecker, K. "Error Analysis of Chemically Synthesized Polynucleotides," BioTechniques, 24(2):256-260, (Feb. 1998).
Jayaraman K. et al. "Polymerase chain reaction-mediated gene synthesis: synthesis of a gene coding for isozyme c of horseradish peroxidase." Proc Natl Acad Sci US A. May 15, 1991; 88(10): 4084-4088.
Kampke T. "Efficient primer design algorithms" Bioinformatics, 2001, vol. 17, No. 3, pp. 214-225.
Kelly, B., et al., "Miniaturizing chemistry and biology in microdroplets," Chem. Commun., 1773-1788, (2007).
Kim J.H. et al. "Solid-phase genetic engineering with DNA immobilized on a gold surface." J. Biotechnology, 96:213-22 (2002).
Kim, C., et al. "Biological lithography: Improvements in DNA synthesis methods," J. Vac. Sci. Technol. B 22(6):3163-3167 (2004).
Kitamura, K., et al. "Construction of Block-Shuffled Libraries of DNA for Evolutionary Protein Engineering: Y-Ligation- Based Block Shuffling." Protein Engineering, 15(10): 843-853, (Oct. 2002).
Kleppe K., et al. "Studies of polynucleotides: repair replication of short synthetic DNA's as catalyzed by DNA polymerases," J. Mol. Biol. 56:341-361, (1971).
Kodumal et al., "Total synthesis of long DNA sequences: Synthesis of a contiguous 32-kb polyketide synthase gene cluster," PNAS, 101(44):15573-15578, (Nov. 2, 2004).-15578.

(56) References Cited

OTHER PUBLICATIONS

Krieg A "Real-time detection of nucleotide incorporation during complementary DNA strand analysis" Chem. Bio. Chem. 4:589-592 (2003).
Kurian et al. "DNA chip technology". J Pathol.; 187(3):267-71, (Feb. 1999).
Lashkari et al. "An automated multiplex oligonucleotide synthesizer: Development of high throughpout, low cost DNA synthesis". PNAS 92(17):7912-7915, (1995).
Lebedenko E.N. et al. "Method of artificial DNA splicing by directed ligation" Nucleic Acids Research, 19: 6757-6761, 1991.
Liu, Y., et al., "DNA ligation of ultramicrovolume using EWOD microfluidic system with coplanar electrodes: DNA ligation of ultramicrovolume using a EWOD microfluidic system," J. of Micromechanics and Microengineering, 18(4):45017 (7 pages), (2008).
Milton, R., et al. "Total Chemical Synthesis of a D-Enzyme: The Enantiomers ofHIV-1 Protease Show Demonstration of Reciprocal Chiral Substrate Specificity," Science, 256:1445-1448, (Jun. 5, 1992).
Mir K. U. et al. "Sequencing by cyclic ligation and cleavage (CycLic) directly on a microarray captured template". Nucl. Acids Rse. vol. 37, No. 1 e5, 2008.
Mitra R.D. et al. "Fluorescent in situ sequencing on polymerase colonies." Analytical Biochemistry, 320: 55-65 (2003).
Modrich, P. "Strand-specific Mismatch Repair in Mammalian Cells," J. Biol. Chem., 272(40): 24727-24730, (Oct. 3, 1997).
Moore, G. & Maranas C. "Computational Challenges in Combinatorial Library Design for Protein Engineering," AIChE Journal, 50(2):262-272, (Feb. 2004).
Ness, J., et al. "Synthetic Shuffling Expands Functional Protein Diversity by Allowing Amino Acids to Recombine Independently" Nature Biotechnology, 20:1251-1255, (Dec. 2002).
Pon., R. "Solid-phase supports for oligonucleotide synthesis," Methods Mol. Biol., 20:465-496, (1993).
Richmond, K. E., et al., "Amplification and assembly of chip-eluted DNA (AACED): a method for high-throughput gene synthesis", Nucleic Acids Research, Oxford University Press, Surrey, GB, vol. 32, No. 17, pp. 5011-5018, Jan. 1, 2004.
Ryu, D.D.Y., et al. "Recent Progress in Biomolecular Engineering," Biotechnol. Prog. 16: 2-16 (2000).
Saiki, R., et al. "Analysis of enzymatically amplified beta-globin and HLA-DQ alpha DNA with allele-specific oligonucleotide probes," Nature, 324(6093):163-166, (Nov. 13, 1986).
Sgaramella, V., et al. "Studies of polynucleotides, C.: A novel joining reaction catalyzed by T4-polynucleotide ligase", PNAS, 67(3): 1468-1475, (Nov. 1970).
Shabarova, Z., et al., "Chemical ligation of DNA: the first nonenzymatic assembly of a biologically active gene," Nucl. Acids Res., 19(15):4247-4251, (1991).
Smith, H.O., et al. "Generating a synthetic genome by whole genome assembly:<DX174 bacteriophage from synthetic oligonucleotides," PNAS, 100(26):15440-15445 (2003).
Smith, J. & Modrich, P. "Mutation Detection with MutH, MutL, and MutS Mismatch Repair Proteins," Proc. Natl. Acad. Sci. USA, 93:4374-4379, (Apr. 1996).
Soderlind et al. "Domain libraries: Synthetic diversity for de novo design of antibody V-regions." Gene, 160 (1995) 269-272.
Stamm et al., "Sanchored PCR: PCR with CDNA Coupled to a solid phase," Nucleic Acids Research, 19(6):1350, (Mar. 25, 1991).
Stekel D. "Microarrays: Making Them and Using Them in Microarray Bioinformatics," Microarray Bioinformatics, Cambridge University Press, 2003.
Stemmer et al. "Single-step assembly of a gene and entire plasmid from large numbers of oligodeoxyribonucleotides" Gene 164: 49 (1995).
Teh, S-Y, et al., "Droplet microfluidics," Lab on Chip, 8(2), (2008).
Tian et al., "Accurate multiplex gene synthesis from programmable DNA microchips," Nature, 432:1050-1054, (Dec. 2004).

Tsutakawa, S. & Morikawa, K. "The Structural Basis of Damaged DNA Recognition and Endonucleolytic Cleavage for Very Short Patch Repair Endonuclease," Nucleic Acids Research, 29(18):3775-3783, (2001).
Weiler and Hoheisel "Combining the Preparation of Oligonucleotide Arrays and Synthesis of High-Quality Primers." Analytical Biochemistry, vol. 243, Issue 2, Dec. 15, 1996, pp. 218-227.
Wilgenbus & Lichter "DNA chip technology ante portas" J. Mol. Med 1999, 77:761-768.
Xiong et al. "PCR based accurate synthesis of long DNA sequences" Nature protocols 1 (2): 791 (2006).
Xiong, A., et al. "A simple, rapid, high-fidelity and cost-effective PCR-based two-step DNA synthesis method for long gene sequences," Nucleic Acids Research, 32(12):e98 (10 pages), (2004).
Xu, Y. and Kool, E., "A Novel 5'-lodonucleoside allows efficient nonenzymatic ligation of single-stranded and duplex DNAs" Tetrahedron Letter, 38(32):5595-5598, (Aug. 11, 1997).
Xu, Y. and Kool, E., "High sequence fidelity in a non-enzymatic DNA autoligation reaction" Nuc. Acids Res., 27(3):875-881, (1999).
Xu, Y., et al., "Nonenzymatic autoligation in direct three-color detection of RNA and DNA point mutations" Nature Biotech., 19:148-52, (Feb. 2001).
Zha, D., et al. "Assembly of Designed Oligonucleotides as an Efficient Method for Gene Recombination: A New Tool in Directed Evolution," ChemBioChem, 4:34-39, (2003).
Zhao, H., et al. "Molecular Evolution by Staggered Extension Process (Step) In Vitro Recombination," Nature Biotechnology, 16:258-261, (Mar. 1998).
Andersen, J., et al. "New Unstable Variants of Green Fluorescent Protein for Studies of Transient Gene Expression in Bacteria," Applied and Environmental Microbiology, 64(6):2240-2246 (Jun. 1998).
Coco, W., et al. "Growth Factor Engineering by Degenerate Homoduplex Gene Family Recombination," Nature Biotechnology, 20: 1246-1250, (Dec. 2002).
Dafhnis-Calas, F., et al. "Iterative in vivo assembly of large and complex transgenes by combining the activities of DC31 integrase and Cre recombinase," Nucleic Acids Research, 33(22): 1-14 (2005).
Fisch, I. et al. "A Strategy of Exon Shuffling for Making Large Peptide Repertoires Displayed on Filamentous Bacteriophage," Proceedings of the National Academy of Sciences of USA, 93:7761-7766, (Jul. 1996).
Gardner, T., et al. "Construction of a genetic toggle switch in *Escherichia coli*," Nature, 403:339-342 (Jan. 2000).
Gibbs, W. "Synthetic Life," Scientific American, [Online] URL: htto://www.sciam.com/orint version.cfm?articleID=0009FCA4, (Apr. 26, 2004).
Guntas, G., et al. "A molecular switch created by in vitro recombination of nonhomologous genes," Chem. & Biol., 11: 1483-1487 (Nov. 2004).
Guntas, G., et al. "Directed Evolution of Protein Switches and Their Application to the Creation of Ligand-Binding Proteins," Proc. Natl. Acad. Sci. USA, 102(32):11224-11229 (Aug. 9, 2005).
Gulati S. et al. "Opportunities for microfluidic technologies in synthetic biology." Journal of the Royal Society, Interface/ The Royal Society, vol. 6, Suppl. 4, S493-S506, 2009.
Heeb, S., et al. "Small, Stable Shuttle Vectors Based on the Minimal pVSl Replicon for Use in Gram-Negative Plant-Associated Bacteria," MPMI, 13(2):232-237 (2000).
Johnston M. "Gene chips: Array of hope for understanding gene regulation". Current Biology, 8: (5) R171, 1998.
Jones, T., et al. "The Development of a Modified Human IFN-alpha2b Linked to the Fe Portion of Human IgG1 as a Novel Potential Therapeutic for the Treatment of Hepatitis C Virus Infection," Journal of Interferon & Cytokine Research, 24:560-572, (2004).
Kim, Y., et al. "Insertion and Deletion Mutants of FokI Restriction Endonuclease," J. Biol. Chem., 269(50):31978-31982 (1994).
Kolisnychenko, V., et al. "Engineering a Reduced *Escherichia coli* Genome," Genome Research, 12:640-647, (2002).
Kong, D., et al., "Parallel gene synthesis in microfluidic device," Nucleic Acids Research, 35(8):e61 (9 pages), (2007).

(56) References Cited

OTHER PUBLICATIONS

Kotsopoulou, E., et al. "A Rev-Independent Human Immunodeficiency Virus Type 1 (HIV-1)-Based Vector That Exploits a Codon-Optimized HIV-1 gag-pol Gene," Journal of Virology, 74(10):4839-4852, (May 2000).
Kowalczykowski, S. "Initiation of genetic recombination and recombination-dependent replication," TIBS, 25:156-165, (Apr. 2000).
Kowalczykowski, S. "In vitro reconstitution of homologous recombination reactions," Experientia, 50:204-215, (1994).
Lamers, M., et al. "ATP Increases the Affinity between MutS ATPase Domains," J. Biol. Chem., 279(42):43879-43885, (Oct. 15, 2004).
Leamon, J., et al., "A massively parallel PicoTiterPlate™ based platform for discrete picoliter-scale polymerase chain reactions," Electrophoresis, 24(21):3769-3777, (Nov. 2003).
Lee, K., et al. "Genetic approaches to Studying Protein Synthesis: Effects of Mutations at ΨI516 and A535 in *Escherichia coli* 16S rRNA," J. Nutr., 131:2994S-3004S, (2001).
Lewis, J. & Hatfull, G. "Control of directionality in intergrase-mediated recombination: examination of recombination directionality factors (RDFs) including Xis and Cox proteins," Nucl. Acids Res., 29(11):2205-2216 (2001).
Li, C., and Evans, R. "Ligation independent cloning irrespective of restriction site compatibility," Nucl. Acids Res., 25(20):4165-4166 (1997).
Li L et al. "Alteration of the cleavage distance of Fok I restriction endonuclease by insertion mutagenesis." Proc Natl Acad Sci USA. 90(7): 2764-2768 (Apr. 1993).
Link, A., et al. "Methods for generating precise deletions and insertions in the genome of wild-type *Escherichia coli*: Application to open reading frame characterization," J. Bacteriol., 179(20):6228-6237, (Oct. 1997).
Liu G. et al. "DNA computing on surfaces." Nature, 403:175179 (2000).
Liu, Y., et al., "DNA ligation of ultramicrovolume using EWOD microfluidic system with coplanar electrodes" Journal of Micromechanics & Microengineering, Institute of Physics, 18(4):45017 (7 pages), (Apr. 2008).
Luo, P., et al. "Development of a Cytokine Analog with Enhanced Stability Using Computational Ultrahigh Throughput Screening," Protein Science, 11:1218-1226, (2002).
Lutz, S. & Benkovic, J. "Homology-Independent Protein Engineering," Current Opinion in Biotechnology, 11:319-324, (2000).
Mandecki W. "Oligonucleotide-directed double-strand break repair in plasmids of *Escherichia coli*: A method for site-specific mutagenesis." 1986, PNAS, 83:7177-7181.
Margulies, M., et al., "Genome sequencing in microfabricated high-density picolitre reactors," Nature, 437(7057):376-80, (Sep. 15, 2005).
Mfick, S., et al. "Crossover isomer bias is the primary sequence-dependent property of immobilized Holliday junctions," Proc. Natl. Acad. Sci. USA, 94:9080-9084, (Aug. 1997).
Morton, Oliver "Life, Reinvented," Wired, http:www.wired.com/wired/archive!13.01/mit_pr.html (2005).
Nakamaye, K., et al. "Direct sequencing of polymerase chain reaction amplified DNA fragments through the incorporation of deoxynucleoside alpha-thiotriphosphates," Nucleic Acids Research, 16(21):9947-9959, (1988).
Ness, J., et al. "DNA shuffling of subgenomic sequences of subtilisin," Nature Biotechnology 17: 893-896 (1999).
Nilsson P. et al. "Real-Time monitoring of DNA manipulations using biosensor technology" Analytical Biochemistry, 1995, 224:400-408.
Noirot, P. & Kolodner, R. "DNA Strand Invasion Promoted by *Escherichia coli* RecT Protein," J. Biol. Chemn., 273(20):12274-12280, (May 15, 1998).
Novy, R., et al. "Ligation Independent Cloning: Efficient Directional Cloning of PCR Products," Novagen, Inc., InNovations, 5: 1-3, http://www.emdbiosciences.com/html/NVG/inNovations.html), (1996).
Panet A. and Khorana G.H. "Studies of polynucleotides: the linkage of deoxyribopolynucleotides templates to cellulose and its use in their replication." J. Biol. Chem. 249(16):5213-5221 (1974).
Parr, R. & Ball, J. "New donor vector for generation of histidine-tagged fusion proteins using the Gateway Cloning System," Plasmid, 49:179-183, (2003).
Peters, J. & Craig, N. "Tn7: Smarter Than We Thought," Nature, 2:806-814, (Nov. 2001).
Posfai, G., et al. "In vivo excision and amplification of large segments of the *Escherichia coli* genome," Nucl. Acids Res., 22(12):2392-2398, (1994).
Posfai, G., et al. "Markerless gene replacement in *Escherichia coli* stimulated by a double-strand break in the chromosome," Nucl. Acids Res., 27(22):4409-4415, (1999).
Regalado, A. "Next Dream for Venter: Create Entire Set of Genes From Scratch," Wall Street Journal, Al, (Jun. 29, 2005).
Rouwendal, G., et al. "Enhanced Expression in Tobacco of the Gene Encoding Green Fluorescent Protein by Modification of its Codon Usage," Plant Molecular Biology, 33:989-999, (1997).
Sa-Ardyen, P., et al. "The flexibility of DNA double crossover molecules," Biophys. J., 84:3829-3837, (Jun. 2003).
Sakabe, N., et al. "A Bioinformatics Analysis of Alternative Exon Usage in Human Genes Coding for Extracellular Matrix Proteins," Genetics and Molecular Research, 3(4):532-544, (2004).
Saks, M. "Making sense out of nonsense," PNAS, 98(5): 2125-2127, (Feb. 27, 2001).
Sato, T., et al. "Production of menaquinone (vitamin K2)-7 by *Bacillus subtilis*," J. of Bioscience and Engineering, 91(1):16-20, (2001).
Schaerli, Y., et al., "Continuous-Flow polymerase Chain reaction of single-copy DNA Micorfluidic Microdroplets," Anal. Chem., 81: 302-306, (2009).
Semizarov, D., et al. "Stereoisomers of Deoxynucleoside 5'-Triphosphates as Substrates for Template- dependent and -independent DNA Polymerases," J. Biol. Chem., 272(14) 9556-9560 (1997).
Shao, Z., et al. "Random-Priming in Vitro Recombination: An Effective Tool for Directed Evolution," Nucleic Acids Research, 26(2):681-683, (1998).
Shendure, J., et al., "Accurate Multiplex Polony Sequencing of an Evolved Bacterial Genome," Science, 309:1728-1732, (Sep. 9, 2005).
Sieber, V., et al. "Libraries of Hybrid Proteins From Distantly Related Sequences," Nature Biotechnology, 19: 456-460, (May 2001).
Strizhov et al. "A synthetic cryiC gene, encoding a *Bacillus thuringiensis* delta-endotoxin, confers Spodotera resistance in Alfafa and Tobacco" P.N.AS., 1996, vol. 93, No. 26, pp. 15012-15017.
Tan, S., et al. "Zinc-finger protein-targeted gene regulation: Genomewide single-gene specificity," PNAS, 100(21):11997-12002, (Oct. 14, 2003).
Tang K. et al. "Chip-based genotyping by mass spectrometry." PNAS, 96:10016-10020 (1999).
von Neumann T. "The general and logical theory of automata," Pergamon Press, Taub A.H (Editor) vol. 5, 288-326 (1948).
Wheeler DL "Database resources of the National Center for Biotechnology Information" Nucleic Acids Res. 29(1): 11-6 (Jan. 2001).
Wiedmann, M., "Ligase chain reaction (LCR)—overview and applications", 3:S51-S64, http:genome.cshlp.org/content/3/4/S51.refs.html, Copyright 1994 by Cold Spring Harbor Laboratory.
Xuei et al. "Use of SAM(2)(R) biotin capture membrane in microarrayed compound screening (mu ARCS) format for nucleic acid polymerization assays" Journal of Biomolecular Screening 8:273-282 (2003).
Yolov et al. "RNA-synthesis by use of T7-RNA-Polymerase and immobilized DNA in a flowing-type reactor". Bioorganicheskaya Khimiya, 17:789-794 (1991) (English Abstract Only).
Zha, D., et al. "Assembly of Designed Oligonucleotides as an Efficient Method for Gene Recombination: A New Tool in Directed Evolution," ChemBioChem, 4: 34-39, (2003).
Zhang, C., et al., "PCR microfluidic devices for DNA amplification," Biotechnology Advances, 24(3):243-284, 2006.

\* cited by examiner

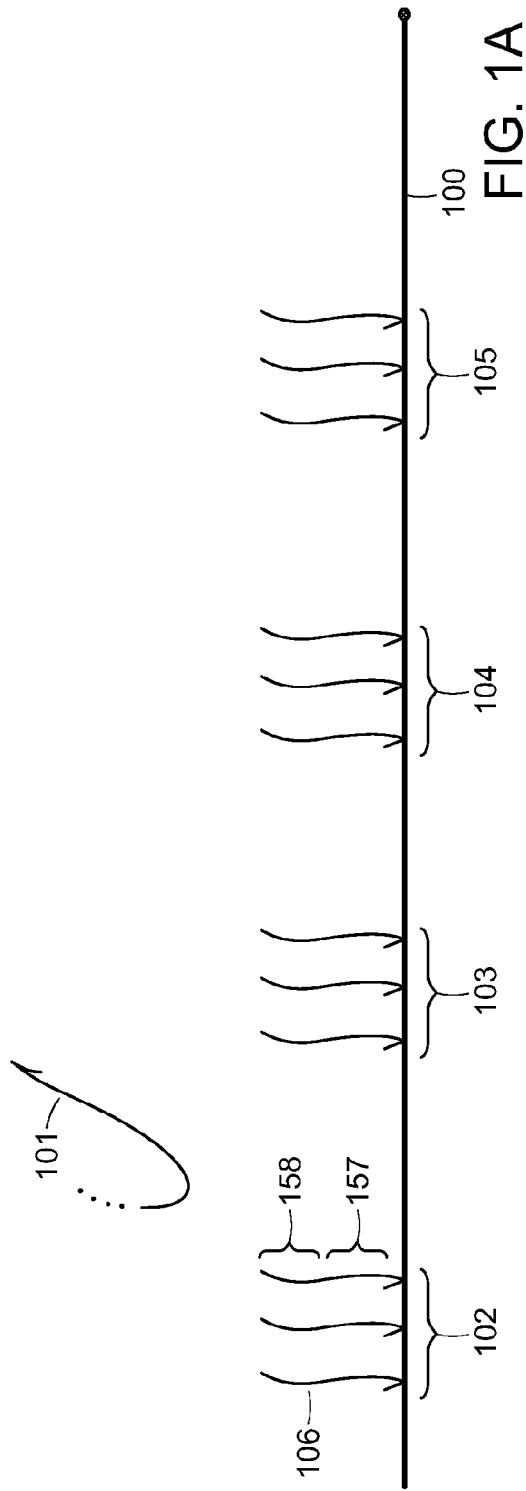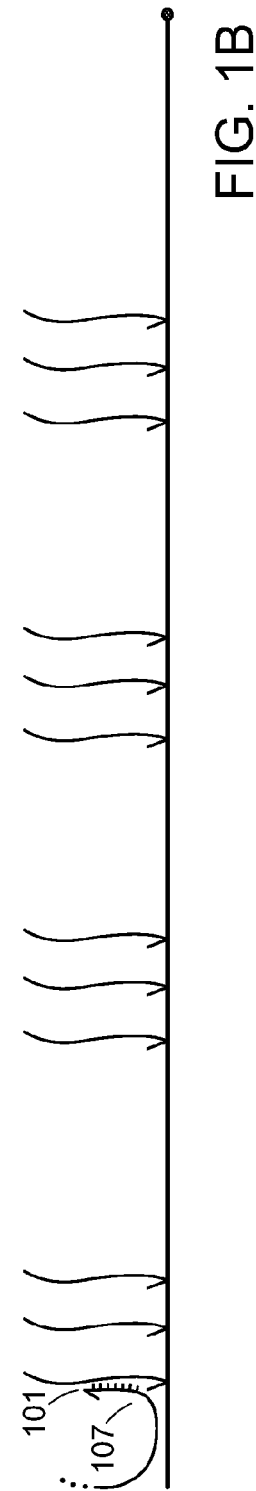

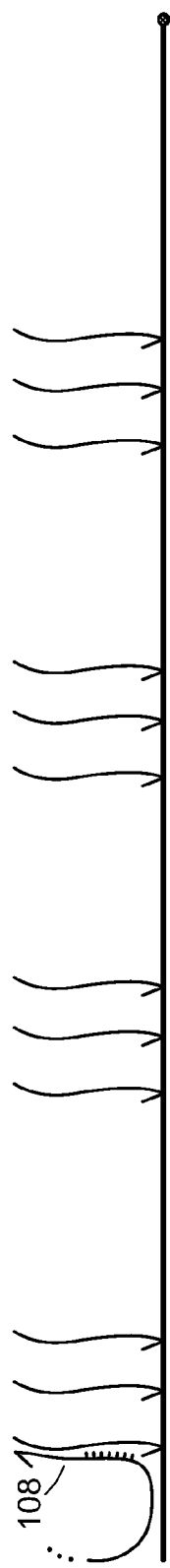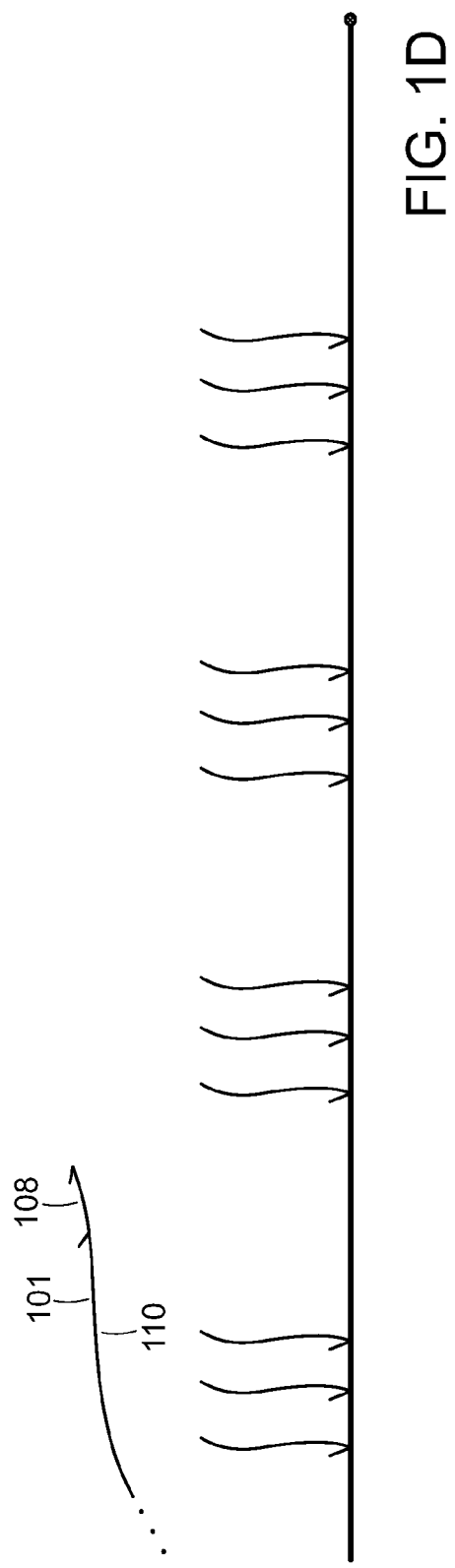

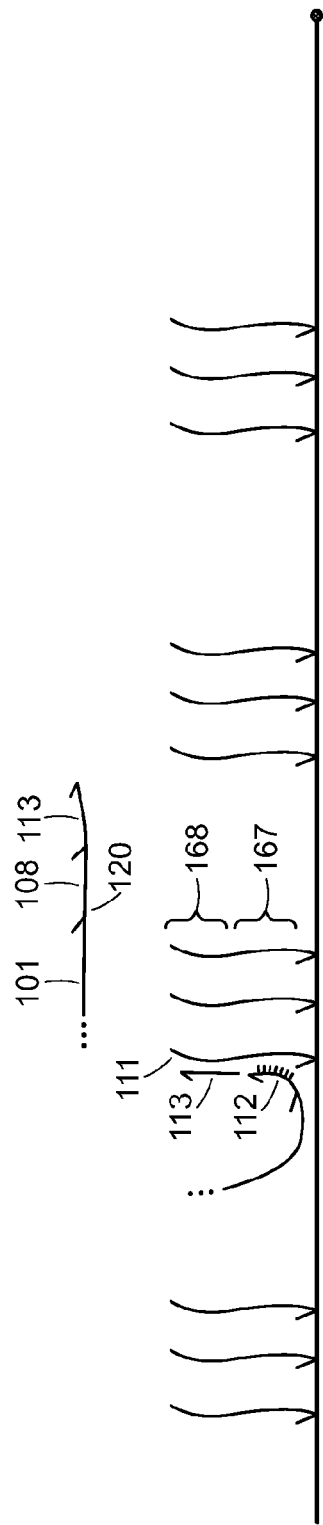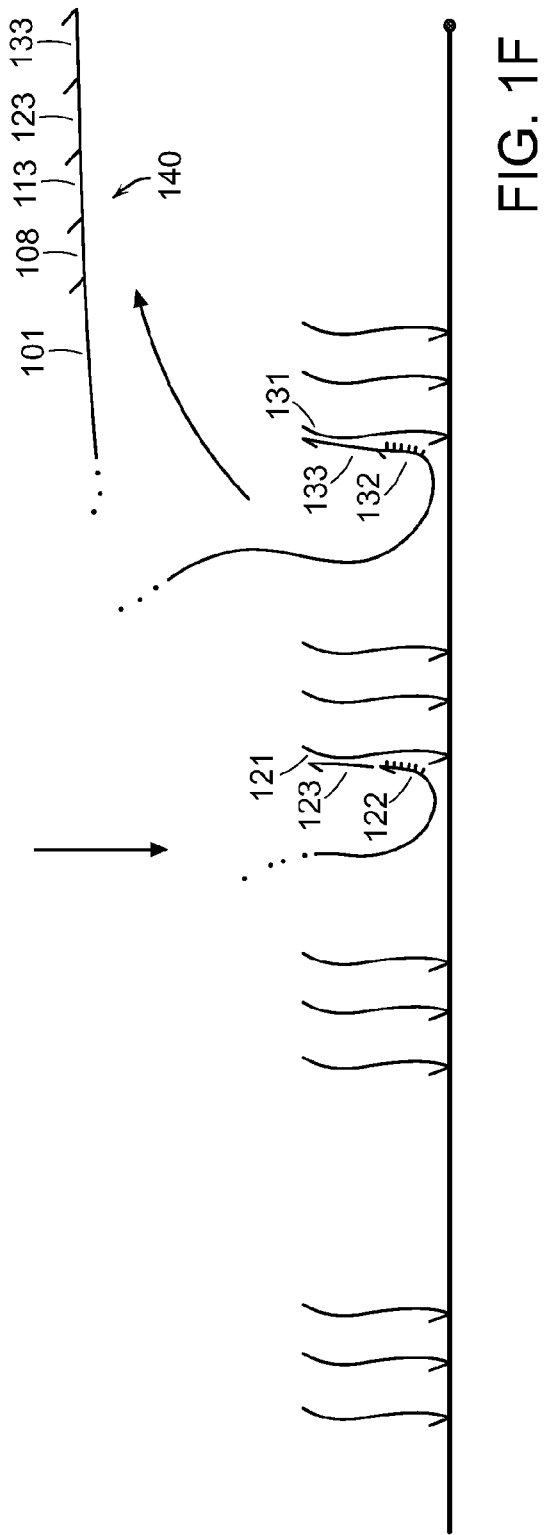

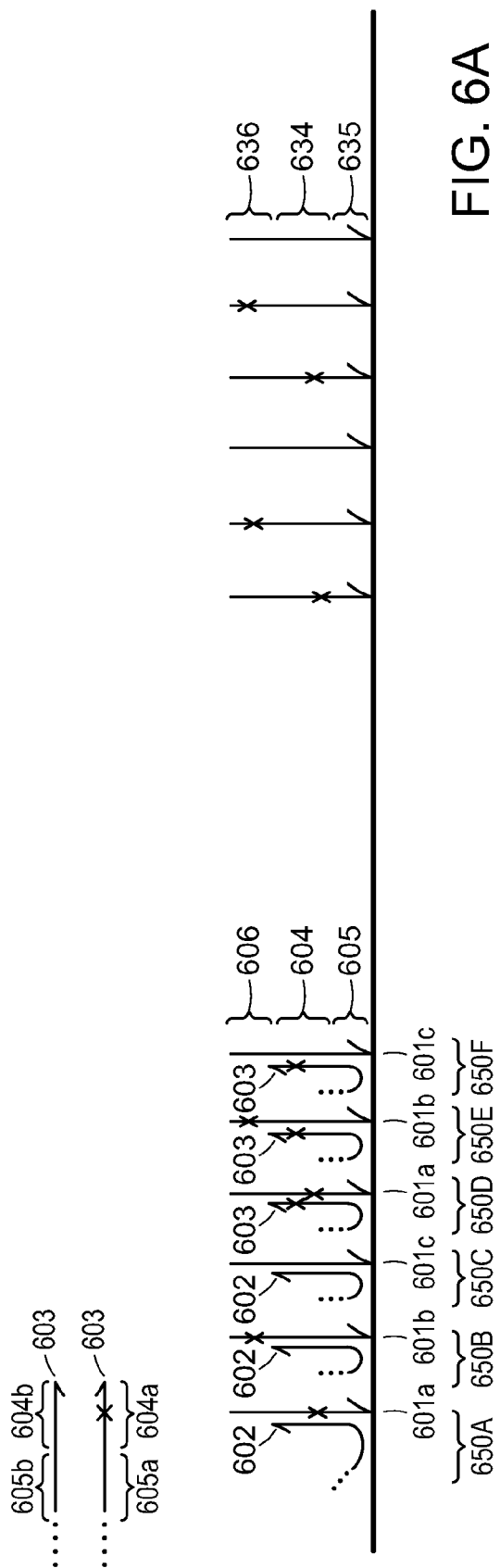

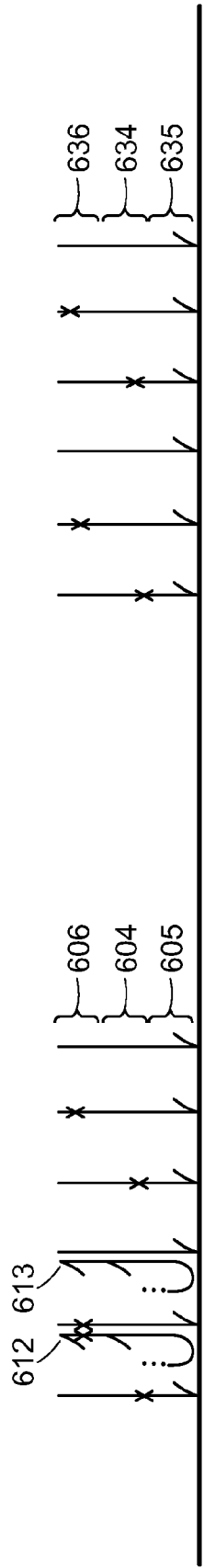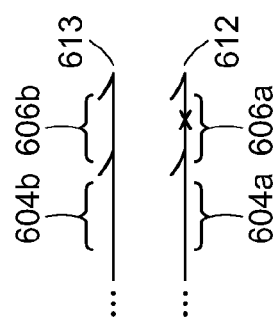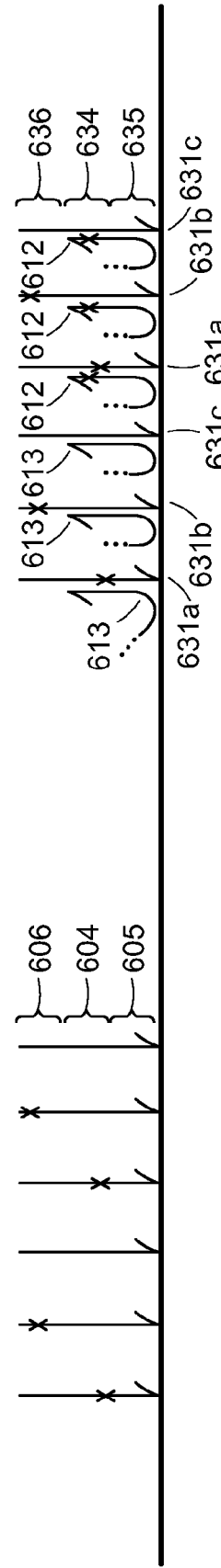
FIG. 6D
FIG. 6E

ASSEMBLY OF HIGH FIDELITY POLYNUCLEOTIDES

RELATED APPLICATIONS

This application is a National Phase Application of International Application No. PCT/US2011/020335 filed Jan. 6, 2011, which claims the benefit of U.S. Provisional Patent Application Ser. No. 61/293,192, filed Jan. 7, 2010; U.S. Provisional Patent Application Ser. No. 61/310,076, filed Mar. 3, 2010; and U.S. Provisional Patent Application Ser. No. 61/334,416, filed May 13, 2010, the contents of each of the foregoing applications are incorporated herein by reference in their entirety.

STATEMENT REGARDING FEDERALLY SPONSORED RESEARCH

This invention was made with United States Government support under the cooperative agreement number 70NANB7H7034N awarded by the National Institute of Standards and Technology. The United States Government has certain rights in the invention.

FIELD OF THE INVENTION

Methods and apparatuses provided herein relate to the synthesis and assembly of high fidelity nucleic acids and nucleic acid libraries having a predefined sequence. More particularly, methods and apparatuses are provided for polynucleotide synthesis, error reduction, and/or sequence verification on a solid support. In some embodiments, picoliter and sub-picoliter dispensing and droplet moving technologies are applied to access and manipulate the oligonucleotides on DNA microarrays.

BACKGROUND

Using the techniques of recombinant DNA chemistry, it is now common for DNA sequences to be replicated and amplified from nature and then disassembled into component parts. As component parts, the sequences are then recombined or reassembled into new DNA sequences. However, reliance on naturally available sequences significantly limits the possibilities that may be explored by researchers. While it is now possible for short DNA sequences to be directly synthesized from individual nucleosides, it has been generally impractical to directly construct large segments or assemblies of polynucleotides, i.e., polynucleotide sequences longer than about 400 base pairs.

Oligonucleotide synthesis can be performed through massively parallel custom syntheses on microchips (Zhou et al. (2004) Nucleic Acids Res. 32:5409; Fodor et al. (1991) Science 251:767). However, current microchips have very low surface areas and hence only small amounts of oligonucleotides can be produced. When released into solution, the oligonucleotides are present at picomolar or lower concentrations per sequence, concentrations that are insufficiently high to drive bimolecular priming reactions efficiently. Current methods for assembling small numbers of variant nucleic acids cannot be scaled up in a cost-effective manner to generate large numbers of specified variants. As such, a need remains for improved methods and devices for high-fidelity gene assembly and the like.

Furthermore, oligonucleotides on microchips are generally synthesized via chemical reactions. Spurious chemical reactions cause random base errors in oligonucleotides. One of the critical limitations in chemical nucleic acid synthesis is the error-rate. The error rate of chemically-synthesized oligonucleotides (e.g. deletions at a rate of 1 in 100 bases and mismatches and insertions at about 1 in 400 bases) exceeds the error rate obtainable through enzymatic means of replicating an existing nucleic acid (e.g., PCR). Therefore, there is an urgent need for new technology to produce high-fidelity polynucleotides.

SUMMARY

Aspects of the invention relate to methods and apparatuses for preparing and/or assembling high fidelity polymers. Also provided herein are devices and methods for processing nucleic acid assembly reactions and assembling nucleic acids. It is an object of this invention to provide practical, economical methods of synthesizing custom polynucleotides. It is a further object to provide methods of producing synthetic polynucleotides that have lower error rates than synthetic polynucleotides made by methods known in the art.

According to one embodiment, the invention provides a method for producing a polynucleotide having a predetermined sequence on a solid support. In some embodiments, pluralities of support-bound single-stranded oligonucleotides are provided at different features of a solid support, each plurality of oligonucleotides having a predefined sequence and each plurality being bound to a different discrete feature of the support. In some embodiments, each plurality of oligonucleotides comprises a sequence region at its 5' end that is the same as a sequence region of a 3' end of another oligonucleotide and a sequence region at its 3' end that is the same as a sequence region at a 5' end of a different oligonucleotide and wherein the first plurality of oligonucleotides has a 3' end that is complementary to a 3' end of a first input single-stranded oligonucleotide. In some embodiments, the first plurality of oligonucleotide comprises at its 5' end a sequence region that is the same as a sequence region at the 3' end of a second oligonucleotide and the Nth plurality of oligonucleotide comprises at its 3' end a sequence region that is the same as a sequence region of the (N−1) oligonucleotide. In some embodiments, a first input oligonucleotide is provided in solution at the feature where the first plurality of oligonucleotides is immobilized. A first plurality of complementary oligonucleotides is synthesized by template-dependent synthesis in which each of the first plurality of support-bound oligonucleotides is hybridized with the first input oligonucleotide thereby forming an extension product duplex. The extension product duplex is dissociated to release the first plurality of complementary oligonucleotides. The first plurality of complementary oligonucleotides (e.g., second input oligonucleotide) may then anneal to a second plurality of support-bound single stranded oligonucleotides wherein the annealing of the first plurality of complementary oligonucleotides to the second plurality of support-bound oligonucleotides serves as a primer for extension of the first plurality of complementary oligonucleotides. The cycles of primer extension, dissociation and annealing can be repeated until the target polynucleotide is synthesized. The target polynucleotide can be amplified. In some embodiments, the first input oligonucleotide is a primer, for example a universal primer or a unique primer. In other embodiments, the first input oligonucleotide is a synthetic oligonucleotide or a single stranded nucleic acid fragment. The plurality of support bound oligonucleotides may be synthesized on the solid support or synthetic oligonucleotides can be spotted on the solid support. In some embodiments, the solid support is a microarray device.

Some aspects of the invention relates to a method for producing at least one polynucleotide having a predefined sequence, the method comprising providing at least a first and a second plurality of support-bound single-stranded oligonucleotides, wherein each first and second plurality of oligonucleotides has a predefined sequence and is bound to a discrete feature of the support, each first plurality of oligonucleotides comprising a sequence region at its 5' end that is the same as a sequence region of a 3' end of the second plurality of oligonucleotides. A plurality of first input single-stranded oligonucleotides is provided wherein the 3' end of the plurality of the first input oligonucleotide is complementary to the 3' end of the first plurality of oligonucleotides. The plurality of first input oligonucleotides is hybridized to the first plurality of support-bound oligonucleotides at a first feature and a first plurality of complementary oligonucleotides is generated in a chain extension reaction, thereby forming an extension product duplex. The extension product duplex is dissociated, thereby producing a first plurality of complementary oligonucleotides. The first plurality of complementary oligonucleotides is transferred from the first feature to a second feature, thereby bringing into contact the first plurality of complementary oligonucleotides to the second plurality of support-bound oligonucleotides. The first plurality of complementary oligonucleotides is then annealed to the second plurality of support-bound single stranded oligonucleotides at the second feature, wherein the annealing of the first plurality of complementary oligonucleotides to the second plurality of support-bound oligonucleotides serves as a primer for extension of the first plurality of complementary oligonucleotides, thereby producing the polynucleotide.

In some embodiments, a third plurality of support-bound single-stranded oligonucleotides is provided wherein each third plurality of oligonucleotides has a predefined sequence and is bound to a third discrete feature of the support, each third plurality of oligonucleotides comprising a sequence region at its 3' end that is the same as a sequence region of a 5' end of the second plurality of oligonucleotides, and repeating annealing, chain extension, denaturation and transferring steps to produce a longer polynucleotide.

In some aspects of the invention, the reaction steps are performed within discrete droplet volumes (nanoliter, picoliter or subpicoliter droplets volumes). In some embodiments, the annealing and extension steps are performed within a first droplet volume at a first feature and the first plurality of complementary oligonucleotides is released within the first droplet volume. The first droplet volume may be moved to a second feature comprising a second plurality of support-bound oligonucleotides. Droplets volumes may be moved at specific locations of the solid support by different techniques such as electrowetting or following a hydrophilicity gradient. In some embodiments, the whole support is subjected to conditions promoting annealing or primer extension or denaturing. In some embodiments, the whole support or selected features are subjected to thermocycling conditions. In other embodiments, selected features are subjected to conditions promoting annealing or primer extension or denaturing.

Aspects of the invention relate to the synthesis of at least one high fidelity target polynucleotide having a predetermined sequence. In some embodiments, the method comprises the steps of providing pluralities of different support-bound single-stranded oligonucleotides at different features of a solid support, wherein each plurality of support-bound oligonucleotides has at least two sequence regions, a first sequence region at its 5' end that is the same as a sequence region of the 3' end of another oligonucleotide and a second sequence region at its 3' end that is the same as a sequence region at a 5' end of a different oligonucleotide and wherein each plurality of oligonucleotides has a 3' end that is complementary to a 3' end of a different input single-stranded polynucleotide. A first input polynucleotide is provided in solution at the feature of a first plurality of support-bound oligonucleotides wherein the input polynucleotide is generated from a previous extension step. The first input polynucleotide is hybridized to the first plurality of support-bound oligonucleotides under hybridizing conditions thereby forming duplexes. In some embodiments, the duplexes may comprise duplexes having at least one mismatch in a complementary region and/or duplexes that do not comprise a mismatch in the complementary region. The duplexes having at least one mismatch in the complementary region are unstable duplexes that can be denatured under stringent melt conditions. The stringent melt conditions (e.g., stringent melt temperature) do not denature the duplexes that do not comprise a mismatch in the complementary region (stable duplexes). Error-containing input polynucleotides are then released in solution and removed. The remaining stable duplexes can then be subjected to primer extension conditions, generating a first plurality of complementary oligonucleotides by template-dependent synthesis, thereby forming an extension product duplex. The extension product duplex is dissociated to release a second input polynucleotide (or complementary polynucleotide). The second input polynucleotide can be allowed to anneal to a second plurality of support-bound single stranded oligonucleotides. Cycles of stringent melt, extension, dissociation and annealing are repeated until the target polynucleotide is synthesized.

In some embodiments, the annealing and stringent melt steps can be performed within a first droplet volume at a first feature thereby releasing the error-containing polynucleotides in the first droplet volume. The first droplet volume can be discarded and a second droplet volume comprising reagent for primer extension can be added to the first feature under condition promoting primer extension. Complementary strands are released into the second droplet volume and the second droplet volume may be moved to a second feature comprising a second plurality of support bound oligonucleotides. In some embodiments, the support-bound oligonucleotides comprise a third sequence region at the 3' end of the oligonucleotide. In some embodiments, the plurality of different support-bound single-stranded oligonucleotides at different features of a solid support comprises at least three sequence regions: a 5' end sequence region N, at least two sequence regions (N−1) and (N−2) that are complementary to the 3' end of an input polynucleotide, and a 3' end sequence region. The (N−1) sequence region is adjacent to the 5' end sequence region and the (N−2) sequence region is adjacent to the (N−1) sequence region. In some embodiments, a first input polynucleotide is provided in solution at the feature of a first plurality of support-bound oligonucleotides wherein the first input polynucleotide comprises sequences regions complementary to the at least two sequences regions (N−1) and (N−2). The first input polynucleotide is hybridized with the first plurality of support-bound oligonucleotides under hybridizing conditions wherein the 3' end of the first input polynucleotide hybridizes, at least in part, to the at least two sequence regions (N−1) and (N−2) of the oligonucleotides thereby forming duplexes, the duplexes comprising a first duplex having at least one mismatch in a complementary region and a second duplex that does not comprise a mismatch in the complementary region. The first duplex may be denatured under stringent melt conditions without denaturing the second duplex. In this fashion, error-containing input polynucleotides are released in solution and may be removed. In subsequent step, a first plurality of complementary oligonucleotides is generated by template-dependent synthesis under condition promoting extension of the input polynucleotides thereby forming an extension product duplex. The extension product is dissociated, releasing a second input polynucleotide. The second input polynucleotide may anneal to a second plurality of support-bound single-stranded oligonucleotides and by repeating the cycles of stringent melt, extension, dissociation and annealing, the target polynucleotide is synthesized.

Aspects of the invention relate to a method of removing error-containing polynucleotides synthesized on a solid support, the method comprising the following steps. A plurality of support-bound single stranded oligonucleotides is provided on a solid support; the oligonucleotides comprising a 5' end sequence region, a 3' end sequence region and at least two different sequences regions (N−1) and (N−2) between the 5' end and the 3' end sequence regions. An input polynucleotide, the input polynucleotide being a product of at least two cycles (N−2) and (N−1) of chain extension reaction is provided. The input polynucleotide is hybridized to the plurality of support-bound oligonucleotides, thereby forming duplexes in which the 3' end of the input polynucleotide hybridizes to the (N−1) and (N−2) sequences regions of the support-bound oligonucleotide. In some embodiments, the duplexes comprise duplexes having at least one mismatch in a complementary region and duplexes that do not comprise a mismatch in the complementary region. The duplexes having at least one mismatch in the complementary region are denatured under stringent melt conditions releasing error-containing input polynucleotides. In some embodiment, the support-bound oligonucleotides comprise at least three different sequences regions (N−1), (N−2) and (N−3) between the 5' end and the 3' end sequence regions, and the input polynucleotide hybridizes to the (N−1), (N−2) and (N−3) sequences regions of the support-bound oligonucleotides. In some embodiments, the 3' end sequence is a spacer sequence and may comprise a primer binding site.

In some embodiments, the (N−1) sequence is adjacent to the 5' end sequence region and the (N−2) sequence region is adjacent to the (N−1) sequence region and so on. In some embodiments, each input polynucleotide is the product of a chain extension reaction. For example, the input polynucleotide may be the product of at least one, at least two, at least three, etc. extension chain reactions, each extension chain reaction using a different plurality of support-bound oligonucleotides as a template. In some embodiments, the input polynucleotide is the product of at least two extension chain reactions, each extension chain reaction adding a sequence at the 3' end of the input polynucleotide. For example, a first extension chain reaction results in the addition of a first sequence complementary to sequence 1, the (n−2) extension reaction results in the addition of a sequence complementary to sequence (N−2), the (n−1) extension reaction results in the addition of a sequence complementary to sequence (N−1) and so on.

In some embodiments, the extension duplexes are subjected to shuffling process before undergoing a next cycle of extension. The shuffling process comprises the steps of denaturing extension duplexes such as single-stranded extension products are released into solution; re-annealing single-stranded extension products to the support-bound oligonucleotides thereby producing re-annealed duplexes; subjecting the re-annealed duplexes to stringent melt conditions to dissociate error-containing duplexes; removing error-containing single-stranded extension products; and dissociating the error-free duplexes thereby releasing error-free extension products in solution.

In some embodiments, each plurality of oligonucleotides is designed to serve as a template to a different polymerase extension reaction, thereby forming pluralities of extension duplexes, wherein each plurality of extension duplexes has a substantially identical melting temperature. In some embodiments, the difference of melting temperature between the plurality of duplexes is less than 10° C., less than 5° C., less than 1° C.

In some aspects, methods for producing at least one double-stranded polynucleotide having a predefined sequence are provided. In some embodiments, in a first step, a polynucleotide is synthesized on a discrete feature of a support. The polynucleotide comprises a 3' terminal sequence region complementary to a 5' region of an oligonucleotide at a discrete feature and a 5' terminal region that is not complementary to the oligonucleotide. At least a first plurality of support-bound oligonucleotides is provided, wherein the at least first plurality of oligonucleotides has a predefined sequence and is bound to a first discrete feature of the support, each first plurality of oligonucleotides comprising a primer binding sequence at its 3' end and a sequence region at its 5' end substantially identical to a 5' end of the polynucleotide. In a subsequent step, the primer is annealed to the first plurality of oligonucleotides at the first discrete feature, wherein the annealing of the primer to the first plurality of support-bound oligonucleotides serves as a primer for extension of the first plurality of complementary oligonucleotides, thereby generating a first extension product duplex. The primer is then removed from the extension duplex. Preferably, the primer sequence comprises at least one Uracil and the primer is removed using a mixture of Uracil DNA glycosylase (UDG) and the DNA glycosylase-lyase Endonuclease VIII. The first extension product duplex is dissociated thereby producing a first plurality of complementary oligonucleotides which are then transferred to a the discrete feature comprising the polynucleotide thereby bringing into contact the first plurality of oligonucleotides with the polynucleotide, wherein the first plurality of oligonucleotides is complementary to the 5' end of the polynucleotide. The first plurality of complementary oligonucleotides is then annealed to the polynucleotide, wherein the annealing of the oligonucleotides serves as a primer for extension of the polynucleotide, thereby producing a double stranded polynucleotide.

In some embodiments, the method for producing at least one double-stranded polynucleotide having a predefined sequence comprises the following steps: a) providing at least a first, a second and a third plurality of support-bound single-stranded oligonucleotides, each first, second and third plurality of oligonucleotides having a predefined sequence and being bound to a discrete feature of the support. Each first and second plurality of oligonucleotides comprise a primer binding site at its 3' end that is complementary to a primer sequence and the first plurality of oligonucleotide has a sequence 5' sequence region that is complementary to the 5' sequence region of the second plurality of oligonucleotides and a sequence region between the primer binding site and the 5' sequence region that is identical to a 5' end of the third plurality of oligonucleotides, and the second plurality of oligonucleotides comprises a primer binding site at its 3' end; b) annealing the primers to the primer binding sites of the first and the second plurality of oligonucleotides, wherein the annealing of the primer to the first and second plurality of support-bound oligonucleotides serves as a primer for extension of the first and second plurality of complementary oligonucleotides, thereby producing a first and second plurality of extension product duplexes; c) removing the primer sequences from the extension product duplexes; d) dissociating the extension product duplexes, thereby producing a first and second plurality of complementary oligonucleotides; e) hybridizing the first plurality of complementary oligonucleotides to the third plurality of oligonucleotides; and f) hybridizing the second plurality of complementary oligonucleotides to the first plurality of oligonucleotides, thereby producing the polynucleotide. In some embodiments, the method further provides a fourth plurality of support-bound single-stranded oligonucleotides wherein each fourth plurality of oligonucleotides has a predefined sequence and is bound to a fourth discrete feature of the support, each fourth plurality of oligonucleotides comprising a primer binding site at its 3' end that is complementary to a primer sequence and a sequence region that is complementary to a 5' end of the polynucleotide, and repeating steps b) through f) thereby producing a longer polynucleotide. In some embodiments, the primers hybridizing to the first and second plurality of oligonucleotides are the same. The primers may comprise at least one Uracil and the primer is removed using a mixture of Uracil DNA glycosylase (UDG) and the DNA glycosylase-lyase Endonuclease VIII.

In some embodiments, the method for producing at least one double-stranded polynucleotide having a predefined sequence comprises the following steps: a) providing at least a first and a second plurality of support-bound single-stranded oligonucleotides, each first and second plurality of oligonucleotides having a predefined sequence and being bound to a first and second discrete feature of the support, each first plurality of oligonucleotides comprising a primer binding site at its 3' end which is complementary to a primer sequence, a first sequence region at the 5' end of the primer binding site and a second 3' end sequence region and wherein the second plurality of oligonucleotides comprises a sequence region at its 5' end that is identical to the first sequence region of the first plurality of oligonucleotides; b) annealing the primer to the primer binding sites of the first plurality of oligonucleotides at the first feature, wherein the annealing of the primer to the first plurality of support-bound oligonucleotides serves as a primer for extension of the first plurality of complementary oligonucleotides, thereby producing a first plurality of extension product duplexes; c) removing the primer sequences from the extension product duplexes; d) dissociating the extension product duplexes, thereby producing a first plurality of complementary oligonucleotides; e) hybridizing the first plurality of complementary oligonucleotides to the second plurality of oligonucleotides at the second feature; f) providing a stem-loop oligonucleotide, wherein the 3' end of the stem structure is complementary to the 3' end of the extension product; g) hybridizing the stem-loop oligonucleotide to the first plurality of oligonucleotides at the second feature; and h) ligating the stem-loop oligonucleotide to the first extension product, thereby generating the double-stranded stem and loop polynucleotide. In some embodiments, the method further comprises a) providing at least a third and a fourth plurality of support-bound single-stranded oligonucleotides, each third and fourth plurality of oligonucleotides having a predefined sequence and being bound to a third and fourth discrete feature of the support, each third plurality of oligonucleotides comprising a primer binding site at its 3' end which is complementary to a primer sequence, a first sequence region at the 5' end of the primer binding site, the first region sequence being substantially identical to the 5' end of the double-stranded stem-loop polynucleotide and a second 3' end sequence region, wherein the fourth plurality of oligonucleotides comprises a sequence region at its 5' end which is substantially identical to the first sequence region of the third plurality of oligonucleotides; b) annealing the primer to the primer binding sites of the third plurality of oligonucleotides at the third feature, wherein the annealing of the primer to the third plurality of support-bound oligonucleotides serves as a primer for extension of the third plurality of complementary oligonucleotides, thereby producing a third plurality of extension product duplexes; c) removing the primer sequences from the extension product duplexes; d) dissociating the extension product duplexes, thereby producing a third plurality of complementary oligonucleotides; e) hybridizing the third plurality of complementary oligonucleotides to the fourth plurality of oligonucleotides at the fourth feature; f) dissociating the double-stranded stem-loop polynucleotide from the second feature; g) transferring the stem-loop polynucleotide to the fourth feature; h) hybridizing the stem-loop polynucleotide to the fourth plurality of oligonucleotides at the fourth feature, thereby extending the stem-loop polynucleotide; and h) ligating the 3' end of the stem-loop polynucleotide with the 5' end of the third plurality of oligonucleotides, thereby forming a longer double-stranded polynucleotide. In some embodiments, steps a) through h) may be repeated to produce a longer polynucleotide. In some embodiments, the primers hybridizing to the first and second plurality of oligonucleotides are the same. The primers may comprise at least one Uracil and the primer is removed using a mixture of Uracil DNA glycosylase (UDG) and the DNA glycosylase-lyase Endonuclease VIII.

In some embodiments, the method for producing at least one double-stranded polynucleotide having a predefined sequence comprises a) synthesizing a polynucleotide at a first discrete feature; b) synthesizing a complementary oligonucleotide at a second discrete feature, wherein the 3' terminal region of the complementary oligonucleotide is complementary to the 5' terminal region of the polynucleotide; c) transferring the complementary oligonucleotide to the first feature; and d) hybridizing the complementary oligonucleotide to the polynucleotide.

BRIEF DESCRIPTION OF THE FIGURES

FIG. 1 illustrates an exemplary method of for the elongation of polynucleotides on a solid support using repeated polymerase extension reactions.

DETAILED DESCRIPTION OF THE INVENTION

Figure 2A:
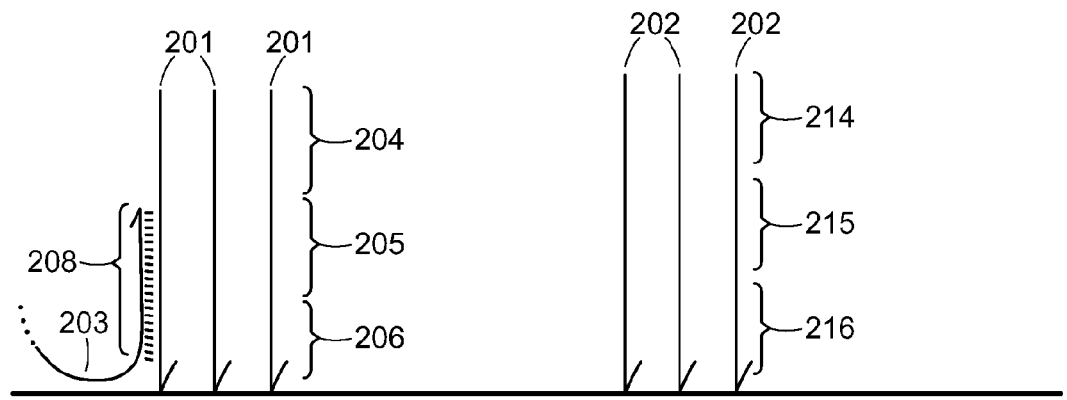
FIG. 2 illustrates a non-limiting example screening of extension junctions formed during the (n−1) and (n−2) extensions steps.

Aspects of the technology provided herein are useful for increasing the accuracy, yield, throughput, and/or cost efficiency of nucleic acid synthesis and assembly reactions. As used herein the terms "nucleic acid", "polynucleotide", "oligonucleotide" are used interchangeably and refer to naturally-occurring or synthetic polymeric forms of nucleotides. The oligonucleotides and nucleic acid molecules of the present invention may be formed from naturally occurring nucleotides, for example forming deoxyribonucleic acid (DNA) or ribonucleic acid (RNA) molecules. Alternatively, the naturally occurring oligonucleotides may include structural modifications to alter their properties, such as in peptide nucleic acids (PNA) or in locked nucleic acids (LNA). The solid phase synthesis of oligonucleotides and nucleic acid molecules with naturally occurring or artificial bases is well known in the art. The terms should be understood to include equivalents, analogs of either RNA or DNA made from nucleotide analogs and as applicable to the embodiment being described, single-stranded or double-stranded polynucleotides. Nucleotides useful in the invention include, for example, naturally-occurring nucleotides (for example, ribonucleotides or deoxyribonucleotides), or natural or synthetic modifications of nucleotides, or artificial bases. As used herein, the term monomer refers to a member of a set of small molecules which are and can be joined together to from an oligomer, a polymer or a compound composed of two or more members. The particular ordering of monomers within a polymer is referred to herein as the "sequence" of the polymer. The set of monomers includes but is not limited to example, the set of common L-amino acids, the set of D-amino acids, the set of synthetic and/or natural amino acids, the set of nucleotides and the set of pentoses and hexoses. Aspects of the invention described herein primarily with regard to the preparation of oligonucleotides, but could readily be applied in the preparation of other polymers such as peptides or polypeptides, polysaccharides, phospholipids, heteropolymers, polyesters, polycarbonates, polyureas, polyamides, polyethyleneimines, polyarylene sulfides, polysiloxanes, polyimides, polyacetates, or any other polymers.

As used herein, the term "predetermined sequence" means that the sequence of the polymer is known and chosen before synthesis or assembly of the polymer. In particular, aspects of the invention is described herein primarily with regard to the preparation of nucleic acids molecules, the sequence of the oligonucleotide or polynucleotide being known and chosen before the synthesis or assembly of the nucleic acid molecules. In some embodiments of the technology provided herein, immobilized oligonucleotides or polynucleotides are used as a source of material. In various embodiments, the methods described herein use pluralities of oligonucleotides, each sequence being determined based on the sequence of the final polynucleotides constructs to be synthesized. In one embodiment, oligonucleotides are short nucleic acid molecules. For example, oligonucleotides may be from 10 to about 300 nucleotides, from 20 to about 400 nucleotides, from 30 to about 500 nucleotides, from 40 to about 600 nucleotides, or more than about 600 nucleotides long. However, shorter or longer oligonucleotides may be used. Oligonucleotides may be designed to have different length. In some embodiments, the sequence of the polynucleotide construct may be divided up into a plurality of shorter sequences that can be synthesized in parallel and assembled into a single or a plurality of desired polynucleotide constructs using the methods described herein.

In some embodiments, the assembly procedure may include several parallel and/or sequential reaction steps in which a plurality of different nucleic acids or oligonucleotides are synthesized or immobilized, primer-extended, and are combined in order to be assembled (e.g., by extension or ligation as described herein) to generate a longer nucleic acid product to be used for further assembly, cloning, or other applications (see U.S. provisional application 61/235,677 and PCT application PCT/US09/55267 which are incorporate herein by reference in their entirety).

In some embodiments, methods of assembling libraries containing nucleic acids having predetermined sequence variations are provided herein. Assembly strategies provided herein can be used to generate very large libraries representative of many different nucleic acid sequences of interest. In some embodiments, libraries of nucleic acid are libraries of sequence variants. Sequence variants may be variants of a single naturally-occurring protein encoding sequence. However, in some embodiments, sequence variants may be variants of a plurality of different protein-encoding sequences. Accordingly, one aspect of the technology provided herein relates to the design of assembly strategies for preparing precise high-density nucleic acid libraries. Another aspect of the technology provided herein relates to assembling precise high-density nucleic acid libraries. Aspects of the technology provided herein also provide precise high-density nucleic acid libraries. A high-density nucleic acid library may include more that 100 different sequence variants (e.g., about $10^2$ to $10^3$; about $10^3$ to $10^4$; about $10^4$ to $10^5$; about $10^5$ to $10^6$; about $10^6$ to $10^7$; about $10^7$ to $10^8$; about $10^8$ to $10^9$; about $10^9$ to $10^{10}$; about $10^{10}$ to $10^{11}$; about $10^{11}$ to $10^{12}$; about $10^{12}$ to $10^{13}$; about $10^{13}$ to $10^{14}$; about $10^{14}$ to $10^{15}$; or more different sequences) wherein a high percentage of the different sequences are specified sequences as opposed to random sequences (e.g., more than about 50%, more than about 60%, more than about 70%, more than about 75%, more than about 80%, more than about 85%, more than about 90%, about 91%, about 92%, about 93%, about 94%, about 95%, about 96%, about 97%, about 98%, about 99%, or more of the sequences are predetermined sequences of interest).

In some embodiments, the methods and apparatus provided herein use oligonucleotides that are immobilized on a surface or substrate (e.g., support-bound oligonucleotides). As used herein the term "support" and "substrate" are used interchangeably and refers to a porous or non-porous solvent insoluble material on which polymers such as nucleic acids are synthesized or immobilized. As used herein "porous" means that the material contains pores having substantially uniform diameters (for example in the nm range). Porous materials include paper, synthetic filters etc. In such porous materials, the reaction may take place within the pores. The support can have any one of a number of shapes, such as pin, strip, plate, disk, rod, bends, cylindrical structure, particle, including bead, nanoparticles and the like. The support can have variable widths. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly (4-methylbutene), polystyrene, polymethacrylate, poly(ethylene terephthalate), nylon, poly(vinyl butyrate), polyvinylidene difluoride (PVDF) membrane, glass, controlled pore glass, magnetic controlled pore glass, ceramics, metals, and the like etc.; either used by themselves or in conjunction with other materials. In some embodiments, oligonucleotides are synthesized on an array format. For example, single-stranded oligonucleotides are synthesized in situ on a common support wherein each oligonucleotide is synthesized on a separate or discrete feature (or spot) on the substrate. In preferred embodiments, single stranded oligonucleotides are bound to the surface of the support or feature. As used herein the term "array" refers to an arrangement of discrete features for storing, routing, amplifying and releasing oligonucleotides or complementary oligonucleotides for further reactions. In a preferred embodiment, the support or array is addressable: the support includes two or more discrete addressable features at a particular predetermined location (i.e., an "address") on the support. Therefore, each oligonucleotide molecule of the array is localized to a known and defined location on the support. The sequence of each oligonucleotide can be determined from its position on the support. Moreover, addressable supports or arrays enable the direct control of individual isolated volumes such as droplets. In some embodiments, the size of the defined feature is chosen to allow formation of a microvolume droplet on the feature, each droplet being kept separate from each other. As described herein, features are typically, but need not be, separated by interfeature spaces to ensure that droplets between two adjacent features do not merge. Interfeatures will typically not carry any oligonucleotide on their surface and will correspond to inert space. In some embodiments, features and interfeatures may differ in their hydrophilicity or hydrophobicity properties. In some embodiments, features and interfeatures may comprise a modifier as described herein.

In some embodiments, oligonucleotides are attached, spotted, immobilized, surface-bound, supported or synthesized on the discrete features of the surface or array. Oligonucleotides may be covalently attached to the surface or deposited on the surface. Arrays may be constructed, custom ordered or purchased from a commercial vendor (e.g., Agilent, Affymetrix, Nimblegen). Various methods of construction are well known in the art e.g., maskless array synthesizers, light directed methods utilizing masks, flow channel methods, spotting methods etc. In some embodiments, construction and/or selection oligonucleotides may be synthesized on a solid support using maskless array synthesizer (MAS). Maskless array synthesizers are described, for example, in PCT application No. WO 99/42813 and in corresponding U.S. Pat. No. 6,375,903. Other examples are known of maskless instruments which can fabricate a custom DNA microarray in which each of the features in the array has a single-stranded DNA molecule of desired sequence. Other methods for synthesizing construction and/or selection oligonucleotides include, for example, light-directed methods utilizing masks, flow channel methods, spotting methods, pin-based methods, and methods utilizing multiple supports. Light directed methods utilizing masks (e.g., VLSIPS™ methods) for the synthesis of oligonucleotides is described, for example, in U.S. Pat. Nos. 5,143,854, 5,510,270 and 5,527,681. These methods involve activating predefined regions of a solid support and then contacting the support with a preselected monomer solution. Selected regions can be activated by irradiation with a light source through a mask much in the manner of photolithography techniques used in integrated circuit fabrication. Other regions of the support remain inactive because illumination is blocked by the mask and they remain chemically protected. Thus, a light pattern defines which regions of the support react with a given monomer. By repeatedly activating different sets of predefined regions and contacting different monomer solutions with the support, a diverse array of polymers is produced on the support. Other steps, such as washing unreacted monomer solution from the support, can be optionally used. Other applicable methods include mechanical techniques such as those described in U.S. Pat. No. 5,384,261. Additional methods applicable to synthesis of construction and/or selection oligonucleotides on a single support are described, for example, in U.S. Pat. No. 5,384,261. For example, reagents may be delivered to the support by either (1) flowing within a channel defined on predefined regions or (2) "spotting" on predefined regions. Other approaches, as well as combinations of spotting and flowing, may be employed as well. In each instance, certain activated regions of the support are mechanically separated from other regions when the monomer solutions are delivered to the various reaction sites. Flow channel methods involve, for example, microfluidic systems to control synthesis of oligonucleotides on a solid support. For example, diverse polymer sequences may be synthesized at selected regions of a solid support by forming flow channels on a surface of the support through which appropriate reagents flow or in which appropriate reagents are placed. Spotting methods for preparation of oligonucleotides on a solid support involve delivering reactants in relatively small quantities by directly depositing them in selected regions. In some steps, the entire support surface can be sprayed or otherwise coated with a solution, if it is more efficient to do so. Precisely measured aliquots of monomer solutions may be deposited dropwise by a dispenser that moves from region to region. Pin-based methods for synthesis of oligonucleotides on a solid support are described, for example, in U.S. Pat. No. 5,288,514. Pin-based methods utilize a support having a plurality of pins or other extensions. The pins are each inserted simultaneously into individual reagent containers in a tray. An array of 96 pins is commonly utilized with a 96-container tray, such as a 96-well microtiter dish. Each tray is filled with a particular reagent for coupling in a particular chemical reaction on an individual pin. Accordingly, the trays will often contain different reagents. Since the chemical reactions have been optimized such that each of the reactions can be performed under a relatively similar set of reaction conditions, it becomes possible to conduct multiple chemical coupling steps simultaneously.

In another embodiment, a plurality of oligonucleotides may be synthesized on multiple supports. One example is a bead based synthesis method which is described, for example, in U.S. Pat. Nos. 5,770,358; 5,639,603; and 5,541,061. For the synthesis of molecules such as oligonucleotides on beads, a large plurality of beads is suspended in a suitable carrier (such as water) in a container. The beads are provided with optional spacer molecules having an active site to which is complexed, optionally, a protecting group. At each step of the synthesis, the beads are divided for coupling into a plurality of containers. After the nascent oligonucleotide chains are deprotected, a different monomer solution is added to each container, so that on all beads in a given container, the same nucleotide addition reaction occurs. The beads are then washed of excess reagents, pooled in a single container, mixed and re-distributed into another plurality of containers in preparation for the next round of synthesis. It should be noted that by virtue of the large number of beads utilized at the outset, there will similarly be a large number of beads randomly dispersed in the container, each having a unique oligonucleotide sequence synthesized on a surface thereof after numerous rounds of randomized addition of bases. An individual bead may be tagged with a sequence which is unique to the double-stranded oligonucleotide thereon, to allow for identification during use.

Pre-synthesized oligonucleotide and/or polynucleotide sequences may be attached to a support or synthesized in situ using light-directed methods, flow channel and spotting methods, inkjet methods, pin-based methods and bead-based methods set forth in the following references: McGall et al. (1996) Proc. Natl. Acad. Sci. U.S.A. 93:13555; Synthetic DNA Arrays In Genetic Engineering, Vol. 20:111, Plenum Press (1998); Duggan et al. (1999) Nat. Genet. S21:10; Microarrays: Making Them and Using Them In Microarray Bioinformatics, Cambridge University Press, 2003; U.S. Patent Application Publication Nos. 2003/0068633 and 2002/0081582; U.S. Pat. Nos. 6,833,450, 6,830,890, 6,824,866, 6,800,439, 6,375,903 and 5,700,637; and PCT Publication Nos. WO 04/031399, WO 04/031351, WO 04/029586, WO 03/100012, WO 03/066212, WO 03/065038, WO 03/064699, WO 03/064027, WO 03/064026, WO 03/046223, WO 03/040410 and WO 02/24597; the disclosures of which are incorporated herein by reference in their entirety for all purposes. In some embodiments, pre-synthesized oligonucleotides are attached to a support or are synthesized using a spotting methodology wherein monomers solutions are deposited dropwise by a dispenser that moves from region to region (e.g., ink jet). In some embodiments, oligonucleotides are spotted on a support using, for example, a mechanical wave actuated dispenser.

Some aspects of the invention relate to a polynucleotide assembly process wherein synthetic oligonucleotides are designed and used as templates for primer extension reactions and to assemble polynucleotides into longer polynucleotides constructs. During enzymatic amplification or chain extension reactions, the error in sequence is faithfully replicated. As a result, polynucleotides population synthesized by this method contains both error-free and error-prone sequences. In some embodiments, since synthetic oligonucleotides can contain incorrect sequences due to errors introduced during oligonucleotide synthesis, it can be useful to remove polynucleotide that have incorporated one or more error-containing oligonucleotides during assembly or extension. In some embodiments, one or more assembled polynucleotides may be sequenced to determine whether they contain the predetermined sequence or not. This procedure allows fragments with the correct sequence to be identified. In other embodiments, other techniques may be used to remove error containing nucleic acid fragments. Such nucleic acid fragments can be nascently synthesized oligonucleotides or assembled nucleic acid polymers. It should be appreciated that error containing-nucleic acids can be double-stranded homoduplexes having the error on both strands (i.e., incorrect complementary nucleotide(s), deletion(s), or addition(s) on both strands), because the assembly procedure may involve one or more rounds of polymerase extension (e.g., during assembly or after assembly to amplify the assembled product). During polymerase extension, the input nucleic acid containing an error may serve as a template thereby producing a complementary strand comprising the complementary error. In certain embodiments, a preparation of double-stranded nucleic acid fragments or duplexes may be suspected to contain a mixture of nucleic acids having the correct predefined sequence as well as nucleic acids containing one or more sequence errors incorporated during assembly. The term "duplex" refers to a nucleic acid molecule that is at least partially double-stranded. A "stable duplex" refers to a duplex that is relatively more likely to remain hybridized to a complementary sequence under a given set of hybridization conditions. In an exemplary embodiment, a stable duplex refers to a duplex that does not contain a basepair mismatch, insertion, or deletion. An "unstable duplex" refers to a duplex that is relatively less likely to remain hybridized to a complementary sequence under a given set of hybridization conditions such as stringent melt. In an exemplary embodiment, an unstable duplex refers to a duplex that contains at least one basepair mismatch, insertion, or deletion. As used herein the term "stringency" is used in reference to the conditions of temperature, ionic strength, and the presence of other compounds such as organic solvents, under which nucleic acid hybridizations are conducted. Hybridization stringency increases with temperature and/or the solution chemical properties such as the amounts of salts and/or formamide in the hybridization solution during a hybridization process. With "high stringency" conditions, nucleic acid base pairing will occur only between nucleic acid fragments that have a high frequency of complementary base sequences. Stringent conditions may be selected to be about 5° C. lower than the thermal melting point (Tm) for a given polynucleotide duplex at a defined ionic strength and pH. The length of the complementary polynucleotide strands and the GC content determine the Tm of the duplex, and thus the hybridization conditions necessary for obtaining a desired specificity of hybridization. The Tm is the temperature (under defined ionic strength and pH) at which 50% of a polynucleotide sequence hybridizes to a perfectly matched complementary strand. In certain cases it may be desirable to increase the stringency of the hybridization conditions to be about equal to the Tm for a particular duplex. Appropriate stringency conditions are known to those skilled in the art or may be determined experimentally by the skilled artisan. See, for example, Current Protocols in Molecular Biology, John Wiley & Sons, N.Y. (1989), 6.3.1-12.3.6; Sambrook et al., 1989, Molecular Cloning, A Laboratory Manual, Cold Spring Harbor Press, N.Y.; S. Agrawal (ed.) Methods in Molecular Biology, volume 20; Tijssen (1993) Laboratory Techniques in biochemistry and molecular biology-hybridization with nucleic acid probes, e.g., part I chapter 2 "Overview of principles of hybridization and the strategy of nucleic acid probe assays", Elsevier, N.Y.

In some embodiments, sequence errors may be removed using a technique that involves denaturing and reannealing the double-stranded nucleic acids. In some embodiments, single strands of nucleic acids that contain complementary errors may be unlikely to reanneal together if nucleic acids containing each individual error are present in the nucleic acid preparation at a lower frequency than nucleic acids having the correct sequence at the same position. Rather, error containing single strands can reanneal with error-free complementary strand or complementary strands containing one or more different errors or error at different location. As a result, error-containing strands can end up in the form of heteroduplex molecules in the reannealed reaction product. Nucleic acid strands that are error-free may reanneal with error-containing strands or with other error-free strands. Reannealed error-free strands form homoduplexes in the reannealed sample. Accordingly, by removing heteroduplex molecules from the reannealed preparation of nucleic acid fragments, the amount or frequency of error containing nucleic acids can be reduced.

Heteroduplex formation thus takes place through a process that can be understood as shuffling, by which nucleic acid strands from different populations can be hybridized with one another so that perfect match and mismatch-containing duplexes can be formed. Suitable method for removing heteroduplex molecules include chromatography, electrophoresis, selective binding of heteroduplex molecules that binds preferentially to double stranded DNA having a sequence mismatch between the two strands. The term "mismatch" or "base pair mismatch" indicates a base pair combination that generally does not form in nucleic acids according to Watson and Crick base pairing rules. For example, when dealing with the bases commonly found in DNA, namely adenine, guanine, cytosine and thymidine, base pair mismatches are those base combinations other than the A-T and G-C pairs normally found in DNA. As described herein, a mismatch may be indicated, for example as C/C meaning that a cytosine residue is found opposite another cytosine, as opposed to the proper pairing partner, guanine.

In one aspect, the invention relates to a method for producing high fidelity polynucleotides on a solid support. The synthetic polynucleotides are at least about 1, 2, 3, 4, 5, 8, 10, 15, 20, 25, 30, 40, 50, 75, or 100 kilobases (kb), or 1 megabase (mb), or longer. In exemplary embodiments, a compositions of synthetic polynucleotides contains at least about 1%, 2%, 3%, 4%, 5%, 6%, 7%, 8%, 9%, 10%, 15%, 20%, 25%, 50%, 60%, 70%, 80%, 90%, 95% or more, copies that are error free (e.g., having a sequence that does not deviate from a predetermined sequence). The percent of error free copies is based on the number of error free copies in the compositions as compared to the total number of copies of the polynucleotide in the composition that were intended to have the correct, e.g., predefined or predetermined, sequence.

Some aspects the invention relate to the design of oligonucleotides for the high fidelity polynucleotide assembly. Aspects of the invention may be useful to increase the throughput rate of a nucleic acid assembly procedure and/or reduce the number of steps or amounts of reagent used to generate a correctly assembled nucleic acid. In certain embodiments, aspects of the invention may be useful in the context of automated nucleic acid assembly to reduce the time, number of steps, amount of reagents, and other factors required for the assembly of each correct nucleic acid. Accordingly, these and other aspects of the invention may be useful to reduce the cost and time of one or more nucleic acid assembly procedures.

In some embodiments, the method includes synthesizing a plurality of oligonucleotides or polynucleotides in a chain extension reaction using a first plurality of single stranded oligonucleotides as templates. As noted above, the oligonucleotides may be first synthesized onto a plurality of discrete features of the surface, or may be deposited on the plurality of features of the support. In a preferred embodiment, the oligonucleotides are covalently attached to the support. In preferred embodiments, the first plurality of oligonucleotides is immobilized to a solid surface. In a preferred embodiment, each feature of the solid surface comprises a high density of oligonucleotides having a different predetermined sequence (e.g., approximately $10^6$-$10^8$ molecules per feature). The support may comprise at least 100, at least 1,000, at least $10^4$, at least $10^5$, at least $10^6$, at least $10^7$, at least $10^8$ features.

In certain embodiments, pluralities of single-stranded oligonucleotides may be designed to have a sequence that is identical or complementary to a different portion of the sequence of a predetermined target polynucleotide that is to be assembled. Accordingly, in some embodiments each oligonucleotide may have a sequence that is identical or complementary to a portion of one of the two strands of a double-stranded target nucleic acid. In some embodiments, pluralities of different single-stranded oligonucleotides are immobilized at different features of a solid support. In some embodiments, the oligonucleotides may be attached through their 5' end. In other embodiments, the oligonucleotides may be attached through their 3' end. In some embodiments, the oligonucleotides are designed such as each plurality of oligonucleotides comprising a sequence region at its 5' end that is the same as a sequence region of the 3' end of another oligonucleotide and a sequence region at its 3' end that is the same as a sequence region at a 5' end of a different oligonucleotide. It should be appreciated that by 3' end, it is meant the sequence downstream to the 5' end and by 5' end it is meant the sequence upstream to the 3' end. For example, an oligonucleotide may be immobilized on the support via a nucleotide sequence, linker or spacer that is not involved in hybridization. The 3' end sequence of the support-bound oligonucleotide referred then to a sequence upstream to the linker or spacer. In some embodiments, the first plurality of oligonucleotides has a 3' end that is complementary to the 3' end of an input single-stranded oligonucleotide. In some embodiments, if the assembly of the target polynucleotide required N extension cycles, 1 to N pluralities of different support-bound single stranded oligonucleotides are designed such as the first plurality of oligonucleotide comprises at its 5' end sequence region that is the same as a sequence region at the 3' end of a second oligonucleotide in the composition and wherein a N plurality of oligonucleotide comprises at its 3' end a sequence region that is the same as a sequence region of the (N−1) oligonucleotide.

It should be appreciated that different oligonucleotides may be designed to have different lengths. In some embodiments, one or more different oligonucleotides may have overlapping sequence regions (e.g., overlapping 5' regions or overlapping 3' regions). Overlapping sequence regions may be identical (i.e., corresponding to the same strand of the nucleic acid fragment) or complementary (i.e., corresponding to complementary strands of the nucleic acid fragment). Overlapping sequences may be of any suitable length. Overlapping sequences may be between about 5 and about 500 nucleotides long (e.g., between about 10 and 100, between about 10 and 75, between about 10 and 50, about 20, about 25, about 30, about 35, about 40, about 45, about 50, etc.) However, shorter, longer or intermediate overlapping lengths may be used. It should be appreciated that overlaps between different input nucleic acids used in an assembly reaction may have different lengths. In some embodiments, immobilized oligonucleotides include sequence regions having overlapping regions to assist in the assembly of a predetermined nucleic acid sequence. In a preferred embodiment, immobilized oligonucleotides include sequence regions having complementary regions for hybridization to a different oligonucleotide or to a polynucleotide. The complementary regions refer to a sequence region at either a 3' end or a 5' end of the immobilized template oligonucleotide. In a preferred embodiment, the complementary region is localized at the 3' end of the immobilized oligonucleotides. Complementary regions refer to a 3' end or a 5' end region of a first oligonucleotide or polynucleotide that is capable of hybridizing to a 5' end or 3' end of a second oligonucleotide or polynucleotide.

FIG. 1 shows an exemplary method for producing polynucleotide on a substrate or solid support. The method comprises several repeated steps of annealing, extension and melting on different features (102, 103, 104, 105) of the solid support (FIG. 1A-1F). In some embodiments, each feature of the solid support comprises a plurality of oligonucleotides having a predefined sequence. For example, referring to FIG. 1A, feature 102 comprises a plurality of molecules (106) having a predefined sequence. In some embodiments, the plurality of molecules having predefined sequences formed the final polynucleotide products. Yet in other embodiment, the plurality molecules having a predefined sequence partially comprise a sequence of the final product. In some embodiments, a population of free (i.e., non-immobilized) input polynucleotides (element 101, FIG. 1A) is added to a first feature of the solid support (for example feature 102, FIG. 1A). In a preferred embodiment, the input polynucleotides are single-stranded polynucleotides (single-stranded DNA, for example). The input polynucleotide may be a synthetic oligonucleotide that is synthesized or obtained from a commercial supplier. In some embodiments, one or more input nucleic acids may be amplification products (e.g., PCR products), restriction fragments, or other suitable nucleic acid molecules. In some embodiments, the first plurality of oligonucleotides is designed to have a 3' sequence that is complementary to the 3' end of the input polynucleotide. Yet, in other embodiments, the input polynucleotide sequence of (101) is designed such that the 3' a terminal sequence (107) hybridizes to a region (157) of the oligonucleotide sequence (106) (FIG. 1B). In a first step, the polynucleotide sequence (101) is partially hybridized to the support-bound oligonucleotide, the hybridized region being formed between the (107) region of the polynucleotide and the (157) region of the immobilized oligonucleotide as shown in FIG. 1B. In a second step, polymerase-mediated extension of the hybridized polynucleotides results in a template-based extension of the 3' ends of polynucleotides that have annealed to the 3' regions of the template oligonucleotides generating extended polynucleotides containing sequences that are complementary to a sequence region of the template oligonucleotide. Referring to FIG. 1C, the polynucleotide (101) is extended in the presence of an appropriate polymerase enzyme and other appropriate components (such as dNTPs, salt, buffer, and etc.) into a longer polynucleotide (110) that includes sequence (108) complementary to sequence (158) of the template oligonucleotide (106). The resulting molecule (110), now elongated by the length of sequence complementary to sequence (158) is composed of the sequences of (101) and (108). In a third step, the extension product (110) is melted from oligonucleotide (106) and released into solution (FIG. 1D). For example, the input polynucleotide can then be transferred to a different feature of the support. The input polynucleotide can be transferred or moved mechanically (e.g. pipetting) or using electric, electrostatic, electromagnetic forces. The input polynucleotide (110) can then partially anneal due to the complementary sequence region between polynucleotide (110) and oligonucleotide (111) immobilized on a different feature of the solid support (for example (111), feature (103) of the solid support (100), FIG. 1E) The annealing of input polynucleotide (110) to oligonucleotide (111), followed by its extension as described above, leads to a longer polynucleotide (120) comprising sequences of polynucleotide (101) and complementary sequences of oligonucleotides (106), and (111). At region (103), the population of molecules (intended to be identical to 111) is designed with a sequence region (167) that hybridizes to sequence region (108) of polynucleotide (110), forming a hybridized region (112) composed of the sequences of (108) and (167). The addition of a polymerase with other appropriate components (such as dNTP, salt, buffer, and etc.) allows for the extension of polynucleotide (110) to include sequence (113) using sequence region (168) as template. The resulting molecule (120), now elongated by the length of sequence complementary to sequence (168) and is composed of the sequences of (101), (108), and (113). The molecule can be melted from oligonucleotide (111) and released into solution, allowing it to hybridize to a different region (104) of the surface (100) (FIG. 1E). This process can be repeated to allow the elongation of polynucleotide (120) to include sequence region (123) at region (104) and at region (133) from region (105), resulting in sequence (140) (FIG. 1F). These cycles of melting, transferring, annealing and extension may be repeated until the target full length polynucleotide having a predetermined sequence is synthesized, each cycle of polymerase extension extending oligonucleotide pairs with annealed 3' regions. In each cycle, extension results in the addition of sequences complementary to the template oligonucleotide. Each cycle may include a denaturing, transferring, annealing and extension step. In some embodiments, the extension may occur under the annealing conditions. Accordingly, in one embodiment, cycles of extension may be obtained by alternating between denaturing conditions (e.g., a denaturing temperature) and annealing/extension conditions (e.g., an annealing/extension temperature). However, in other embodiments, progressive extension may be achieved without temperature cycling. For example, an enzyme capable promoting rolling circle amplification may be used (e.g., TempliPhi). It should be appreciated that several cycles of polymerase extension may be required to assemble a single target polynucleotide containing the sequences of an initial plurality of template oligonucleotides. In some embodiments, the process can be carried out for M steps, where M can be greater than 1, greater than 10, greater than 100, greater than 1,000, greater than 10,000, greater than 100,000. In some embodiments, the number of cycles is equal or superior to the number of immobilized oligonucleotides. A full length product (or predetermined target polynucleotide sequence) may be isolated or purified using a size selection, cloning, selective binding or other suitable purification procedure. In addition, the full length product may be amplified using appropriate 5' and 3' amplification primers.

Polymerase-based assembly techniques may involve one or more suitable polymerase enzymes that can catalyze a template-based extension of a nucleic acid in a 5' to 3' direction in the presence of suitable nucleotides and an annealed template. A polymerase may be thermostable. A polymerase may be obtained from recombinant or natural sources. In some embodiments, a thermostable polymerase from a thermophilic organism may be used. In some embodiments, a polymerase may include a 3'→5' exonuclease/proofreading activity. In some embodiments, a polymerase may have no, or little, proofreading activity (e.g., a polymerase may be a recombinant variant of a natural polymerase that has been modified to reduce its proofreading activity). Examples of thermostable DNA polymerases include, but are not limited to: Taq (a heat-stable DNA polymerase from the bacterium *Thermus aquaticus*); Pfu (a thermophilic DNA polymerase with a 3'→5' exonuclease/proofreading activity from *Pyrococcus furiosus*, available from for example Promega); VentR® DNA Polymerase and VentRO (exo-) DNA Polymerase (thermophilic DNA polymerases with or without a 3'→5' exonuclease/proofreading activity from *Thermococcus litoralis*; also known as Th polymerase); Deep VentR® DNA Polymerase and Deep VentR® (exo-) DNA Polymerase (thermophilic DNA polymerases with or without a 3'→5' exonuclease/proofreading activity from *Pyrococcus* species GB-D; available from New England Biolabs); KOD HiFi (a recombinant *Thermococcus* kodakaraensis KODI DNA polymerase with a 3'→5' exonuclease/proofreading activity, available from Novagen,); BIO-X-ACT (a mix of polymerases that possesses 5'-3' DNA polymerase activity and 3'→5' proofreading activity); Klenow Fragment (an N-terminal truncation of *E. coli* DNA Polymerase I which retains polymerase activity, but has lost the 5'4 3' exonuclease activity, available from, for example, Promega and NEB); Sequenase™ (T7 DNA polymerase deficient in T-5' exonuclease activity); Phi29 (bacteriophage 29 DNA polymerase, may be used for rolling circle amplification, for example, in a TempliPhi™ DNA Sequencing Template Amplification Kit, available from Amersham Biosciences); TopoTaq (a hybrid polymerase that combines hyperstable DNA binding domains and the DNA unlinking activity of *Methanopyrus* topoisomerase, with no exonuclease activity, available from Fidelity Systems); TopoTaq HiFi which incorporates a proof-reading domain with exonuclease activity; Phusion™ (a Pyrococcus-like enzyme with a processivity-enhancing domain, available from New England Biolabs); any other suitable DNA polymerase, or any combination of two or more thereof. In some embodiments, the polymerase can be a SDP (strand-displacing polymerase; e.g., an SDPe—which is an SDP with no exonuclease activity). This allows isothermal PCR (isothermal extension, isothermal amplification) at a uniform temperature. As the polymerase (for example, Phi29, Bst) travels along a template it displaces the complementary strand (e.g., created in previous extension reactions). As the displaced DNAs are single-stranded, primers can bind at a consistent temperature, removing the need for any thermocycling during amplification.

Figure 4:
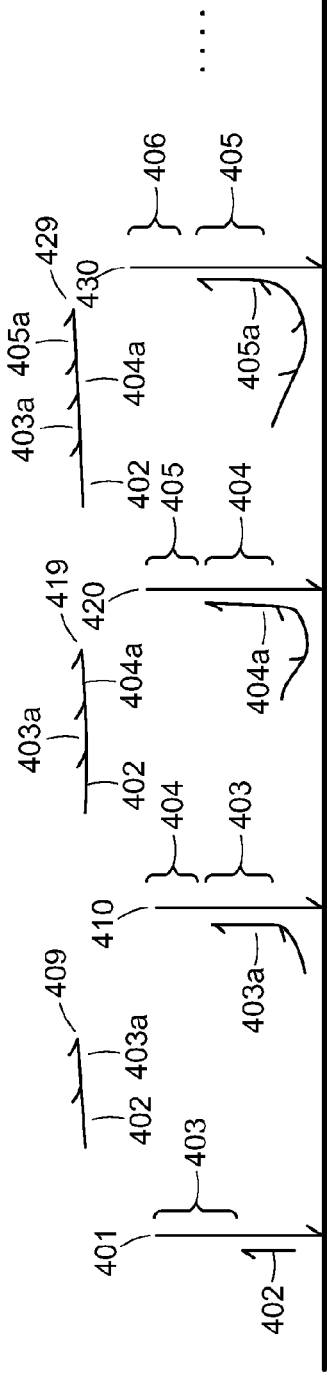
FIG. 4 illustrates a non-limiting exemplary method for polynucleotide extension and screening of error-containing polynucleotides.

In some embodiments, the first step of the extension reaction uses a primer (or seed primer). In some embodiments, the oligonucleotides may comprise universal (common to all oligonucleotides), semi-universal (common to at least of portion of the oligonucleotides) or individual or unique primer (specific to each oligonucleotide) binding sites on either the 5' end or the 3' end or both. As used herein, the term "universal" primer or primer binding site means that a sequence used to amplify the oligonucleotide is common to all oligonucleotides such that all such oligonucleotides can be amplified using a single set of universal primers. In other circumstances, an oligonucleotide contains a unique primer binding site. As used herein, the term "unique primer binding site" refers to a set of primer recognition sequences that selectively amplifies a subset of oligonucleotides. In yet other circumstances, an oligonucleotide contains both universal and unique amplification sequences, which can optionally be used sequentially. In a first step, a primer is added and anneals to an immobilized oligonucleotide. In some embodiments, the support bound or immobilized oligonucleotides comprise a primer binding site wherein the primer is complementary to the primer binding site. In the first step, a solution comprising a polymerase, at least one primer and dNTPs are added at a feature of the solid support under conditions promoting primer extension. Referring to FIG. 4, a seed primer (402) may be added at a feature comprising oligonucleotides (401). The seed primer hybridizes to the first extension region containing support-bound molecules (401). Under conditions promoting primer extension, the primer is extended into a product (409) using sequence (403) as a template.

One should appreciate that the extension reactions can take place in a single volume that encompasses all of the utilized features (102, 103, 104, 105, . . .), or each step can take place in a localized individual volume that contains only the region(s) of interest during a specific elongation step (see U.S. provisional application 61/235,677, U.S. provisional application 61/257,591 filed on Nov. 3, 2009, U.S. provisional applications 61/264,632 and 61/264,641, filed on Nov. 25, 2009, PCT applications PCT/US09/55267, PCT/US2010/055298, PCT/US2010/057392 which are incorporate herein by reference in their entirety). In some embodiments, it may be important to control the seed primer (or the first input polynucleotide) concentration to avoid unwanted extension reactions. When performing a plurality of extension reactions in a single volume (e.g. pooled extension), the extension product at step (n) may be melted off the surface-bond template, and is free to hybridize to any surface-bound extension template such as templates corresponding to extension steps (n), (n−1), (n−2), . . . all the way down to the first extension template. Indeed, the extension product having complementary sequence to all of the "prior-step" templates can result in side hybridizations and therefore thereby reducing the concentration of the polynucleotide of interest. In some embodiments, by increasing the concentration of the initial seed primer concentration it is possible to correct for the side reactions. In an exemplary embodiment if the support-bound templates have on average C number of oligonucleotides for each feature (i.e. each step of the extension), and M is the number of total extension steps, it is possible to introduce C*M number of seed molecules at the first step to correct for the side reactions.

In some embodiments, only a selected set of oligonucleotides suitable for hydration are hydrated while the remainder of the support remains dry. In one embodiment, each oligonucleotide has a predefined sequence different from the predefined sequence of the oligonucleotide bound to a different feature. In some embodiments, a set of predefined features may be selectively hydrated, thereby providing hydrated oligonucleotides. In another embodiment, the hydrated oligonucleotides are exposed to further processing within a droplet volume. For example, during the steps illustrated by FIGS. 1A, 1B and 1C, only region (102) may be covered by an isolated liquid volume or droplet, the droplet acting as a virtual reaction chamber. The liquid volume (or aqueous phase) may comprise water, buffer, primers, master mix, release chemicals, enzymes, or any combination thereof. For example the solution may be composed of oligonucleotides primer(s), nucleotides (dNTPs), buffer, polymerase and cofactors. In other embodiments, the solution is an alkaline denaturing solution. Yet, in other embodiments, the solution may comprise oligonucleotides such as complementary oligonucleotides or input polynucleotide. After melting of the extension product (110), the liquid volume or droplet is moved from region (102) to (103), carrying the melted extension products in solution to region (103). This process of moving the liquid volume can be repeated for each extension step of the process.

In some embodiments, a support is provided that comprises at least one feature having a plurality of surface-bound single-stranded oligonucleotides that are in a dry form and suitable for hydration. Each plurality of oligonucleotides is bound to a discrete feature of the support, and the predefined sequence of each plurality of oligonucleotides attached to the feature is different from the predefined sequence of the plurality of oligonucleotides attached to a different feature. At least one feature is hydrated thereby providing hydrated oligonucleotides within a droplet. At least one plurality of oligonucleotides is synthesized in a chain extension reaction on a first feature of the support by template-dependent synthesis. The products of chain extension are subjected to at least one round of denaturation and annealing. The support is then heated to a first melting temperature under stringent melt conditions thereby denaturing duplexes comprising error-containing oligonucleotides and releasing error-containing oligonucleotides in solution. Error-containing oligonucleotides are removed from the support. The steps can be repeated on at least one other feature and at least one different melting temperature. Error-free duplexes are denatured and error-free oligonucleotides are released in solution within a first stage droplet. A first droplet comprising a first plurality of substantially error-free oligonucleotides can then be combined to a second droplet comprising a second plurality of substantially error-free oligonucleotides, wherein a terminal region of the second plurality of oligonucleotides comprises sequences complementary to a terminal region of the first set of plurality of oligonucleotides. The first and second plurality of oligonucleotides can be contacted under conditions that allow one or more of annealing, chain extension, and denaturing. In some embodiments, the first and second droplets are combined by merging the droplets into a second stage droplet. First and/or second droplets can be moved from a first feature to a second feature of the support. In some embodiments, the surface is coated with a low melting-point substance for storage, for example wax, for storage. In some embodiments, the reactions are initiated by heating the surface above the low-melting point. Yet in other embodiments, the reactions are initiated by hydrating selected discrete features. In some embodiments, the support is a microfluidic device. Droplet movement may be controlled by the flow rates of the fluid in the device or by electrical, magnetic, mechanical action applied to the droplets. The droplets and/or the fluid within the microfluidic device can be transported and distributed by a variety of forces including electric forces, electrokinetic forces, pressure based flow techniques, capillary forces, thermo-capillary forces, gravitational and centrifugal forces, magnetic field, a mechanical force, including mechanical pressure waves such as sound waves or ultrasound, or an optical induced force or any combination thereof. One should appreciate that isolated volumes may be routed independently in a sequential or highly parallel fashion. Droplets may be routed using electrowetting-based techniques (see for example, U.S. Pat. No. 6,911,132 and U.S. Patent Application 2006/0054503). Electrowetting principle is based on manipulating droplets on a surface comprising an array of electrodes and using voltage to change the interfacial tension. In some embodiments, droplets are moved using a wettability gradient. It has been shown that droplets placed on wettability gradient surfaces typically move in the direction of increasing wettability (see Zielke and Szymczyk, Eur. Phys. J. Special Topics, 166, 155-158 (2009)). In other embodiments, droplets may be moved using a thermal gradient. When placed on a thermal gradient, droplets move from higher temperature locations towards lower temperature locations. Moving droplets using electrowetting, temperature gradients and wettability gradients depends on the liquid (e.g., aqueous, non-aqueous, solute concentration), the size of the droplets and/or the steepness of the gradient.

In some embodiments, the entire support or array containing the discrete features is subjected to thermocycling, annealing temperature conditions, stringent melt temperature conditions, or denaturing temperature conditions. Heating and cooling the support can be performed in any thermal cycle instrument. In other embodiments, one or more discrete features are subjected to specific temperature conditions (annealing, extension, wash or melt). Thermocycling of selected independent features (being separated from each others) can be performed by locally heating at least one discrete feature. Discrete features may be locally heated by any means known in the art. For example, the discrete features may be locally heated using a laser source of energy that can be controlled in a precise x-y dimension thereby individually modulating the temperature of a droplet. In another example, the combination of a broader beam laser with a mask can be used to irradiate specific features. In some embodiments, methods to control temperature on the support so that enzymatic reactions can take place on a support (PCR, ligation or any other temperature sensitive reaction) are provided. In some embodiments, a scanning laser is used to control the thermocycling on distinct features on the solid support. The wavelength used can be chosen from wide spectrum (100 nm to 100,000 nm, i.e., from ultraviolet to infrared). In some embodiments, the feature on which the droplet is spotted comprises an optical absorber or indicator. In some other embodiment, optical absorbent material can be added on the surface of the droplet. In some embodiments, the solid support is cooled by circulation of air or fluid. The energy to be deposited can be calculated based on the absorbance behavior. In some embodiments, the temperature of the droplet can be modeled using thermodynamics. The temperature can be measured by an LCD like material or any other in-situ technology. Yet in another embodiment, the whole support can be heated and cooled down to allow enzymatic reactions or other temperature sensitive reactions to take place. One method to control the temperature of the surface droplets is by using a scanning optical energy deposition setup. An energy source can be directed by a scanning setup to deposit energy at various locations on the surface of the solid support comprising support-bound molecules. Optical absorbent material can be added on the surface of the solid support or on the surface of droplet. Optical energy source, such as a high intensity lamp, laser, or other electromagnetic energy source (including microwave) can be used. The temperature of the different reaction sites can be controlled independently by controlling the energy deposited at each of the features.

For example, a Digital Micromirror Device (DMD) can be used for temperature control. DMD is an microfabricated spatial optical modulator. See, for example, U.S. Pat. No. 7,498,176. In some embodiments, a DMD can be used to precisely heat selected spots or droplets on the solid support. The DMD can be a chip having on its surface, for example, several hundred thousand to several million microscopic mirrors arranged in a rectangular array which correspond to the spots or droplets to be heated. The mirrors can be individually rotated (e.g., ±10-12°, to an on or off state. In the on state, light from a light source (e.g., a bulb) is reflected onto the solid support to heat the selected spots or droplets. In the off state, the light is directed elsewhere (e.g., onto a heatsink). In one example, the DMD can consist of a 1024×768 array of 16 μm wide micromirrors. In another example, the DMD can consist of a 1920×1080 array of 10 μm wide micromirrors. Other arrangements of array sizes and micromirror widths are also possible. These mirrors can be individually addressable and can be used to create any given pattern or arrangement in heating different spots on the solid support. The spots can also be heated to different temperatures, e.g., by providing different wavelength for individual spots, and/or controlling time of irradiation.

In certain embodiments, the DMD can direct light to selected spots or droplets. In some embodiments, the DMD san be used to identify, select, melt, and/or cleave any oligonucleotide of choice. In some examples, the DMD can identify error-containing duplexes and/or error-free duplexes. The DMD can selectively melt error-containing duplexes and/or error-free duplexes. In some embodiments, The DMD can selectively cleave error-containing duplexes and/or error-free duplexes. The selective melting and cleaving can also be performed by any other methods and/or techniques known in the art.

Some aspects the invention relate to the design of oligonucleotides and device comprising a plurality of oligonucleotides for sequence verification during the extension process and the assembly of high fidelity polynucleotides. One skilled in the art will appreciate that template oligonucleotides and newly synthesized polynucleotides (e.g., extension products)

can have inherent errors (e.g., for chemically synthesized oligonucleotides, deletions at a rate of 1 in 100 bases and mismatches and insertions at about 1 in 400 bases). Assuming an average error rate of 1 in 300 bases and an average template oligonucleotide size of 70 bases, every 1 in 4 template oligonucleotides will contain an error compared to a reference sequence (e.g., the wide-type sequence of a gene of interest). For example, template oligonucleotide can contain an error which can be a mismatch, deletion, or insertion. In PCR synthesis and chain extension, the error is retained in the synthesized oligonucleotide. Additional errors such as deletions can be introduced during PCR or chain extension. For example, shorter extension products may result from incomplete extension during one or more cycles. The ability to perform sequence verification can lead to a reduced error rate in the final product. Methods for sequence verification and error correction are needed for high-fidelity gene synthesis/assembly and are provided herein.

Some aspects of the invention relate to the design of oligonucleotides for sequence verification of the extension sequence regions formed during the polynucleotide extension steps. In some embodiments, the sequence of the immobilized oligonucleotides is designed to allow sequence verification of the extension products. In other embodiments, the sequence of the input polynucleotide is designed to allow sequence verification of the immobilized oligonucleotides. More specifically, methods and devices are provided to allow sequence verification of extension products synthesized during the (n−1) and (n−2) extension reactions. Therefore, methods of the invention provide a way to screen for products that contains the (N−1) to (N−2) extension junction sequences (referred herein as junction quality control or junction QC). As shown in FIG. 2A, the support-bound sequence (201) contains three sequence regions: a first sequence region (204), a second sequence region (206) and a third sequence region (205). Sequence region (204) corresponds to the extension sequence template of extension step (n). Sequence region (205), the screening region, includes the sequence of extension template from the previous step (n−1). Sequence region (206) includes some or all of the sequence of extension template from step (n−2) and corresponds to the junction QC region. In a preferred embodiment, (n−1) and (n−2) refer to two consecutive extension steps. The added input polynucleotide (203) includes a sequence region (208) that is partially complementary to the sequence of oligonucleotide (201). In a first step, polynucleotide (203) is added to the feature comprising oligonucleotides (201) and partially hybridizes to the immobilized sequences (201), forming a hybridized partial duplex containing sequence (208) hybridized to sequence (205) (corresponding to the (n−1) extension step), and sequence (206) (corresponding to the (n−2) extension step). The formation of the hybridized partial duplex allows for screening of error containing input molecules (203). Error containing molecules may include sequence errors (such as substitution, insertion, deletions, etc. . . . ) or may be missing extension sequences regions complementary to sequence region of the immobilized oligonucleotide (for example, sequence regions region (205) and (206) of oligonucleotide (201), FIG. 2A). The added polynucleotide comprising a sequence error will have a lower melting temperature when compared to an error-free polynucleotide and may be removed under stringent melt conditions. The conditions for stringent melt (e.g., a precise melting temperature) can be determined by observing a real-time melt curve. In an exemplary melt curve analysis, PCR products are slowly heated in the presence of double-stranded DNA (dsDNA) specific fluorescent dyes (e.g., SYBR Green, LCGreen, SYTO9 or EvaGreen). With increasing temperature the dsDNA denatures (melts), releasing the fluorescent dye with a resultant decrease in the fluorescent signal. The temperature at which the dsDNA melts is determined by factors such as nucleotide sequence, DNA length and GC/AT ratio. Typically, G-C base pairs in a duplex are estimated to contribute about 3° C. to the Tm, while A-T base pairs are estimated to contribute about 2° C., up to a theoretical maximum of about 80-100° C. However, more sophisticated models of Tm are available and may be in which G-C stacking interactions, solvent effects, the desired assay temperature and the like are taken into account. Melt curve analysis can detect a single base difference. Methods for accurate temperature control at individual features can be used as disclosed in PCT Application No. PCT/US10/055,298. In some embodiments, a stringent wash step with a carefully controlled temperature can melt and remove the error-containing input polynucleotides after annealing. With regards to FIG. 2, the sequence region (208) of the input polynucleotide that hybridizes to sequence region (206) of the immobilized oligonucleotide allows for sequence verification to interrogate for both the existence of the (N−2) sequence and the sequence correctness of the hybridized section. The sequence region (208) that hybridizes to the sequence region (205) of the immobilized oligonucleotide allows for sequence verification to interrogate for both the existence of the (N−1) sequence and the sequence correctness of the hybridized section. Sequence regions used for sequence verification can be at least 2 bases long, at least 5 bases long, at least 10 bases long, at least, 20 bases long, at least 30 bases long, at least 50 bases long, at least 100 bases long, at least 300 bases long, at least 1000 bases long, etc. . . . One skilled in the art will therefore appreciate that the design of sequence (208) that allows for sequence verification of both (N−1) and (N−2) extensions reduces the possibility of extension of error containing input polynucleotides.

Figure 2B:
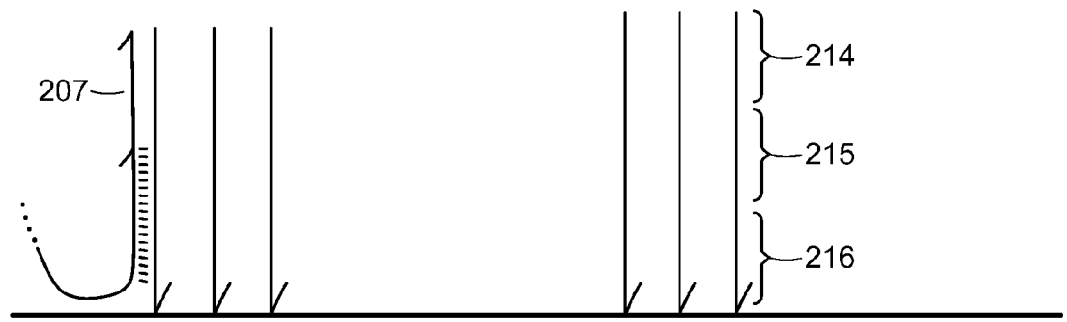
Figure 2C:
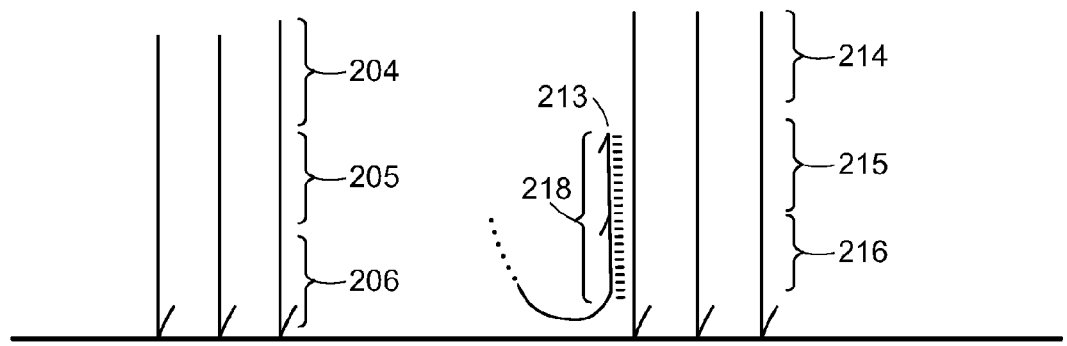

In a subsequent step, after the stringent wash step, extension of the annealed input polynucleotides (203) by a polymerase enzyme leads to the production of extension product (213) comprising sequence (203) and sequence (207) complementary to sequence (204) (FIG. 2B). In a following step, this extension product (213) may be melted from its template (201). The extension product can then hybridize to a different oligonucleotide (202) at a different solid support feature, thereby allowing the (n+1) extension step (FIG. 2C). In the (n+1) extension step, in a similar way than to the (n) extension step, the input molecule (213) includes a sequence region that is complementary to an immobilized oligonucleotide, (e.g., sequence region (218) complementary to sequences 215 and 216, FIG. 2C). In some embodiments, the third sequence region of the second immobilized oligonucleotide may be identical to the first sequence region of the first oligonucleotide and the second sequence region of the second immobilized oligonucleotide may include some or may be identical to the third sequence region of the first oligonucleotide. For example, the junction QC sequence region (215) of oligonucleotide (202) may be identical to extension template sequence region (204) of oligonucleotide (201) and the screening sequence region (216) of the second immobilized oligonucleotide may include some or may be identical to the screening sequence (205) of the first oligonucleotide (201). A stringent wash step can then be carried out to remove error containing input molecules, and a polymerase can be added to extend the error-free annealed input molecules (213) using sequence region (214) of the second immobilized oligonucleotide as the template, resulting in an elongated product. These cycles of melting, annealing, stringent washes and extension may be repeated until the full length polynucleotide having a predetermined sequence is synthesized. In some embodiments, the process can be carried out for M steps, where M can be greater than 1, greater than 10, greater than 100, greater than 1,000, greater than 10,000, greater than 100,000. In some embodiments, the number of cycles is equal or superior to the number of immobilized oligonucleotides. In some embodiments, the final polynucleotide product may be amplified.

In some embodiments, the lengths of the extension template (e.g., (204)) are from about 2 to about 1000 bases, from about 100 to about 1000 bases, from about 300 to about 1000 bases, from about 100 to bout 300 bases, from about 2 to about 100 bases. The lengths of some or each extension templates can be variable, depending on the relevant constraints (e.g hybridization temperature, GC content of the extension template, sequence of the extension template, final product sequence, buffer content, presence of repeats, secondary structure, etc. . . . ). For example, the length a first extension template (corresponding to the first region of the support-bound oligonucleotide), at a first feature of the support, can be different than the length of a second extension template, at a second feature of the support, or the length of a $n^{th}$ extension template, at a $n^{th}$ feature of the support. For example, length of sequence N (e.g., (204), FIG. 2A) can be different than the length of sequence (N+1) (e.g (214), FIG. 2B). Similarly, the length of the second region of the first plurality of support-bound oligonucleotide can be different than the length of the second region of the second plurality of support-bound oligonucleotides. For example, the length of the screening region (205) of oligonucleotide (201) can be different than the length of the screening region (215) of oligonucleotide (202), see FIG. 2A-B. Similarly, depending on the relevant constraints, the lengths of the junction QC region of the first plurality of oligonucleotides can be different than the length of the junction QC region of the second plurality of oligonucleotides. For example, the length of junction QC region (206) of oligonucleotide (201) can be different than the length of junction QC region (216) of oligonucleotide ((202), FIG. 2A-B). In a preferred embodiment, the length of the first extension template region (e.g., first region of the support-bound oligonucleotide, (204), (214)) is from about 10 bases to about 30 bases; the length of the second region of the support-bound oligonucleotide (e.g., (205), (215)) is from about 10 to about 30 bases, the length of junction QC region (e.g. (206), (216)) is from about 10 to about 45 bases.

In some embodiments, certain design considerations and constraints may influence the choice of the length of the extension template sections, screening sections, and junction QC sections. One skilled in the art will appreciate that mismatch (e.g., single or multiple bases mismatches) discrimination relies upon differential hybridization between perfectly matched and mismatched duplexes, and therefore in the difference of melting temperature between the perfectly matched and the mismatched duplexes. Depending of the duplex size, the melting temperature can be relatively small, such as less than 0.5° C., less than 1° C., less than 2° C., or less than 5° C. The difference of melting temperature can be improved by minimizing the length of the hybridized region. However, the length of the hybridized section needs to include the entire length of the extension template from the previous extension step (e.g., screening region), and the junction QC section. Moreover, the junction QC region needs to include a sufficient number of bases to be specific to the input polynucleotide sequence and to provide a useful sequence verification assay for the junction. Other considerations, such as minimization of undesirable side products, can also influence the lengths of each of the oligonucleotide sequence sections.

During the sequence verification step, the input polynucleotide is hybridized to the support-bound oligonucleotide, and the partial duplex is subjected to stringent melt conditions prior to polymerase extension. In some embodiments, the duplex (e.g., formed by sequences 208, 205, and 206, FIG. 2A) melting temperature ranges from about 25° C. to about 95° C., depending on the hybridized sequences, the buffer conditions or other experimental conditions.

One should appreciate that other mismatch detection methods can also be used to achieve the benefits of a stringent melt step. In some embodiments, a mismatch binding protein, such as MutS, can be used to bind to a mismatch in the hybridized region (e.g., formed by 208, 205, and 206, FIG. 2A), preventing such hybrids to be used in subsequent steps. MutS is a bacterial protein. MutS from *Thermus aquaticus* can be purchase commercially from the Epicenter Corporation, Madison, Wis., Catalog No. SP72100 and SP72250. The gene sequence for the protein is also known and published in Biswas and Hsieh, Jour. Biol. Chem. 271:5040-5048 (1996) and is available in GenBank, accession number U33117. It is also possible to design and synthesize small organic molecules which will bind to specific nucleotide mismatches, such as dimeric napthyridine 1, a synthetic ligand that binds to a G-G mismatch. A cocktail of such ligands which, in combination, recognizes all possible mismatches could replace CEL1. Other protein agents that can differentiate between matched and unmatched duplexes could also be used. For example, the T7 endonuclease I will specifically cleave a DNA strand at a mismatch, and it would be possible to use this enzyme as a catalytic destroyer of mismatched sequences or to inactivate the cleavage function of this enzyme for use in this process as a mismatch binding agent. T4 endonuclease VII can specifically bind and cleave DNA at duplex mismatches. A mutant version of this enzyme has already been engineered that lacks the nuclease activity but retains the ability to bind mutant duplex DNA molecules (see Golz and Kemper, Nucleic Acids Research, 27:e7 (1999)). SP nuclease is a highly active nuclease from spinach that incises all mismatches except those containing a guanine residue, and this enzyme could also be engineered to remove the cleavage activity or used directly. Two or more of these binding agents could be combined to either provide further stringency to the filtration or to cover all types of sequence errors if one agent does not bind to all possible mismatches.

In other embodiments, a mismatch specific endonuclease, such as CEL1, or mixtures containing CEL1, can be used to cleave mismatch containing hybrids (see for example, PCT Patent Application No. PCT/US2010/057405, which is incorporate herein by reference in its entirety). Heteroduplex recognition and cleavage can be achieved by applying a mismatch endonuclease to the reaction mix. One preferred mismatch endonuclease is CEL1 endonuclease which has a high specificity for insertions, deletions and base substitution mismatches and can detect two polymorphisms which are five nucleotides apart from each other. CEL1 is a plant-specific extracellular glycoprotein that can cleave heteroduplex DNA at all possible single nucleotide mismatches, at 3' to the mismatches (Oleykowski C A et al, 1998, Nucleic Acids Res. 26: 4596-4602). CELL is useful in mismatch detection assays that rely on nicking and cleaving duplex DNA at insertion/ deletion and base substitution mismatches. In an exemplary embodiment, an endonuclease, sold under trademark SURVEYOR® Nuclease (Transgenomic Inc.) may be added to the hydrated feature containing the oligonucleotide duplexes.

SURVEYOR® Nuclease is a mismatch specific endonuclease that cleaves all types of mismatches such as single nucleotide polymorphisms, small insertions or deletions. Addition of the endonuclease results in the cleavage of the double-stranded oligonucleotides at the site of the mismatch. The remaining portion of the oligonucleotide duplexes can then be melted at a lower and less stringent temperature (e.g., stringent melt) needed to distinguish a single base mismatch. These heteroduplex recognition and removal methods can be used in conjunction or instead of the stringent melt methods.

Figure 3A:
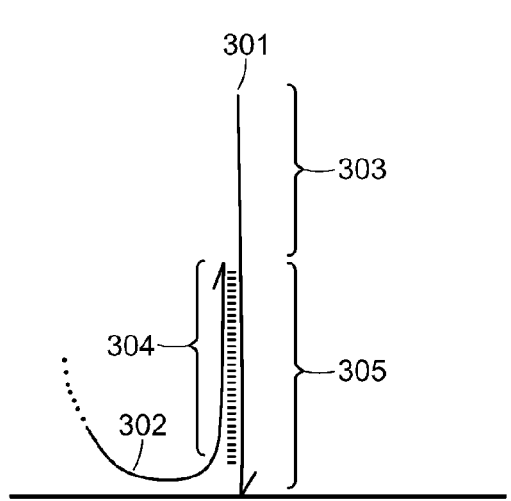
FIG. 3 illustrates a non-limiting example of different design strategies of screening of error-containing polynucleotides.

In some embodiments, the immobilized oligonucleotides are designed to include two or more different sequence regions. In some embodiments, the immobilized oligonucleotides are designed to include two different sequence regions, a first sequence region and a second sequence region. In an exemplary embodiment, the immobilized oligonucleotide (301) comprises a first sequence region (303) and a second sequence region (305), wherein the first sequence region (303) serves as a template for the current extension step (step n), and part of the second sequence region (305) allows sequence verification of the extension product from the previous extension step (step n−1) (FIG. 3A). In some embodiments, the sequence length of (303) and (305) can be adjusted to satisfy a variety of design considerations as described below.

Figure 3B:
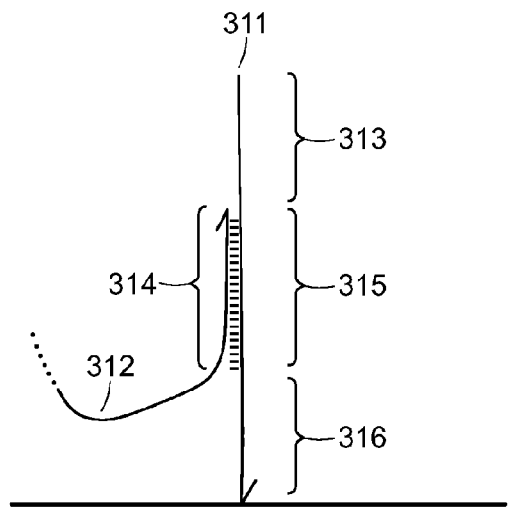

In other embodiments, the immobilized oligonucleotides are designed to include three different sequence regions, a first sequence region, a second sequence region and a third sequence region. In a preferred embodiment, the first sequence region is at the 5' end of the oligonucleotide, the second sequence region is in the middle part of the oligonucleotide and the third sequence region is at the 3' end of the oligonucleotide. In exemplary embodiment and referring to FIG. 3B, the immobilized oligonucleotide (311) comprises a first sequence region (313) which serves as the template for the current extension step (step n), a second sequence region (315) allowing sequence verification of the extension product from the previous step (step n−1), and a third sequence region (316) which does not participate in the extension process. The inclusion of the third sequence region (316) allows for additional freedom in the design process such that the total length of (313) and (315) does not need to fill the length of (311) completely. The length of the third sequence regions may be at least 5, at least 10, at least 25, at least 50 bases long.

Figure 3C:
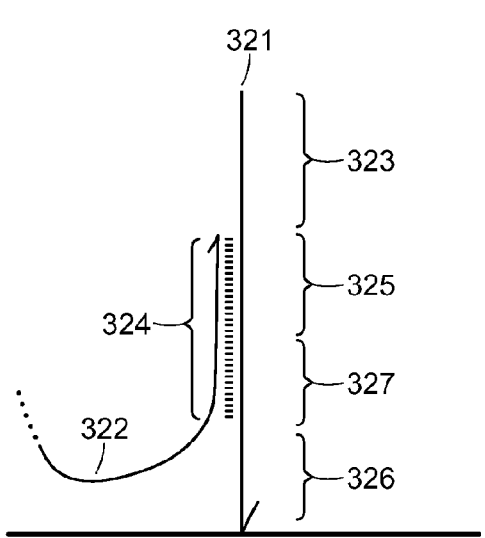

Yet, in another embodiment, the immobilized oligonucleotides are designed to include four different sequence regions, a first sequence region, a second sequence region, a third sequence region and a fourth sequence region. In a preferred embodiment, the first sequence region is at the 5' end of the oligonucleotide, and the third sequence region is at the 3' end of the support bound oligonucleotide. In exemplary embodiment and referring to FIG. 3C, the immobilized oligonucleotide (321) comprises a first sequence region (323) which serves as the template for the current extension step (step n), a second sequence region (325) allowing sequence verification of the extension product from the previous step (step n−1), third sequence region (326) which does not participate in the extension process, and a fourth sequence region (327) allowing sequence verification of the extension product from the previous step (step n−2).

Figure 3D:
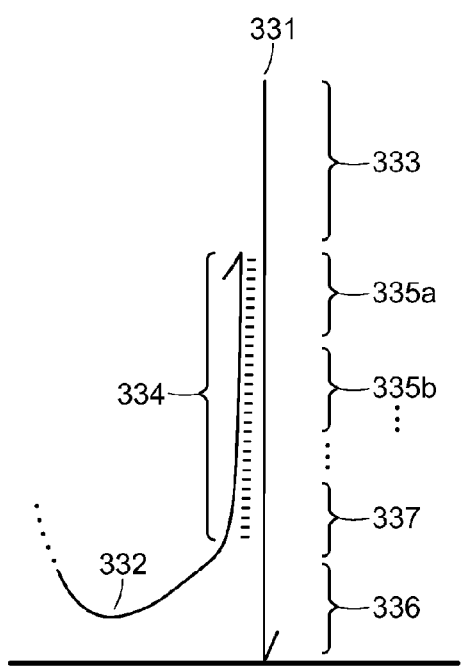

In yet another embodiment, the immobilized oligonucleotide comprises a plurality of different sequence regions. FIG. 3D shows a broadening of the strategy described and illustrated in FIG. 3C. In this strategy, sequence verification can be done for (n−1), (n−2), (n−3), etc. . . . extension steps, by using (335a), (335b), (335c), etc. . . . sequence regions in a similar way as described herein.

In some embodiments, at a first step, a primer is added and anneals to a first oligonucleotide on the solid support. The partial duplex is subjected to a first stringent wash to remove error containing primers. In a second step, the primer extends by appropriate polymerase enzyme into a product at least partially complementary to the first oligonucleotide. Referring to FIG. 4, the polymerase extension reaction adds sequence (403a) to the seed primer using sequence (403) as template, resulting in the first step extension product (409). At a second step, the complementary product is melted from the first oligonucleotide and allowed to partially anneal to sequence region (403) of a second immobilized oligonucleotide ((410), FIG. 4) through its complementary region (403a). In a third step, the partial duplex may be subjected to a stringent wash to remove error-containing products. As described above, the 3' end of the second oligonucleotide is designed to comprise a sequence complementary to 3' end of the complementary product (e.g., polynucleotide (409)), thereby allowing sequence verification of the extension product (N−1). In a fourth step, the partial duplex is subjected to conditions promoting extension. Referring to FIG. 4, polymerase extension adds sequence (404a) to the seed primer using sequence (404) as template, resulting in the first step extension product (419). The extension product (419) is melted from the template (410) to allow for extension step 3. Further extensions step 3 and step 4 are illustrated in FIG. 4. In an alternate embodiment, step 1 of the assembly can be skipped by using a seed primer that resembles extension product (409).

In some embodiments, immobilized oligonucleotides are designed to sequence verify polynucleotides comprising the (N−1) and (N−2) extension products, providing in a junction quality control (QC) assay. In an exemplary embodiment, the immobilized oligonucleotide sequence is designed to comprise at least three sequence regions: a first sequence region which served as template for extension, a second sequence region to allow sequence verification of the first extension product and a third sequence region to allow junction sequence verification of step (N−2). In some embodiments, the third sequence is designed to be complementary to part of or the entirety of the seed primer. The length of the third sequence can be longer or shorter than the length of the seed primer and can comprise sequences that are no involved in the extension process. In a subsequent step, the partial duplex is subjected to stringent melt conditions to wash off error-containing molecules. After the stringent wash, the resulting duplexes are subjected to polymerase extension conditions to generate a longer polynucleotide using the immobilized oligonucleotide as a template. Cycles of melting, annealing, stringent washes and extension can be repeated until a full length polynucleotide is synthesized.

Figure 5:
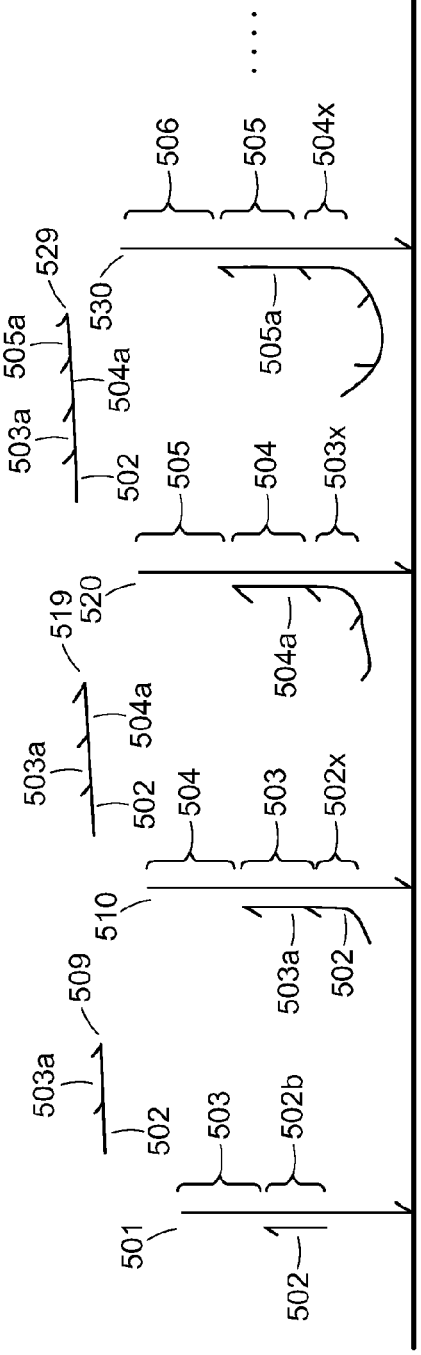
FIG. 5 illustrates a non-limiting exemplary method for polynucleotide extension and screening of error-containing polynucleotides.

Aspects of the methods are illustrated in FIG. 5. The first extension step (step 1) is similar to the first step described above and illustrated in FIG. 4, resulting in the step 1 extension product ((509), FIG. 5). The immobilized oligonucleotide (510) comprises three sequence regions. The first sequence region (504) serves as the sequence template for step 2 extension reaction. The second sequence region (503) serves as an interrogation or verification sequence of step 1 extension reaction. The third sequence region (502X) serves as a junction interrogation sequence of extension step (n−2) (in this case the seed primer). Sequence (502X) can be a part of or the entirety of the seed primer sequence (502). The length of (502X) can be designed such that it optimizes certain design aspects of the extension strategy. After a stringent wash that removes the error containing input molecules, a polymerase promotes extension of polynucleotide (509) to include sequence (504a) based on template sequence (504), resulting in the step 3 extension product (519). Referring to step 3, the immobilized oligonucleotide (520) comprises three sequence regions: a first sequence region (505) corresponding to the sequence template for extension step 3, a second sequence region (504) corresponding to an interrogation sequence of extension step 2, and a third sequence region (503X) corresponding to a junction interrogation sequence of step (n−2) (in this example, step 1). Sequence (503X) can be a part of or the entirety of the step 1 extension sequence (503). The length of (503X) can be designed such that it optimizes certain design aspects of the extension strategy. After a stringent wash that removes the error-containing input molecules, a polymerase extends polynucleotide (519) to include sequence (505a) based on template sequence (505), resulting in the extension step 3 product (529). The process can continue to step 4, as illustrated in FIG. 5. Subsequent steps can be carried out until the desired final product is synthesized. In some embodiment, the lengths of junction interrogation sequences (502X), (503X), (504X) . . . are designed such as the stringent melt temperature of all products of the extension steps is substantially the same or within a narrow temperature window (for example, within less than 1° C., within less than 3° C., within less than 4° C., within less than 5° C.). The uniformity of melting temperature allows simplified temperature control during the extension and sequence verification process.

Aspects of the invention relate to enhancing nucleic acid assembly procedures by using a stringent wash step after annealing of the polynucleotide to the immobilized oligonucleotides through the complementary regions and prior to polymerase extension. Accordingly, aspects of the invention may be useful for increasing the fidelity of a nucleic acid assembly reaction (e.g., increasing the proportion of assembled nucleic acids that have a desired predetermined polynucleotide or target sequence). In some embodiments, the immobilized oligonucleotides comprise at least two, at least three different and contiguous sequence regions. As illustrated above, the stringent wash step allows for the reduction of the extension of error containing polynucleotides. In some embodiments, the error correction (screening) process relies on the difference in melting temperature between error-free (or substantially error free) and error-containing duplexes. The use of a stringent wash conditions with precisely controlled temperature, allows for the error-containing input molecules to be washed away and removed from the reaction sites, achieving the overall goal of error reduction (correction and screening).

A preparation of oligonucleotides designed to have a predefined sequence may include oligonucleotide molecules having the designed sequence in addition to oligonucleotide molecules that contain errors (e.g., that differ from the designed sequence at least at one position). A sequence error may include one or more nucleotide deletions, additions, substitutions (e.g., transversion or transition), inversions, duplications, or any combination of two or more thereof. Oligonucleotide errors may be generated during oligonucleotide synthesis. Different synthetic techniques may be prone to different error profiles and frequencies. In some embodiments, error rates may vary from 1/10 to 1/200 errors per base depending on the synthesis protocol that is used. However, in some embodiments lower error rates may be achieved. Also, the types of errors may depend on the synthetic techniques that are used. For example, in some embodiments chip-based oligonucleotide synthesis may result in relatively more deletions than column-based synthetic techniques. In some embodiments, the sequence errors may be present on only one copy of a double-stranded heteroduplex nucleic acid molecule. In addition, or alternatively, the sequence errors may be present on both strands of a double-stranded homoduplex error-containing nucleic acid molecule.

Figure 6B:
FIG. 6 illustrates non-limiting exemplary methods for polynucleotide extension and screening of error-containing polynucleotides by shuffling.
Figure 6C:
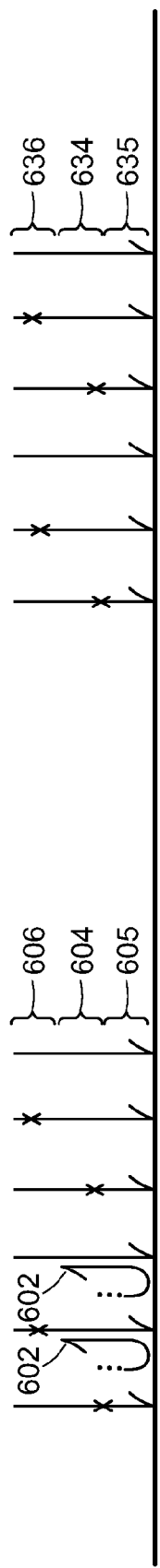

Some aspects of the invention further provide a process for the detection and removal of error-containing oligonucleotides. This process is illustrated in FIG. 6. With reference to FIG. 6A, template oligonucleotides (601), can have inherent errors as they are generally chemically synthesized. Oligonucleotides (601a), (601b), and (601c) correspond to a plurality of oligonucleotides immobilized at a feature where the current step of extension takes place (step (n)). In some embodiments, oligonucleotides (601a), (601b), and (601c) are designed to have a predefined sequence but may include oligonucleotide molecules having the predefined sequence in addition to oligonucleotide molecules containing nucleotide errors. Errors may be located at different sequence regions of the template oligonucleotide and/or at different sequence regions of the annealed polynucleotide. For example, referring to FIG. 6A, the oligonucleotide population represented by (601a) contains one or more errors in the region of sequence outside of the current step (step n) extension template (606). The oligonucleotide population represented by (601b) contains one or more errors in the region of the current step (step n) extension template (606) (FIG. 6B). The oligonucleotide population represented by (601c) does not contain any error (error-free oligonucleotide). The input polynucleotides, represented by (602) and (603) in FIG. 6A, may or may not comprise sa equence error. For example, input polynucleotide (602) does not contain any error in the sequence recognition segment of (604b) and (605b) whereas input polynucleotide (603) contains at least one error in the sequence recognition segment of (604a). Sequences (604a) and (604b) correspond to sequences intended to hybridize with sequence (604) on the immobilized templates oligonucleotides (601a, 601b, 601c). Sequences (605a) and (605b) correspond to sequences intended to hybridize with sequence (605) on the immobilized templates oligonucleotides (601a, 601b, 601c).

During the annealing step, input polynucleotide sequences comprising error free polynucleotide sequences (602) and error-containing polynucleotide sequences (603) are allowed to hybridize to a feature containing immobilized templates oligonucleotides represented by (601a), (601b), and (601c). As each input polynucleotide sequence may anneal with different oligonucleotide template sequences present in the plurality of oligonucleotides, a number of polynucleotide-template partial duplex combinations is possible. FIG. 6A shows an exemplary embodiment of input polynucleotide sequences annealing template oligonucleotides, resulting in six different polynucleotide-template oligonucleotide duplex combinations (650A, 650B, 650C, 650D, 650E, and 650F). The duplex (650A) is formed by hybridization of (602) to (601a). The duplex (650B) is formed by hybridization of (602) to (601b). The duplex (650C) is formed by hybridization of (602) to (601c). The duplex (650D) is formed by hybridization of (603) to (601a). The duplex (650E) is formed by hybridization of (603) to (601b). The duplex (650F) is formed by hybridization of (603) to (601c). Partial duplexes (650A), (605D), (605E), (605F) are heteroduplexes or mismatched duplexes which contain at least one error or mismatch in one or both strands. Partial duplexes (650B), (650C) do not contain error in their double strand portion.

One should appreciate that if the polymerase extension step is carried out without performing first a stringent wash the extension products may contain errors in the newly extended segment. For example, extension of input polynucleotides (602) and (603) illustrated in the six scenarios (650A, 650B, 650C, 650D, 650E, 650F, FIG. 6B) will result in extension products (611), (612), (613), (614), (615) and (616), respectively. Some of these extension products may contain errors in the sequence recognition segment formed by (604) and (605). Errors in the region corresponding to (605) could be propagated through the subsequent extension steps, resulting in errors in the final polynucleotide product. In preferred embodiments, the duplexes are subjected to stringent hybridization conditions prior to extension. Stringent conditions are chosen to denature mismatched duplexes (650A), (650D), (650E), (650F) without denaturing matched duplexes (650B) and (650C). The stringent wash results in the removal of mismatched duplexes ((650A), (650D), (650E), (650F), FIG. 6C). Therefore, after stringent melt and polymerase extension, of the possible extension products (611), (612), (613), (614), (615), and (616), only extension products (612) and (613) will be synthesized (FIG. 6D). Both extension products (612) and (613) do not contain any error in the sequence section formed by (604) and (605). Therefore, the stringent wash step prior to the extension step effectively filtered out errors in the sequence recognition section formed by (604) and (605). However, it is worthwhile to note that an unlikely event could take place that will escape this error reduction mechanism if used alone. In fact, it is possible that the position of the error on the input molecule corresponds to the position of the error on the immobilized oligonucleotide template, the errors forming perfect complements (e.g., homoduplex). For example, In the case of duplex (650D), both the input molecule and the immobilized template oligonucleotide contain one or more errors or mismatches and it is possible that the position of the error on the input molecule corresponds to the position of the error on the immobilized oligonucleotide template, the errors forming perfect complements. In this case, the error-containing duplex (650D) would exhibit a melting temperature similar to that of the error-free duplexes (601b) and (601c). However, one should appreciate that, statistically, such an occurrence is very unlikely due to the shuffling process (melting and re-annealing process) that takes place. During the shuffling process (described below), the extension products generated from the previous step ((602) and (603)) are melted and re-annealed to a population of support-bound templates with randomly distributed errors.

After polymerase extension, the extension products of extension step (n) are denatured under melting conditions and the complementary extension products are separated from the template oligonucleotide, producing a population of error-free polynucleotides and error containing polynucleotides. Referring to FIG. 6D, error-free polynucleotides (613) do not contain any error in the sequence recognition region of (606b) and (604b) whereas error-containing polynucleotide (612) contains at least one error in the sequence recognition regions of (606a) and (604a). Sequences (604a) and (604b) correspond to sequences intended to hybridize with sequence (635) on the immobilized oligonucleotide templates ((631a), (631b), (631c)), and (606a) and (606b) correspond to sequences intended to hybridize with sequence (634) on the immobilized oligonucleotide templates ((631a), (631b), (631c)). The stringent wash process is carried out similarly to the stringent wash process of step (n), and the extension step produces two populations of extension products, in a similar way as to the extension step (n) described herein. In some embodiments, the extension process may be carried out for multiple cycles, elongating the polynucleotide product to the desired length.

In some embodiments, an additional error correction mechanism can be included in the process flow. The concept of shuffling can be used in conjunction with any or all error correction methods disclosed herein. In some embodiments, after polymerase extension duplexes are denatured under melting conditions, the complementary extension products are separated from the template strands, and allowed to re-hybridized to an oligonucleotide of the plurality of oligonucleotides, such as a neighboring oligonucleotide. For example, referring to FIG. 6B, after denaturation of the duplexes (650A, 650B, 650C, 650D, 650E, 650F), extension products can re-anneal to neighboring oligonucleotides. This way, error-prone extension products can re-anneal with error-free oligonucleotides and heteroduplexes can be recognized and removed. For example, extension product (615) can re-anneal with complementary single-stranded oligonucleotides (601a) or (601b). If the extension product sequence contains errors due to errors in the template sequence, such errors can be detected after shuffling if the neighbor surface attached template does not contain the same error at the same position. For example, as illustrated in FIG. 6, extension product (615) carries an error, illustrated by symbol x, on extension strand in the extension sequence region (606). Such error can be detected after shuffling and annealing to neighbor surface attached templates, for example (601a) or (601c), which do not contain the same error at the same position as (601b). The difference in sequences (and error content) between the neighboring surface attached templates ((601a) or (601c)) and the original surface attached template (601b) results in the formation of a mismatch in the duplex formed by the extension product (e.g., (615)), and the neighbor surface attached template. Such mismatches can be used to remove extension products containing the underlying error content. In some embodiments, the mismatches can be recognized and bind with a binding protein, such as MutS. In other embodiments, the mismatches can be recognized and cleaved with a mismatch recognizing endonuclease, such as CEL1, or cocktail mixtures of such protein and other proteins (for example, the SURVEYOR® mix by Transgenomics). Yet in other embodiments, the mismatched extension products can be removed under stringent melt conditions, the melting temperature between the mismatched duplex and the matched duplex being different.

In some embodiments, the shuffling process is applied after with the stringent melt step and extension step. As shown in FIG. 6D, after stringent melt and polymerase extension, two populations of extension products exist (612, 613). It is possible to perform a shuffling step at this stage, in which (612) and (613) are separated from the template stand under melting conditions and re-hybridized (shuffled) to hybridize to a different template at the same feature of the support (the feature comprising oligonucleotides (601a), (601b), and (601c)). The shuffling step will result in the reduction of the population of error-containing polynucleotides (e.g., 612) and enrichment of the population of error-free polynucleotides (e.g., 613). In some embodiments, the shuffling process will result in a population of substantially error-free polynucleotides.

One should appreciate that extension methods described herein can contain a build-in shuffling mechanism and therefore are self-correcting, self-screening or self-filtering. As shown in FIGS. 6D and 6E, the two populations of step (n) extension products, (612) and (613), are produced during step (n) extension. Melting of the duplexes comprising two populations of step (n) extension products, (612) and (613), and subsequent hybridization of the step (n) extension products to the step (n+1) surface attached templates (631a, 631b, 631c) essentially implements a shuffling operation. In this case the shuffling operation is done on the sequence recognition region formed by sequence regions (634) and (635).

Aspects of the invention also relate to methods and devices for removing error-containing oligonucleotides from a plurality of oligonucleotides or polynucleotides. In some embodiments, the method comprises the steps of hydrating at least one first feature of the solid support, following or at the annealing step, forming a droplet comprising oligonucleotides duplexes; heating the solid support to a first melting temperature under stringent melt conditions, thereby denaturing duplexes comprising error-containing oligonucleotides and releasing error-containing oligonucleotides; removing the error-containing oligonucleotides from the solid support; optionally repeating previous steps on at least one second different feature and at least one different melting temperature; denaturing error-free duplexes; and releasing error-free oligonucleotides in solution. Stringent melt conditions can be determined by a real-time melt curve. In some embodiments, the support can be dried prior to the first and to the subsequent hydrating steps. In some embodiments, a subset of discrete features is selectively heated. For example, one or more discrete features are selectively heated using a digital mirror device (DMD).

It should be appreciated that each discrete feature may be subjected independently to different stringent wash conditions using discrete droplets volume. However, it may be desirable to have the same stringent wash temperature at all or a subset of the features such that stringent wash can be achieved for all of the participating features under the same temperature condition.

During the stringent wash step, it may be desirable to have a global stringent wash temperature such that stringent wash can be achieved for all of the participating regions under the same temperature condition. Accordingly, some aspects of the invention relate to the design of oligonucleotides such as the stringent wash temperature is the same or within a narrow temperature window. For example, the pluralities of oligonucleotides are designed to have a melting temperature that is within 0.1° C., 0.2° C., 0.3° C., 0.4° C., 0.5° C., 0.6° C., 0.7° C., 0.8° C., 0.9° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C. In some embodiments, the length of the hybridization region is varied at different features. One should appreciate that by adjusting the hybridization section length, the melting temperature of each of the extension step can be controlled.

Figure 7:
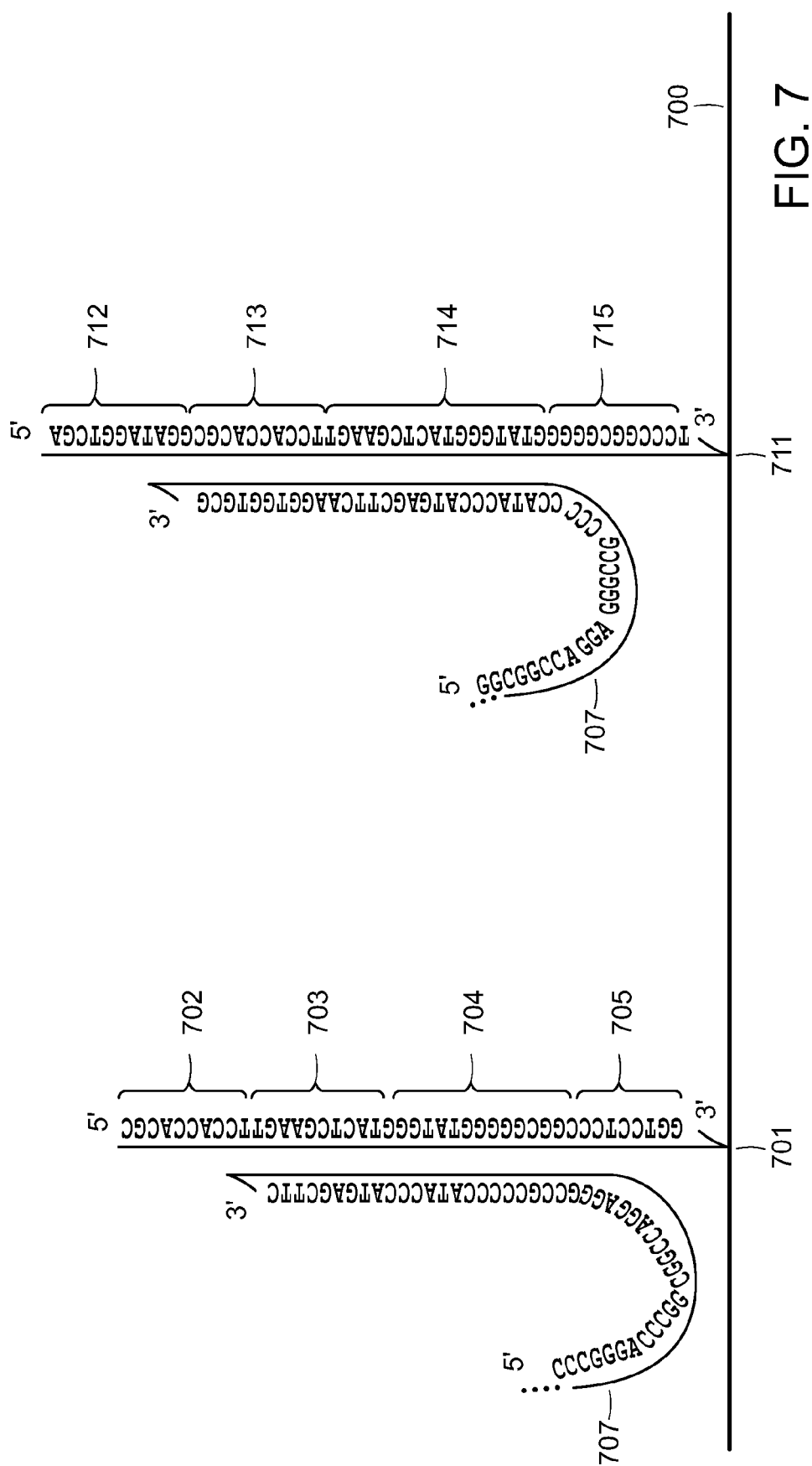
FIG. 7 illustrates a non-limiting example of global melting temperature optimization for stringent wash.

FIG. 7 shows two support-bound oligonucleotides ((701), (711)) attached to two different features on a solid support (700), each feature supporting a plurality of oligonucleotides. Although only two such features are shown, it is understood that plurality of features exist for each extension design, and the number of features can be between 1 to 100,000,000. In some embodiments, the support-bound oligonucleotides comprise at least four sequence regions: a 5' end sequence region corresponding to the extension sequence template region, a screening sequence region at the 3' end of the extension sequence template region, a junction QC sequence regions at the 3' end of the screening sequence region and a 3' end spacer sequence region. In a preferred embodiment, the junction QC sequence region includes part or all of the sequences of extension step (n−2), and optionally may include additional sequences from extension step (n−3), depending on the length design of the oligonucleotide. In a preferred embodiment, the spacer region sequence does not participate in the extension reactions but may be used for pre- or post-extension nucleic acid processing. For example, the support-bound template oligonucleotide (701) for the extension step (n) is designed to comprise an extension template sequence region for the template for step (n) extension (702), a screening sequence region (703) corresponding to extension step (n−1), a junction QC sequence region (704) that may contain part or all of the sequences of extension step (n−2), and may even include additional sequences from step (n−3), and a spacer sequence region (705). Similarly, the support-bound template (711) in the step extension (n+1) comprises at least four sections: the extension template sequence region for step (n+1) extension (712), the screening section for extension step (n) (713), the junction QC sequence region (714) which may contain part or all of the sequences of extension step (n−1), and may even include additional sequences from step (n−2), depending on the length this section, and a spacer section (715) whose sequence may not participate in the extension reactions.

In some aspects of the invention, by varying the length of the hybridization regions of each oligonucleotide, one can control the melting temperature of the duplexes. Referring to FIG. 7, the hybridization region is composed of the screening sequence region (703) for step (n), (713) for step (n+1) and the junction QC sequence region (704) for step (n) and (714) for step (n+1). The length of the hybridization section for step (n) is the combined length of the screening section (703) and the junction QC section (704). Since the length of the screening section (703) is the same as the length of the extension template sequence region for the previous step (in this case, step (n−1)), the length of the screening section corresponds to the length of the extension template sequence region for the previous step and, therefore, cannot be freely modified. In some embodiment, the length and sequence of the junction QC sequence region can be easily designed, independently of other design considerations, to control the melting temperature of the region of hybridization. For example, the length of the junction QC section (704) can be modified largely independent of other design considerations and can be as a variable to control the melting temperature of the hybridization section formed by (703) and (704). The same process can be carried out for sequences regions (713) and (714) of oligonucleotide (711). The length of the junction QC section (714) can be designed to precisely control the melting temperature of the hybridization section formed by (713) and (714). The same process can be carried out for every plurality of oligonucleotides immobilized at different features of the support.

In some embodiments, each support-bound oligonucleotide involved in the extension reactions is designed to have hybridization sections' melting temperatures (individual stringent melt temperatures) tuned towards the same target melting temperature (global stringent melt temperature). The individual stringent melt temperatures can be tuned as close to the global target as it is possible by increasing or decreasing the lengths of the individual junction QC sections. However, in some cases, it may not be possible to design oligonucleotides which individual stringent melt temperatures are the same as the global stringent melt temperature. In some embodiments, the support-bound oligonucleotides are designed to have an individual melt temperature to be within a defined range to the global stringent melt temperature. In some embodiments, the defined temperature range can be expressed as a temperature deviation from the target global stringent melt temperature, and can be of 0.001° C., 0.01° C., 0.1° C., 0.2° C., 0.3° C., 0.4° C., 0.5° C., 0.6° C., 0.7° C., 0.8° C., 0.9° C., 1° C., or less than 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 40° C.

Some aspects of the invention include a quality control step and/or quality control readout to identify the oligonucleotides or polynucleotides having the correct sequence. One skilled in the art would appreciate that after oligonucleotide assembly, the assembly product may contain a pool of sequences containing correct and incorrect assembly products. The errors may result from sequence errors introduced during the oligonucleotide synthesis, or during the assembly of oligonucleotides into longer nucleic acids. For example, up to 50% of the nucleic acid sequences may be unwanted sequences. Devices and methods to selectively isolate the correct nucleic acid sequence from the incorrect nucleic acid sequences are provided herein. The correct sequence may be isolated by selectively isolating the correct sequence from the other incorrect sequences as by selectively moving or transferring the desired assembled polynucleotide of predefined sequence to a different feature of the support. Alternatively, polynucleotides having an incorrect sequence can be selectively removed from the feature comprising the polynucleotide of interest. According to some methods of the invention, the assembly products may first be diluted onto the solid support in order to obtain a clonal population of oligonucleotides (i.e a population containing a single oligonucleotide sequence). As used herein, a "clonal nucleic acids" or "clonal population" or "clonal oligonucleotides" are used interchangeably and refer to a clonal molecular population of nucleic acids, i.e. to nucleic acids or oligonucleotides that are substantially or completely identical to each other. Accordingly, the dilution based protocol provides a population of nucleic acids or oligonucleotides (or polynucleotides) being substantially identical or identical to each other. In preferred embodiments, the oligonucleotides are diluted serially. In some embodiments, the device (for example, an array) integrates a serial dilution function. In some embodiments, the assembly product is serially diluted to a produce a clonal population of nucleic acids. Preferably, the concentration and the number of molecules is assessed prior to the dilution step and a dilution ratio is calculated in order to produce a clonal population. In an exemplary embodiment, the assembly product is diluted by a factor of at least 2, at least 3, at least 4, at least 5, at least 6, at least 7, at least 10, at least 20, at least 50, at least 100, at least 1,000 etc. . . . In preferred embodiment, the oligonucleotides or assembly products are first dried onto the support. The concentration of oligonucleotides may then be translated as a number of molecules per surface unit (for example, arbitrary surface unit). In some embodiments, a solid support surface may be divided into a plurality of spots or surface units and one or more spots or surface units may be hydrated (e.g. by dispensing one or more droplets). In an exemplary embodiment, oligonucleotides or assembly products are solubilized in a volume, for example a droplet or drop, having a specific footprint. The footprint of a droplet prior evaporation may comprise a number X of surface units or spots. The footprint may comprise, for example, at least 10, at least 20, at least 50, at least 200 spots or more spots or surface units. In some embodiments, a predefined number of the footprint spots are hydrated. In some embodiments, only one spot is hydrated resulting in a 1/Xs dilution of the oligonucleotide population. In an exemplary embodiment, the footprint comprises 100 spots and a single spot is hydrated, resulting in a 1/100 fold dilution ("diluted droplet"). The diluted droplet may be moved to a large footprint comprising 100 spots and the droplet volume is subsequently dried down. Continuing in a recursive manner, a single spot may be hydrated, resulting in an additional 1/100 dilution and consequently to a 1/10,000 final dilution. If a final dilution of 1/1,000,000 is needed to obtain a clonal population, the diluted droplet may be moved once more to a footprint comprising 100 spots, dried down and a single spot may be rehydrated. The steps of rehydration/moving may be repeated as many times it is necessary to get the desired clonal dilution. However, one skilled in the art would understand that a footprint comprising a large number of spots (e.g. 100 and more) may be surface consuming. It is therefore necessary to find a balance between the footprint size (or number of spots) and the dilution factor. For example, a dilution factor of 1,000,000 can be achieved by three serial dilutions of 1/100 (i.e. 300 spots or features) or by eight dilution of a factor of 1/7 (i.e. 94 spots of features). In other embodiments the entire footprint is hydrated and the droplet is split in two diluted droplet resulting in a concentration C/2. By continuing the dilution steps in the same manner, an exponential dilution of $2^Y$ can be obtained in Y steps. On would appreciate that the droplet may be split in at least 2, at least 5, at least 7, at least 10 resulting in an exponential dilution of at least $2^Y$, $5^y$, $7^y$ or $10^Y$.

Aspects of the invention relate to the sequence verification of a clonal population of oligonucleotides or a pool of oligonucleotides. In some embodiments, at least one quality control oligonucleotide (QC oligonucleotide) is designed to interrogate junction QC of a clonal population on an array. In some other embodiments, a plurality of QC oligonucleotides is designed to interrogate a plurality of sequences or junction QC sequences of an assembly product on a single feature of an array. For example, the junction quality control oligonucleotides are designed to interrogate assembly products that contain the (n), (n−1), (n−2) etc. . . . extension steps in one single QC reaction. In some embodiments, the oligonucleotides are designed to have a length from about 10 to about 50 bases, preferably from about 20 to about 50 bases, and more preferably from about 30 to about 45 bases to provide a useful sequence verification assay. The junction quality control oligonucleotides may be designed to have the same melting temperature. Alternatively, the junction quality control oligonucleotides are designed to have melting temperatures which are sufficiently different to be able to interrogate in a same volume different region of the assembly product. In some embodiments, cloning and quality control can be combined in one step. In some aspects of the invention, a pool of assembly products are interrogate without isolating a clonal population of oligonucleotides. Pool of assembly products may be interrogated serially on different features of the solid support, each feature comprising a different oligonucleotide designed for sequence verification. For example, quality control oligonucleotides can be spotted or synthesized on different features of the support. Preferably, the QC oligonucleotides are attached the support. After assembly, the product comprising a pool of different fragments can be interrogated at a first feature comprising an oligonucleotide designed to interrogate the first junction. Oligonucleotides that do not bind to the junction QC oligonucleotide are discarded (e.g. washed away), the duplexes can then be denatured and the assembly product may then be transferred to a second feature comprising a second junction QC oligonucleotides. Theses steps can be repeated until all junctions have been interrogated.

In some embodiments, the spacer section can be designed to extend the reactions away from the surface of the support, for example to limit steric hindrance during hybridization and extension (as shown in FIG. 7, spacer (705) and (715) extend away from the surface 700). In some embodiments, the spacer section can be used to adjust the overall length of the support-bound oligonucleotide template. For example, the spacer section (705) can be adjusted to control the total length of surface attached template (701). The spacer section can be used prior to the extension steps or after extension in a manner that does not interfere with the extension reactions. In some embodiments, the spacer region comprises a primer binding site. In other embodiments, the spacer region comprises a restriction enzyme site. In an exemplary embodiment, primers/primer binding sites may be designed to include a restriction endonuclease cleavage site. In an exemplary embodiment, a primer/primer binding site contains a binding and/or cleavage site for a type IIs restriction endonuclease. A wide variety of restriction endonucleases having specific binding and/or cleavage sites are commercially available, for example, from New England Biolabs (Beverly, Mass.). In various embodiments, restriction endonucleases that produce 3' overhangs, 5' overhangs or blunt ends may be used. When using a restriction endonuclease that produces an overhang, an exonuclease (e.g., RecJ$_f$, Exonuclease I, Exonuclease T, S$_1$ nuclease, P$_1$ nuclease, mung bean nuclease, T4 DNA polymerase, CEL I nuclease, etc.) may be used to produce blunt ends. Alternatively, the sticky ends formed by the specific restriction endonuclease may be used to facilitate assembly of subassemblies in a desired arrangement. In an exemplary embodiment, a primer/primer binding site that contains a binding and/or cleavage site for a type IIs restriction endonuclease may be used to remove the temporary primer. The term "type-IIs restriction endonuclease" refers to a restriction endonuclease having a non-palindromic recognition sequence and a cleavage site that occurs outside of the recognition site (e.g., from 0 to about 20 nucleotides distal to the recognition site). Type IIs restriction endonucleases may create a nick in a double-stranded nucleic acid molecule or may create a double-stranded break that produces either blunt or sticky ends (e.g., either 5' or 3' overhangs). Examples of Type IIs endonucleases include, for example, enzymes that produce a 3' overhang, such as, for example, Bsr I, Bsm I, BstF5 I, BsrD I, Bts I, Mnl I, BciV I, Hph I, Mbo II, Eci I, Acu I, Bpm I, Mme I, BsaX I, Bcg I, Bae I, Bfi I, TspDT I, TspGW I, Taq II, Eco57 I, Eco57M I, Gsu I, Ppi I, and Psr I; enzymes that produce a 5' overhang such as, for example, BsmA I, Ple I, Fau I, Sap I, BspM I, SfaN I, Hga I, Bvb I, Fok I, BceA I, BsmF I, Ksp632 I, Eco31 I, Esp3 I, Aar I; and enzymes that produce a blunt end, such as, for example, Mly I and Btr I. Type-IIs endonucleases are commercially available and are well known in the art (New England Biolabs, Beverly, Mass.).

Figure 8A:
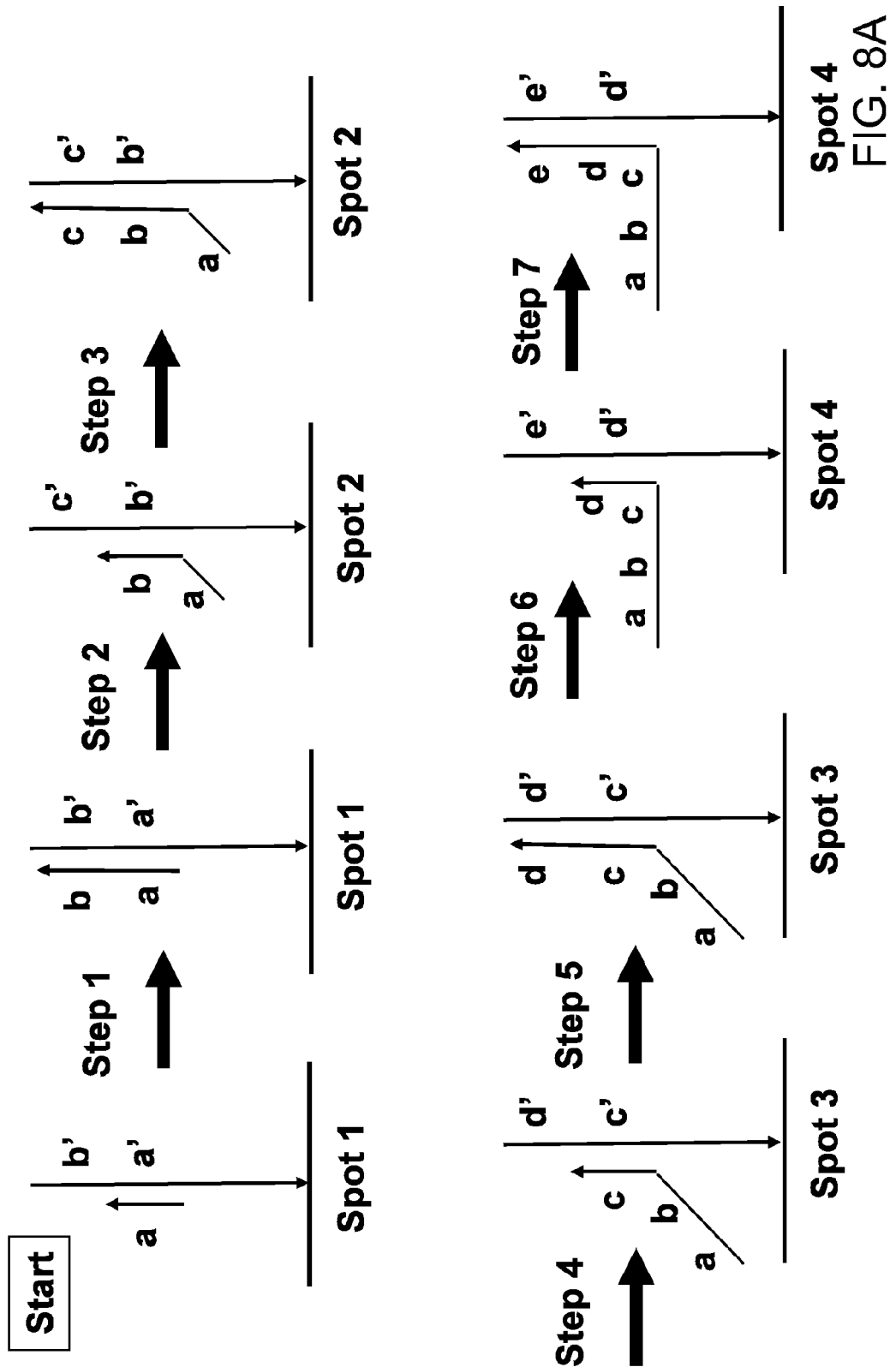
FIG. 8 illustrates a non-limiting exemplary method for double-stranded polynucleotide extension.
Figure 8B:
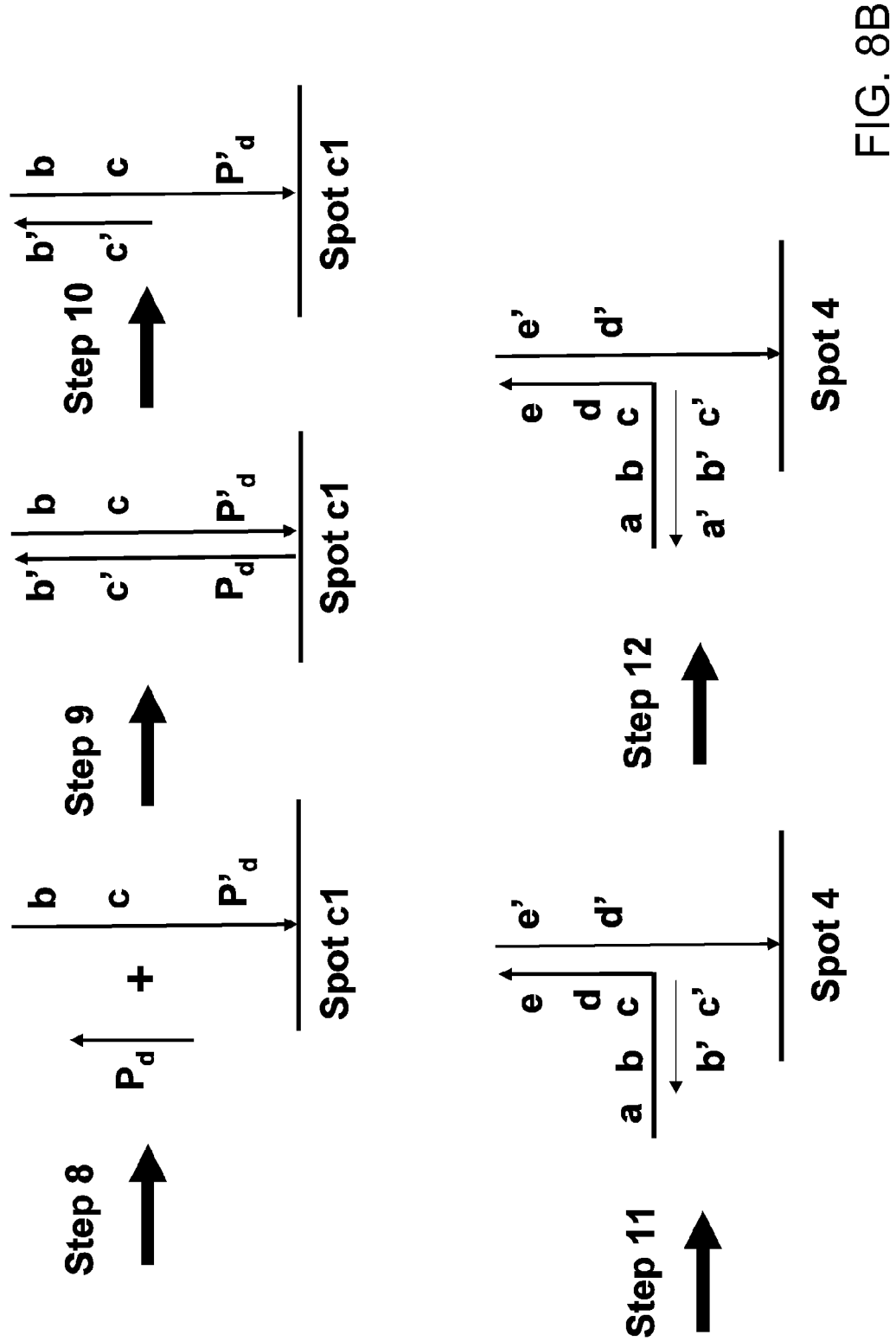

Some aspects of the invention relate to double-stranded polynucleotide synthesis. One should appreciate, that in certain instances it may be advantageous to build nucleic acids as double-stranded molecules. For example, oligonucleotides may adopt hairpin-like conformation if the oligonucleotide sequence contains self-complementary sequences, complicating the assembly reactions (ligation or extension) of oligonucleotides. Moreover, single-stranded nucleic acid sequences may be susceptible to be digested by exonucleases or other enzymes. In some embodiments, a polynucleotide is synthesized at a discrete feature of the support according to the methods disclosed above and an antisense oligonucleotide may be synthesized and annealed to the polynucleotide to protect the newly synthesized single-stranded polynucleotide. In some embodiments, the antisense or complementary oligonucleotide is synthesized at a discrete feature comprising an oligonucleotide designed to have a primer binding sequence and a sequence complementary to the single-stranded portion of the newly synthesized polynucleotide. For clarity, the two complementary strands of a double stranded nucleic acid are referred to herein as sense and antisense strands. This designation is not intended to imply that the strands are sense and anti-sense strands of a coding sequence. They refer only to the two complementary strands of a nucleic acid (e.g., predefined nucleic acid, predefined oligonucleotide, etc.) regardless of the sequence or function of the nucleic acid. Accordingly, a predefined nucleic acid sequence may be a sense strand, an antisense strand, or a double-stranded nucleic acid comprising both the sense and antisense strands. Referring to FIG. 8A, an oligonucleotide primer [a], designed to hybridize to a sequence region [a'] of a support-bound oligonucleotide on a first feature, is allows to hybridize to a first oligonucleotide on the first feature (Spot 1). In a first step (step 1, FIG. 8), the primer is extended in presence of appropriate polymerase (e.g. pfu) and dNTPs under appropriate extension conditions. Preferably, the polymerase has a 3'-5' exonuclease function such that a blunt end is formed with no additional base (e.g. adenosine) being added. Preferably, the polymerase is a pfu polymerase or a T4 DNA polymerase. In a second step (step 2), the newly synthesized extension product is melted. Melting of the duplex may be performed by increasing the temperature to a melting temperature (e.g. 95° C.). Alternatively, the duplex may be dissociated using an helicase. Helicase enzymes are know in the art and have been shown to unwind DNA from a double-strand structure to a single-strand structure. The single stranded extension product [ab] is transfered to a second feature (spot 2) comprising a second support-bound oligonucleotide, the second support-bound oligonucleotide sequence being different than the first oligonucleotide and partially complementary to extension product [ab]. The extension product is then allowed to hybridize under appropriate conditions to the second oligonucleotide at the second feature and to extend with addition of a polymerase and dNTPs (step 3). This process may be repeated through steps 4 to 7 to create a single stranded polynucleotide construct [abcde].

Aspects of the invention also relate to methods and devices for the synthesis or single-stranded nucleic acids and double-stranded nucleic acids. In some embodiments, single-stranded constructs are protected by generation of double-stranded polynucleotides. In some embodiments, plurality of surface-bound single-stranded oligonucleotides is provided at different features. In some aspects of the invention, the support comprises a plurality of extension features (on which the extension reactions take place) and a plurality of complementary features allowing the formation of double-stranded nucleic acids (double stranded oligonucleotides, double stranded polynucleotides). In an exemplary embodiment and referring to FIG. 8B, the newly synthesized single stranded construct [abcde] may be protected by formation of a double-stranded oligonucleotide (as shown in steps 8 through 10). In step 8, a primer is added to a feature comprising a single-stranded oligonucleotide having a sequence partially identical to the extension product. In a preferred embodiment, a primer P$_d$ containing multiple uracil or deoxy uridines (dU) are added at a feature on an array (referred herein as a complimentary feature or complementary spot, Spot c1). In a preferred embodiment, the complementary feature comprises support-bound single-stranded oligonucleotides having a primer binder region P$_d$' as well as sequence [bc]. In step 9, said primer P$_d$ is hybridized to the oligonucleotide and extended with the addition of dNTPs and an appropriate polymerase (e.g. pfu) under appropriate extension conditions. Preferable, the polymerase has a 3'-5' exonuclease function such that a blunt end is formed with no additional base (e.g. adenosine) being added (e.g. pfu, T4 DNA polymerase). In step 10, the USER™ enzyme (Uracil-Specific Excision Reagent, New England Biolabs) is added to digest the uracil containing primer P$_d$. The USER™ enzyme is a mixture of Uracil DNA glycosylase (UDG) and the DNA glycosylase-lyase Endonuclease VIII. The enzyme UDG catalyses the excision of a uracil base, forming an abasic (apyrimidinic) site while leaving the phosphodiester backbone intact. The lyase activity of Endonuclease VIII breaks the phosphodiester backbone at the 3' and 5' sides of the abasic site so that base-free deoxyribose is released. Digestion of the primer may be followed by a washing step to wash away enzymes and nucleotides not bound to surface features. In step 11, sequence [c'b'] is melted (either thermally or with by addition of a helicase) from the oligonucleotide on spot c1. The released [c'b'] sequence is then allowed to anneal to the extension product [abcde] from step 7 on a fourth feature (Spot 4). Sequence [c'b'] may then be extended to form [c'b'a'] thus protecting the growing single-stranded nucleic acid construct being generated during the synthesis process.

Figure 9A:
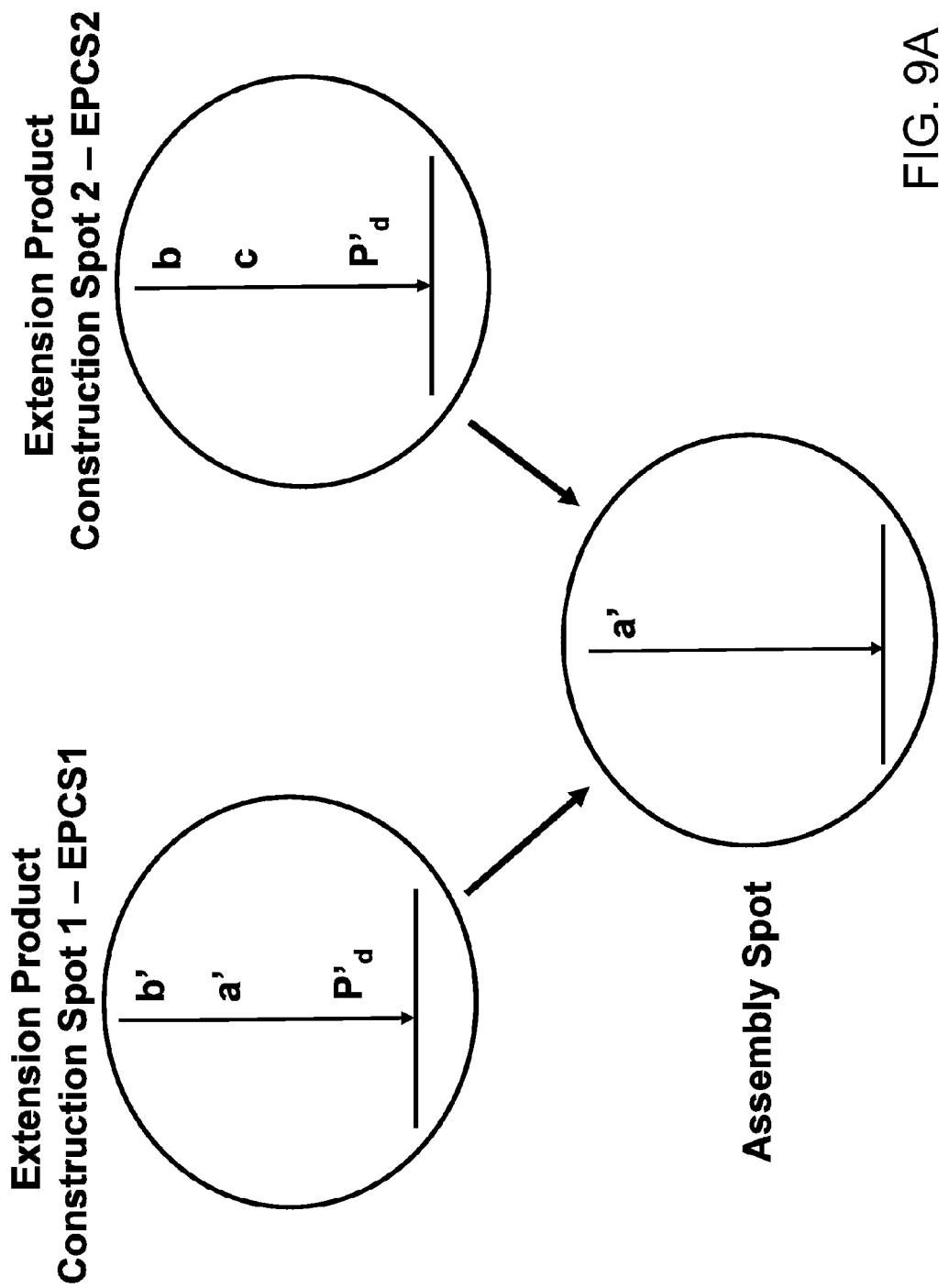
FIG. 9 illustrates a non-limiting exemplary method for double-stranded polynucleotide extension.
Figure 9B:
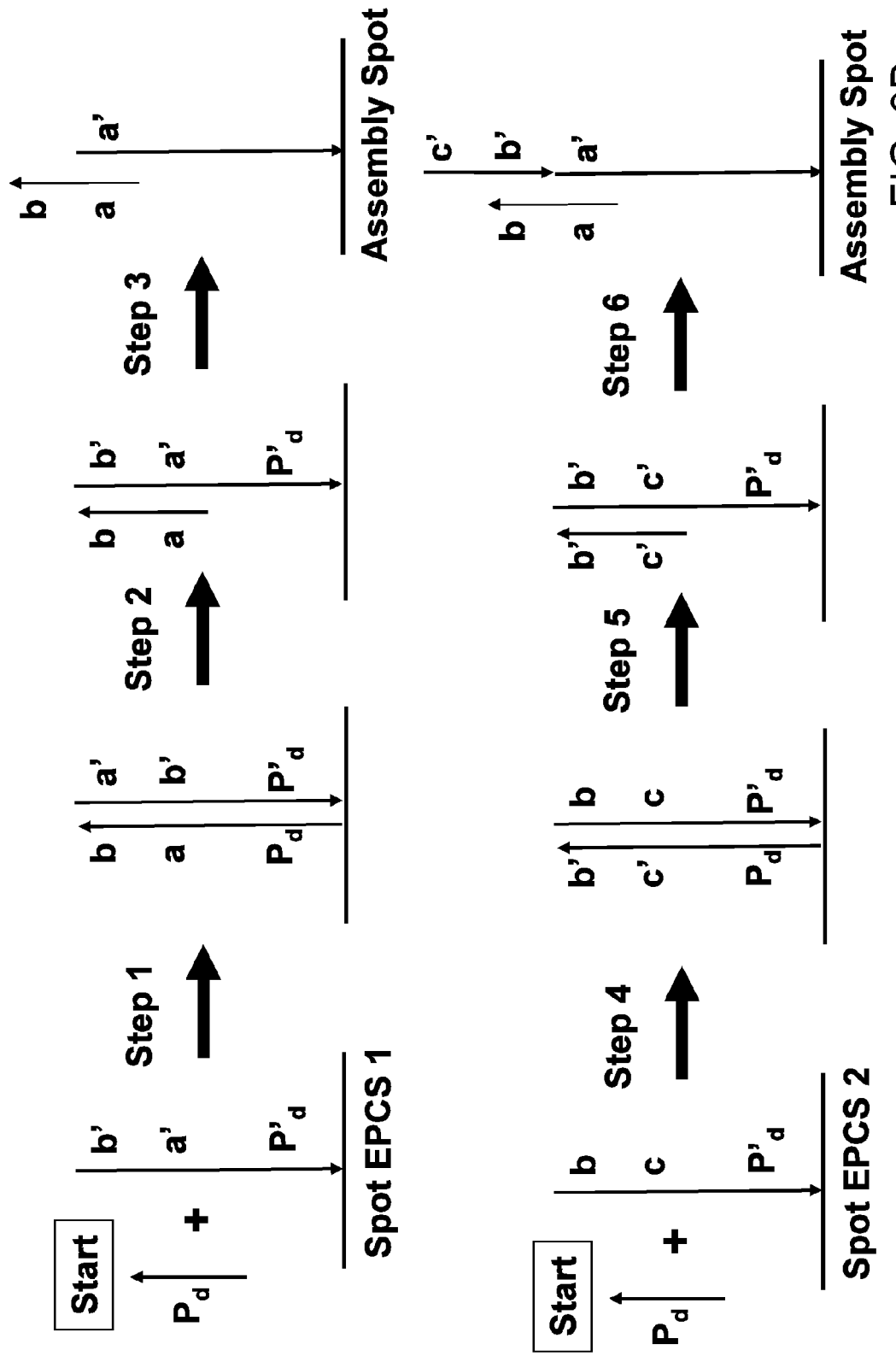

In some other aspects of the invention, methods and devices are provided to assemble predefined nucleic acid sequences, the method comprising synthesizing a plurality of construction oligonucleotides at different features of a support and assembling the construction oligonucleotides on an assembly oligonucleotide at a different discrete feature of the support. In some embodiments, the methods provide for the synthesis of construction oligonucleotides which may be assembled on an assembly feature of the support comprising a support-bound single-stranded anchor oligonucleotide. FIGS. 9A-B shows one embodiment of a plurality of different single-stranded support-bound oligonucleotides, the different oligonucleotides being bound at different features of the support. In some embodiments, the support comprises a plurality of extension product features (also referred herein as extension product construction spot) and at least one assembly feature (also referred herein as assembly spot). The extension product construction feature comprises a plurality of oligonucleotides which are designed to comprise a sequence complementary to a primer and a unique sequence which will act as a template for extension reaction to produce a construction oligonucleotide which will be used subsequently as part of the assembly reaction. The assembly feature comprises an anchor oligonucleotide on which the nucleic acid assembly will take place. FIG. 9A shows three different features on a support: an assembly spot and two extension product construction spots (EPCS1 and EPSC1). In preferred embodiments, the plurality of construction oligonucleotides have overlapping sequences that are mutually reverse complementary and the anchor oligonucleotide has a sequence that is reverse complementary to a first construction oligonucleotide. The construction oligonucleotides may therefore hybridize to one another and to the anchor oligonucleotide at the assembly spot under appropriate conditions and temperature. FIG. 9B illustrates the synthesis of the construction oligonucleotides and the assembly of the desired polynucleotide sequence. In some embodiments, the single-stranded oligonucleotides bound to the extension product construction spots are designed to comprise a sequence that is complementary to a primer sequence ($P'_d$) and a construction sequence [a' b']. Preferably, the primer is a primer containing multiple uracil (U) ($P_d$, FIG. 9B). The primer is first annealed to a single-stranded oligonucleotide at a first extension product construction spot EPCS1 and extended with the addition of dNTPs and an appropriate polymerase (e.g. pfu) under appropriate conditions and temperature. Preferably, the polymerase has a 3'-5' exonuclease function such that a blunt end is formed with no additional base (e.g. adenosine) being added. In a following step, the primer is removed (step 2). Preferably, an USER™ endonuclease is added to digest the primer $P_d$. This step may be followed by a washing step to wash away enzymes and nucleotides not bound to surface features. In step 3, extension product [ab] is melted (either thermally or with a helicase) and released into solution (e.g. into a droplet) and transferred to an assembly spot where it is hybridizes to the assembly anchor oligonucleotide under appropriate conditions and temperature. A similar process may be repeated with additional extension product construction spots (e.g. EPCS2 (as depicted in steps 4, 5 and 6)) in order to generate longer double-stranded nucleic acid constructs. Each internal construction oligonucleotide (e.g. [ab]) can hybridize to two other complementary oligonucleotides (construction oligonucleotides or construction oligonucleotide and anchor assembly oligonucleotide as illustrate in FIG. 9B) and the construction oligonucleotides may be joined by polymerase extension or ligation reactions. In some embodiments, hybridization of construction oligonucleotides to the anchor oligonucleotide is performed at a temperature at which hybridization of pairs of overlap sequences that are exactly reverse complementary is able to occur more readily than hybridization involving incorrect sequences.

Figure 10A:
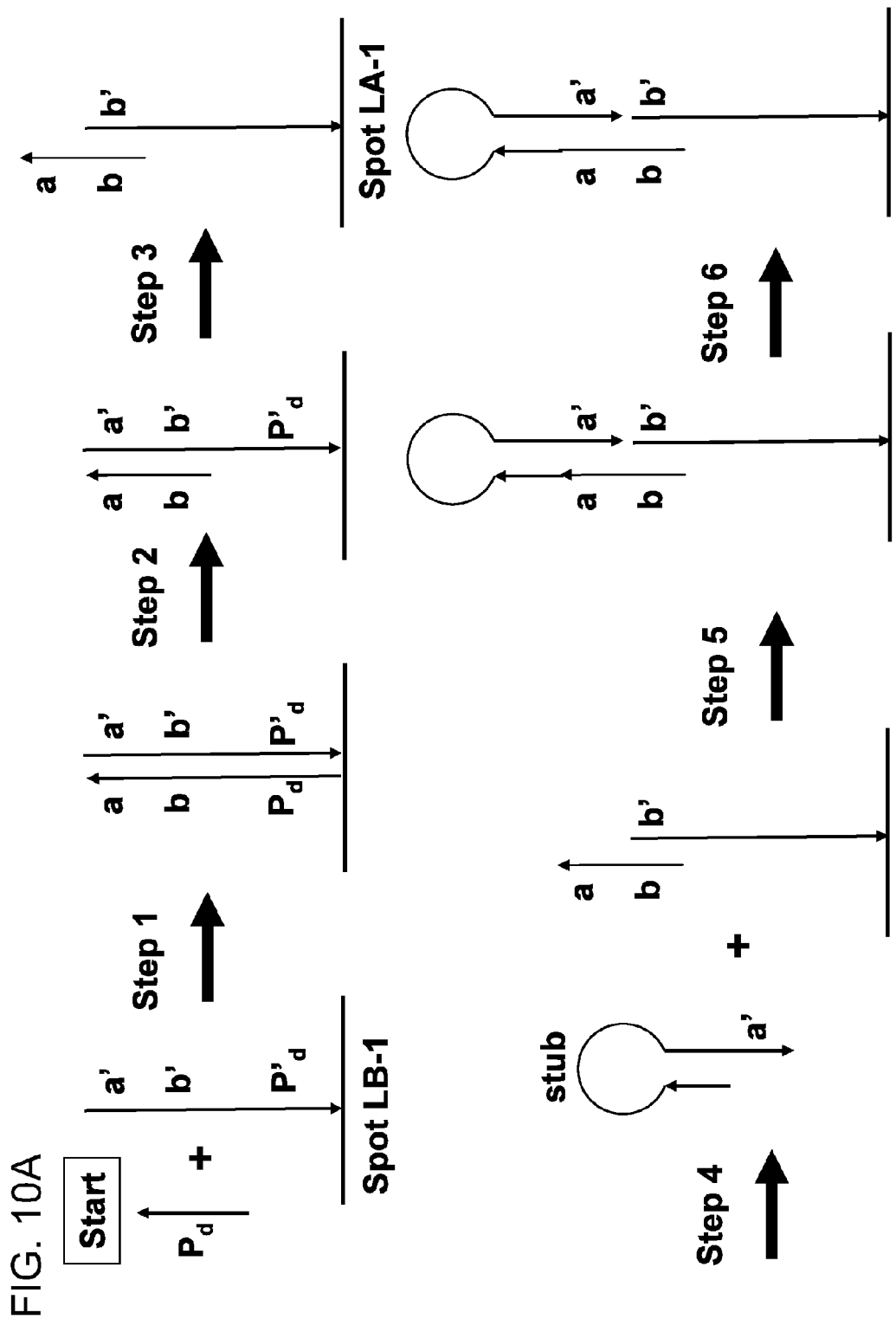
FIG. 10 illustrates a non-limiting exemplary method for double-stranded polynucleotide extension in a single pool.
Figure 10B:
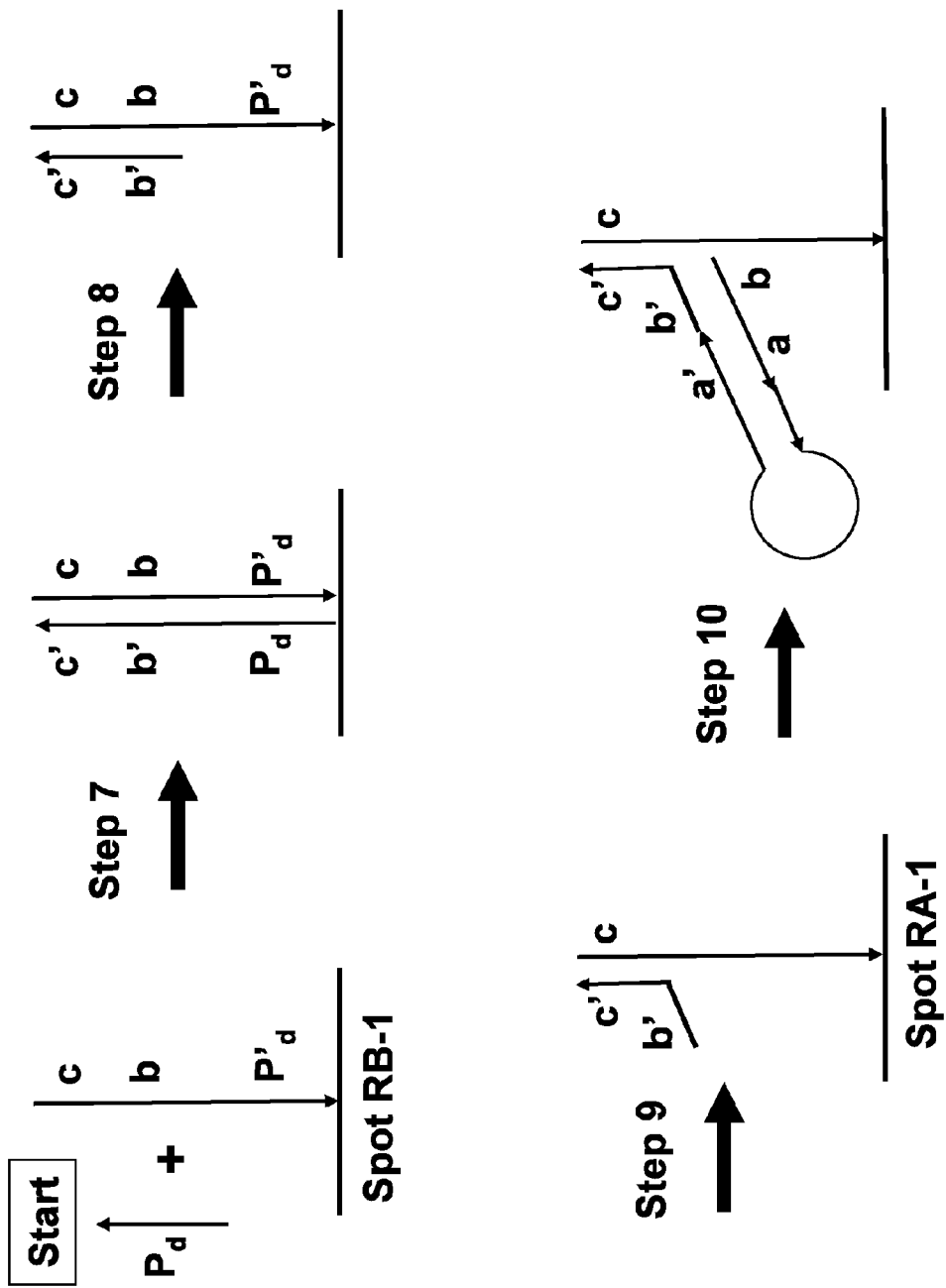

In some embodiments, the predefined nucleic acid is synthesized as a double-stranded nucleic acid having a stem-loop structure. In some embodiments, in a first step a complementary oligonucleotide [ab] is synthesized using a support-bound single-stranded oligonucleotide as template. In an exemplary embodiment, the complementary oligonucleotide is designed to have a primer binding region at the 3' end. A primer is added at a first feature comprising the complementary oligonucleotide and allowed to extend under appropriate conditions to produce an extension product. Preferably, the primer contains multiple uracil (dU). Referring to FIG. 10A, the primer $P_d$ is added to a first feature (Left Build spot, LB-1) containing an oligonucleotide which has a primer binder region $P'_d$ as well as construction sequence regions [a' b']. Referring to step 1, the primer ($P_d$) is hybridized the oligonucleotide on feature LB-1 and extended with the addition of dNTPs and an appropriate polymerase (e.g. pfu) under appropriate reaction conditions and temperature. Preferably, the polymerase has a 3'-5' exonuclease function such that a blunt end is formed and no addition base (e.g. adenosine) is added. Referring step 2, the primer is removed or digested. In some embodiments, an USER™ endonuclease is added to digest primer $P_d$. Referring to step 3, extension product [ab] is melted (either thermally or with a helicase) and released into solution (e.g. into a droplet) and transferred to a second feature (left anchor LA-1, FIG. 10A). Referring to step 4, a construction stem-loop oligonucleotide (also referred herein as loop stub) is added. The stem-loop oligonucleotide may have a right sided 3' overhang [a'] which is complimentary to the sequence [a] of the extension product [ab]. The stem-loop structure (also known as hairpin) may be formed by designing the oligonucleotide to have complementary sequences within its single-stranded sequence whereby a single strand folds back upon itself to form a double-stranded stem and a single-stranded loop. Preferably, the double-stranded stem domain has at least about 2 base pairs and the single stranded loop has at least 3 nucleotides. Preferably, the stem comprises an overhanging single-stranded region (3' or 5'), i.e., the stem is a partial duplex. For example, the overhang can be from about 3 to about 10 to about 20, to about 50, etc. . . . nucleotides. The construction stem-loop stub is hybridized onto the second feature (Spot LA-1, FIG. 10A) to form a hybridization product comprising a stem-loop structure as depicted in steps 5 and 6. In some embodiments, the 3' end of the stem-loop stub structure has a gap with the 5' end of a consecutive oligonucleotide and the abutting 5' end of the stub structure and 3' end of an extension product are ligated. For example, referring to FIG. 10A, the 3' end of the stub structure with sequence [a'] has a gap and is discontinuous with the 5' end of the oligonucleotide comprising the [b'] sequence (at LA-1). In step 6, a ligase is added to ligate the construction 3' end of the extension product [ab] to the 5' end of the stub structure thereby forming an assembly polynucleotide construct comprising a stem-loop structure. In some embodiments, a second extension product [b'c'] is synthesized on a third feature (spot RB-1) then transferred and hybridized to an anchor support-bound single stranded oligonucleotide at a fourth feature of the support, the anchor oligonucleotide comprising a sequence that is complementary to the second extension product. The extension product can be further extended by addition of the polynucleotide construct comprising the stem-loop structure by ligation. Steps may be repeated in order to synthesize the double-stranded predefined nucleic acid sequence. FIG. 10B illustrates the different steps. Referring to FIG. 10B, a primer $P_d$ is added to feature spot RB-1 comprising an oligonucleotide having a primer binding site ($P'_d$) and the construction sequence [bc]. The primer is annealed and extended under the appropriate extension conditions by addition of a polymerase and dNTPs to produce the extension product [cd] (step 7). Referring to step 8, the primer is removed using for example an USER™ endonuclease. An optional washing step may be performed. Referring to step 9, extension product [c'b'] is melted (either thermally or with a helicase) and released into solution (e.g. a droplet) and transferred to another feature (spot right anchor RA-1), thereby bringing into contact the extension product [c'd'] with an anchor oligonucleotide comprising a sequence complementary to sequence [c']. Referring to step 10, the construction loop from step 6 is hybridized to [b'] sequence of the duplex, the 5' overhang [b] being complementary to sequence [b'] of the [c'b'] extension product. The oligonucleotide [c'b'] may then be ligated to the elongated construction stem-loop polynucleotide. Steps 1 through 10 may be repeated with different construction features and anchor features in order elongate the double-stranded nucleic acid constructs thereby producing the predefined nucleic acid sequence.

In some embodiments, after extension or amplification, the polymerase may be deactivated to prevent interference with the subsequent steps. A heating step (e.g., high temperature) can denature and deactivate most enzymes which are not thermally stable. Enzymes may be deactivated in presence (e.g., within the droplet) or in the absence of liquid (e.g., dry array). Heat deactivation on a dry support has the advantage to deactivate the enzymes without any detrimental effect on the oligonucleotides. In some embodiments, a non-thermal stable version of the thermally stable PCR DNA Polymerase may be used, although the enzyme is less optimized for error rate and speed. Alternatively, Epoxy dATP can be use to inactivate the enzyme.

It should be appreciated that the description of the assembly reactions in the context of oligonucleotides is not intended to be limiting. For example, other polynucleotides (e.g., single-stranded, double-stranded polynucleotides, restriction fragments, amplification products, naturally occurring polynucleotides, etc.) may be included in an assembly reaction, along with one or more oligonucleotides, in order to generate a polynucleotide of interest.

Aspects of the invention may be useful for a range of applications involving the production and/or use of synthetic nucleic acids. As described herein, the invention provides methods for producing synthetic nucleic acids with increased fidelity and/or for reducing the cost and/or time of synthetic assembly reactions. The resulting assembled nucleic acids may be amplified in vitro (e.g., using PCR, LCR, or any suitable amplification technique), amplified in vivo (e.g., via cloning into a suitable vector), isolated and/or purified. An assembled nucleic acid (alone or cloned into a vector) may be transformed into a host cell (e.g., a prokaryotic, eukaryotic, insect, mammalian, or other host cell). In some embodiments, the host cell may be used to propagate the nucleic acid. In certain embodiments, the nucleic acid may be integrated into the genome of the host cell. In some embodiments, the nucleic acid may replace a corresponding nucleic acid region on the genome of the cell (e.g., via homologous recombination). Accordingly, nucleic acids may be used to produce recombinant organisms. In some embodiments, a target nucleic acid may be an entire genome or large fragments of a genome that are used to replace all or part of the genome of a host organism. Recombinant organisms also may be used for a variety of research, industrial, agricultural, and/or medical applications.

In some embodiments, methods described herein may be used during the assembly of large nucleic acid molecules (for example, larger than 5,000 nucleotides in length, e.g., longer than about 10,000, longer than about 25,000, longer than about 50,000, longer than about 75,000, longer than about 100,000 nucleotides, etc.). In an exemplary embodiment, methods described herein may be used during the assembly of an entire genome (or a large fragment thereof, e.g., about 10%, 20%, 30%, 40%, 50%, 60%, 70%, 80%, 90%, or more) of an organism (e.g., of a viral, bacterial, yeast, or other prokaryotic or eukaryotic organism), optionally incorporating specific modifications into the sequence at one or more desired locations.

Aspects of the methods and devices provided herein may include automating one or more acts described herein. In some embodiments, one or more steps of an amplification and/or assembly reaction may be automated using one or more automated sample handling devices (e.g., one or more automated liquid or fluid handling devices). Automated devices and procedures may be used to deliver reaction reagents, including one or more of the following: starting nucleic acids, buffers, enzymes (e.g., one or more ligases and/or polymerases), nucleotides, salts, and any other suitable agents such as stabilizing agents. Automated devices and procedures also may be used to control the reaction conditions. For example, an automated thermal cycler may be used to control reaction temperatures and any temperature cycles that may be used. In some embodiments, a scanning laser may be automated to provide one or more reaction temperatures or temperature cycles suitable for incubating polynucleotides. Similarly, subsequent analysis of assembled polynucleotide products may be automated. For example, sequencing may be automated using a sequencing device and automated sequencing protocols. Additional steps (e.g., amplification, cloning, etc.) also may be automated using one or more appropriate devices and related protocols. It should be appreciated that one or more of the device or device components described herein may be combined in a system (e.g., a robotic system) or in a micro-environment (e.g., a micro-fluidic reaction chamber). Assembly reaction mixtures (e.g., liquid reaction samples) may be transferred from one component of the system to another using automated devices and procedures (e.g., robotic manipulation and/or transfer of samples and/or sample containers, including automated pipetting devices, micro-systems, etc.). The system and any components thereof may be controlled by a control system.

Accordingly, method steps and/or aspects of the devices provided herein may be automated using, for example, a computer system (e.g., a computer controlled system). A computer system on which aspects of the technology provided herein can be implemented may include a computer for any type of processing (e.g., sequence analysis and/or automated device control as described herein). However, it should be appreciated that certain processing steps may be provided by one or more of the automated devices that are part of the assembly system. In some embodiments, a computer system may include two or more computers. For example, one computer may be coupled, via a network, to a second computer. One computer may perform sequence analysis. The second computer may control one or more of the automated synthesis and assembly devices in the system. In other aspects, additional computers may be included in the network to control one or more of the analysis or processing acts. Each computer may include a memory and processor. The computers can take any form, as the aspects of the technology provided herein are not limited to being implemented on any particular computer platform. Similarly, the network can take any form, including a private network or a public network (e.g., the Internet). Display devices can be associated with one or more of the devices and computers. Alternatively, or in addition, a display device may be located at a remote site and connected for displaying the output of an analysis in accordance with the technology provided herein. Connections between the different components of the system may be via wire, optical fiber, wireless transmission, satellite transmission, any other suitable transmission, or any combination of two or more of the above.

Each of the different aspects, embodiments, or acts of the technology provided herein can be independently automated and implemented in any of numerous ways. For example, each aspect, embodiment, or act can be independently implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments of the technology provided herein comprises at least one computer-readable medium (e.g., a computer memory, a floppy disk, a compact disk, a tape, etc.) encoded with a computer program (i.e., a plurality of instructions), which, when executed on a processor, performs one or more of the above-discussed functions of the technology provided herein. The computer-readable medium can be transportable such that the program stored thereon can be loaded onto any computer system resource to implement one or more functions of the technology provided herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the technology provided herein.

It should be appreciated that in accordance with several embodiments of the technology provided herein wherein processes are stored in a computer readable medium, the computer implemented processes may, during the course of their execution, receive input manually (e.g., from a user).

Accordingly, overall system-level control of the assembly devices or components described herein may be performed by a system controller which may provide control signals to the associated nucleic acid synthesizers, liquid handling devices, thermal cyclers, sequencing devices, associated robotic components, as well as other suitable systems for performing the desired input/output or other control functions. Thus, the system controller along with any device controllers together form a controller that controls the operation of a nucleic acid assembly system. The controller may include a general purpose data processing system, which can be a general purpose computer, or network of general purpose computers, and other associated devices, including communications devices, modems, and/or other circuitry or components to perform the desired input/output or other functions. The controller can also be implemented, at least in part, as a single special purpose integrated circuit (e.g., ASIC) or an array of ASICs, each having a main or central processor section for overall, system-level control, and separate sections dedicated to performing various different specific computations, functions and other processes under the control of the central processor section. The controller can also be implemented using a plurality of separate dedicated programmable integrated or other electronic circuits or devices, e.g., hard wired electronic or logic circuits such as discrete element circuits or programmable logic devices. The controller can also include any other components or devices, such as user input/output devices (monitors, displays, printers, a keyboard, a user pointing device, touch screen, or other user interface, etc.), data storage devices, drive motors, linkages, valve controllers, robotic devices, vacuum and other pumps, pressure sensors, detectors, power supplies, pulse sources, communication devices or other electronic circuitry or components, and so on. The controller also may control operation of other portions of a system, such as automated client order processing, quality control, packaging, shipping, billing, etc., to perform other suitable functions known in the art but not described in detail herein.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EXAMPLE

Figure 11A:
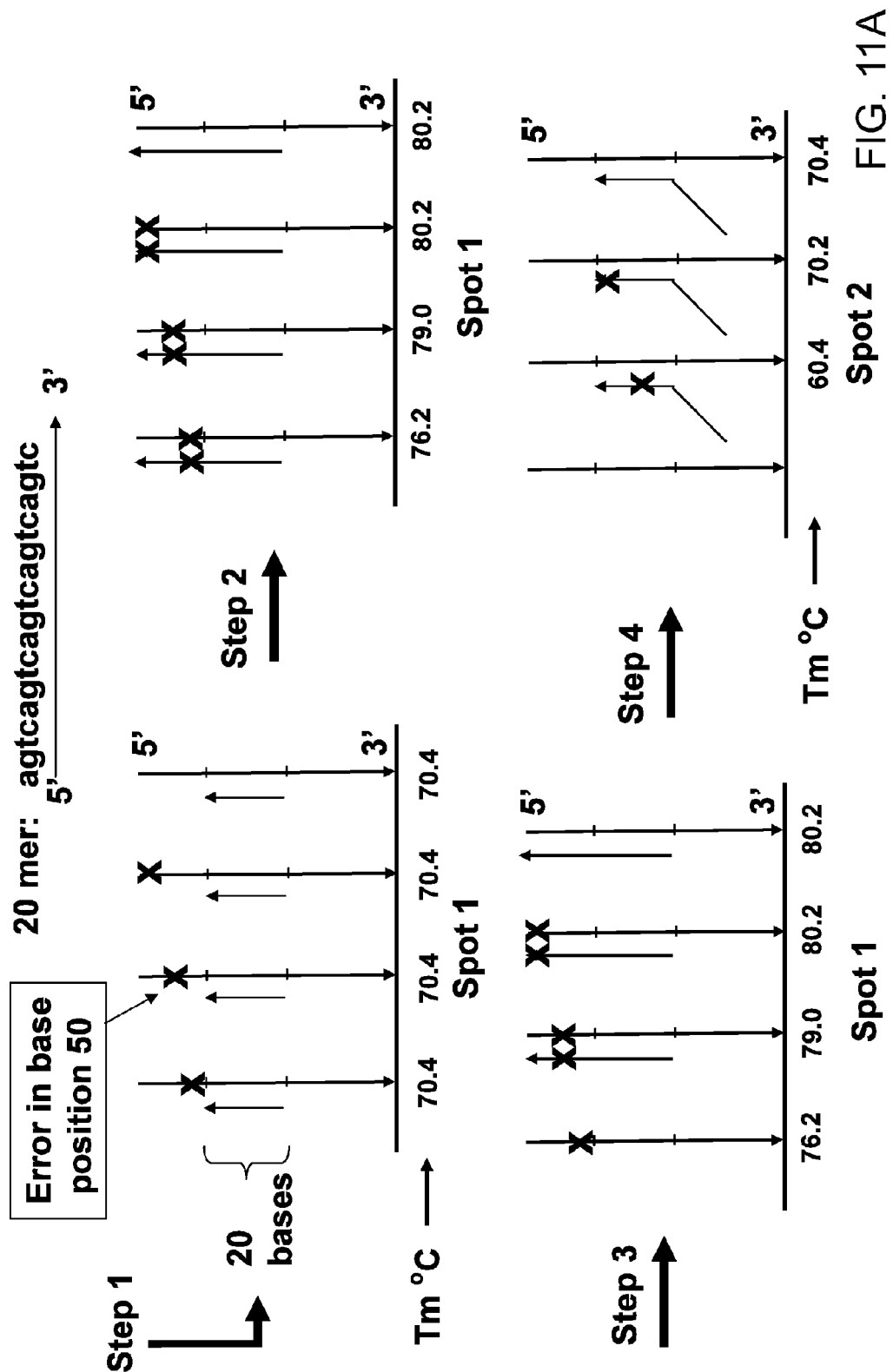
FIG. 11 illustrates a non-limiting quantitative example of error correction with stringent melt using two different temperatures.

Referring to FIG. 11, a quantitative example is given for carrying out error correction in the context of nucleic acid synthesis by means of using a double stringent melt at two different temperatures. This process is aimed at diminishing errors both in the middle of the extension product and at the ends of the extension product. The 20 mer initial seed oligonucleotide SEQ ID NO 1 agtcagtcagtcagtcagtc (5'→3'), is hybridized to spot 1 array features in Step 1 as shown in FIG. 11A. The seed oligonucleotide is hybridized under the following salt conditions: 10 mM Na, 5 mM Mg. The oligonucleotide concentration is 17 micromolar as meant to simulate the conditions of a DNA array being addressed with ink jet droplets of volume 10 pL. Calculations are carried out using algorithms for nucleic acid hybridization (See Markham, N. R. & Zuker, M. (2005) DINAMelt web server for nucleic acid melting prediction. Nucleic Acids Res., 33, W577-W581.

In Step 1, a 20 mer seed primer is introduced to a first features (spot 1) comprising support-bound 60 mer oligonucleotides. The 20 mer seed oligonucleotide is designed to hybridize to the middle 20 mer region of the 60 mer (FIG. 11A). The oligonucleotides on the first features (spot 1) are assumed to contain errors which may have arisen from oligonucleotide array synthesis. Errors are depicted with cross as occurring in different regions, namely in base position 41, 50 and 60 from the 3' end of the array surface. The oligonucleotides on the last feature are shown without error.

In step 2, the hybridized 20 mer is extended by means of a blunt end polymerase (e.g. pfu) and dNTPs under appropriate extension conditions. The polymerase is assumed to faithfully copy errors as shown. The melting temperatures of the resulting extension products are shown under each oligonucleotide (Tm, ° C.). Referring to FIG. 11A, errors in the middle of the extension product can be distinguished from a error-free extension product by several degrees in the melting transition temperature. Therefore, error-containing extension product will melt at a temperature between 76.2° C. and 80.2° C. In an exemplary embodiment, the support is heated to temperature above the melting temperature just below the temperature of the error-free extension product. In this example, the support is heated at a temperature below 80.2° C. in order to melt off strands which contain errors in the middle portion without melting the error-free extension products.

Step 3 shows the first feature (spot 1) after elevating the temperature at a melting temperature above 76.2° C. and below 79.0° C. As seen on FIG. 11A, errors located towards the 3' end of the extension product are not discriminated against the error-free extension product and these error-containing extension products will remain.

The extension products are subjected to stringent melt conditions (step 3) and released at the first feature. The released extension products are moved from a first feature to a second feature (spot 2, FIG. 11A) and hybridized to the support-bound oligonucleotides at the second feature. By design, the 20 bases sequence at the 3' end of the extension product is complimentary to the 20 bases middle sequence of the support-bound oligonucleotides at the second feature (spot 2). The difference in melting temperature of the resulting error-containing duplexes compared to the error-free duplex is larger on the second feature than when compared to the first feature (e.g. 60.4° C. vs. 70.4° C. on the second feature compared to 79.0° C. vs. 80.2° C. on the first feature).

Figure 11B:
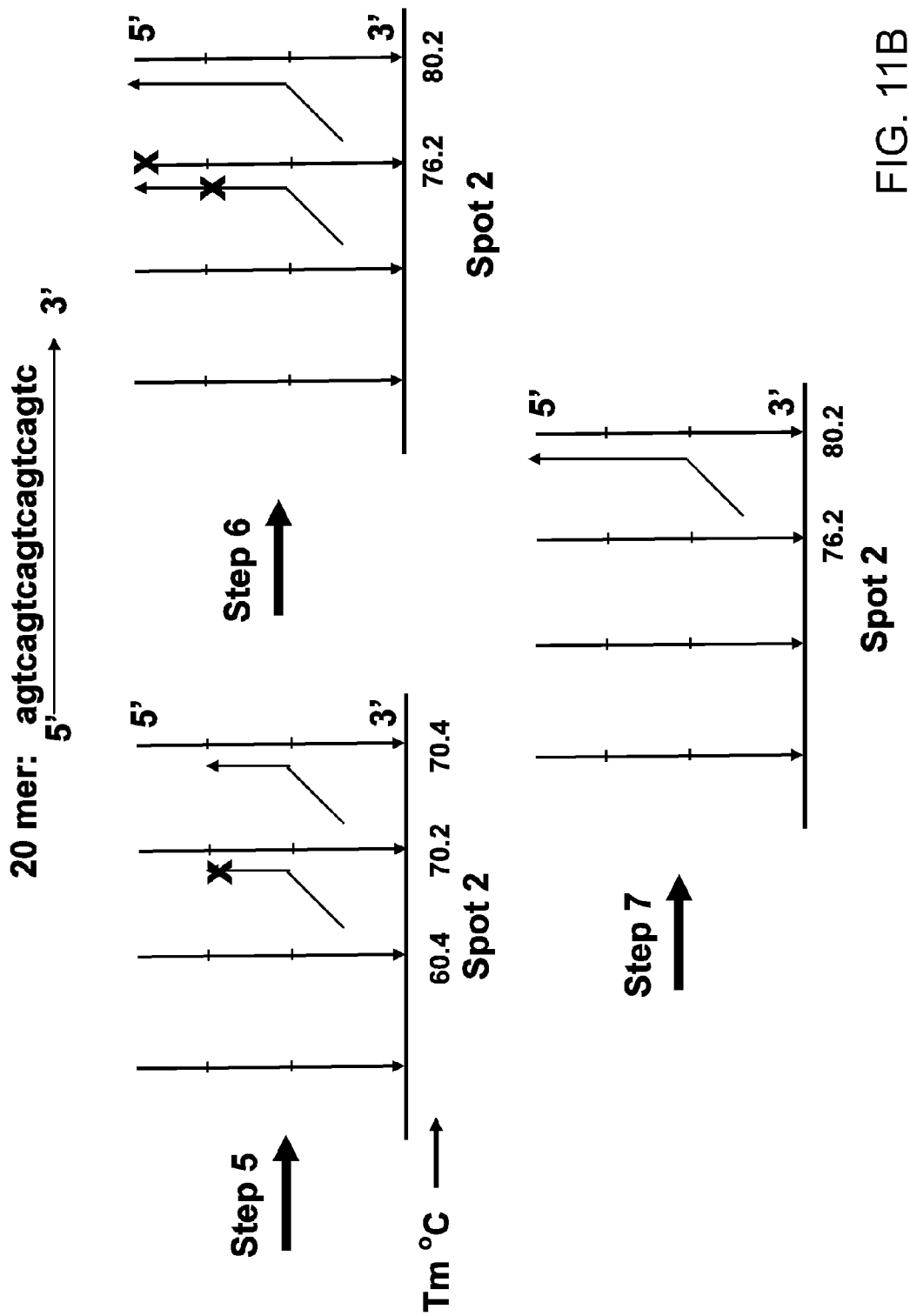

Step 5, shows the resulting second feature (spot 2) after melting at a temperature above 60.4° C. and below 70.2° C. (FIG. 11B). As shown previously, errors towards the 3' end of the extension product are not discriminated against the perfect product and will remain.

In step 6, extension is carried out by means of a blunt end polymerase (e.g. pfu) and dNTPs under the appropriate extension conditions. The melting temperatures of the resulting extension products are shown under each oligonucleotide (Tm, ° C.). Errors in the middle of the extension product can be distinguished from an error-free extension product by several degrees in the melting transition temperature. Therefore, error-containing extension product will melt at a temperature between 76.2° C. and 80.2° C. In an exemplary embodiment, the support is heated to temperature above the melting temperature just below the temperature of the error-free extension product. In this example, the support is heated at a temperature below 80.2° C. in order to melt off strands which contain errors in the middle portion without melting the error-free extension products (Step 7).

EQUIVALENTS

The present invention provides among other things novel methods and devices for high-fidelity gene assembly. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

Reference is made to PCT application numbers PCT/US2009/055267 (publication number WO 2010/025310), PCT/US2007/011886 (publication number WO 2007/136736); PCT/US2010/055298, PCT/US2010/057405, to U.S. Pat. No. 7,183,406 entitled "Methods for the synthesis of DNA sequences"; to U.S. Provisional application 61/257,591 filed Nov. 3, 2009; to U.S. Provisional application 61/264,643, filed on Nov. 25, 2009; to U.S. Provisional Application 61/264,632 filed on Nov. 25, 2009; to U.S. provisional application 61/264,641 entitled; to U.S. Provisional Application 61/293,192, filed on Jan. 7, 2010; to U.S. Provisional Application 61/310,076 filed on Mar. 3, 2010; and to U.S. Provisional Application 61/310,100 filed Mar. 3, 2010. All publications, patents, patent applications, and sequence database entries mentioned herein are hereby incorporated by reference in their entirety as if each individual publication or patent was specifically and individually indicated to be incorporated by reference.

What is claimed is:

1. A method for producing at least one polynucleotide having a predefined sequence, the method comprising the steps of:
   (a) providing a support having a plurality of discrete addressable features at predetermined locations of the support, the support comprising at least a first plurality of support-bound oligonucleotides at a first feature and a second plurality of support-bound oligonucleotides at a second feature, wherein the first and second pluralities of support-bound oligonucleotides are single-stranded oligonucleotides and have different predefined sequences, and the first plurality of support-bound oligonucleotides comprises a sequence region at its 5' end that is the same as a sequence region of a 3' end of the second plurality of support-bound oligonucleotides;
   (b) providing a plurality single-stranded oligonucleotides, wherein the 3' end of the plurality of the single-stranded oligonucleotides is complementary to the 3' end of the first plurality of support-bound oligonucleotides at selected addressable features;
   (c) hybridizing the plurality of single-stranded oligonucleotides to the first plurality of support-bound oligonucleotides at the first feature;
   (d) subjecting the plurality of single-stranded oligonucleotides to a chain extension reaction, thereby forming double-stranded extension products;
   (e) dissociating the double-stranded extension products, thereby producing a first plurality of single-stranded complementary oligonucleotides;
   (f) transferring, in a predetermined order, the first plurality of single-stranded complementary oligonucleotides in droplet volume from the first feature at a first predetermined location to the second feature at a second predetermined location of the support, thereby bringing into contact the first plurality of single-stranded complementary oligonucleotides with the second plurality of support-bound oligonucleotides;
   (g) annealing the first plurality of single-stranded complementary oligonucleotides to the second plurality of support-bound oligonucleotides at the second feature such that the second plurality of support-bound oligonucleotides serves as a template for extension of the first plurality of complementary oligonucleotides in a chain extension reaction, thereby producing the polynucleotide; and
   (h) optionally amplifying the polynucleotide.

2. The method of claim 1 further sequentially repeating steps (c) through (g) using at least a third plurality of support-bound oligonucleotides, wherein each plurality of support-bound oligonucleotides comprises a sequence region at its 3' end that is the same as a sequence region of a 5' end of a next plurality of oligonucleotides, and wherein the third plurality of support-bound oligonucleotides are single-stranded oligonucleotides, thereby producing a longer polynucleotide.

3. The method of claim 1 wherein steps (b) through (e) are performed within a droplet volume of solution at the first feature thereby releasing the first plurality of single-stranded complementary oligonucleotides in the droplet volume of solution and transferring the droplet volume of solution to the second feature comprising the second plurality of support-bound oligonucleotides.

4. The method of claim 3 wherein the droplet volume of solution is transferred from the first feature to the second feature by electrowetting, temperature gradients, wettability gradients, mechanical force or any combination thereof.

5. A method for producing at least one high fidelity target polynucleotide having a predefined sequence, the method comprising the steps of:
   (a) providing a support having a plurality of discrete addressable features at predetermined locations of the support, the support comprising at least a first plurality of support-bound oligonucleotides at a first feature and a second plurality of support-bound oligonucleotides at a second feature, the first plurality of support-bound oligonucleotides having a predefined sequence and the second plurality of support-bound oligonucleotides having a different predefined sequence,
       wherein the first plurality of support-bound oligonucleotides has a sequence region at its 5' end that is the same as a sequence region of the 3' end of the second plurality of support-bound oligonucleotides, and
       wherein the first and second pluralities of support-bound oligonucleotides are single-stranded oligonucleotides,
   (b) hybridizing a first plurality of single-stranded polynucleotides in solution with the first plurality of support-bound oligonucleotides at the first feature under hybridizing conditions thereby forming partially double-stranded polynucleotides, wherein the first plurality of single-stranded polynucleotides has a 3' end that is complementary to the 3' end of the first plurality of support-bound oligonucleotides;
   (c) subjecting the partially double-stranded polynucleotides to a stringent wash under conditions sufficient to denature the partially double-stranded polynucleotides having at least one mismatch in a complementary region without denaturing the partially double-stranded polynucleotides that do not comprise a mismatch in the complementary region, thereby releasing error-containing single-stranded polynucleotides in solution;
   (d) removing the error-containing single-stranded polynucleotides;
   (e) subjecting the partially double-stranded polynucleotides to a chain extension reaction under conditions promoting extension of the partially double-stranded polynucleotides, thereby forming extension double-stranded products;
   (f) dissociating the extension double-stranded products, thereby releasing a second plurality of single-stranded polynucleotides in solution;
   (g) transferring, in a predetermined order, the second plurality of single-stranded polynucleotides in droplet volume from the first feature to the second feature and annealing the second plurality of single-stranded polynucleotides to the second plurality of support-bound oligonucleotides at the second feature of the support, wherein the second plurality of single-stranded polynucleotides has a 3' end that is complementary to the 3' end of the second plurality of support-bound oligonucleotides; and (h) optionally repeating the cycles of stringent wash, extension, dissociation and annealing until the target polynucleotide is synthesized.

6. The method of claim 5
wherein steps (b) through (d) are performed within a first droplet volume of solution at the first feature,
wherein step (d) is performed by removing the first droplet volume of solution,
wherein steps (e) and (f) are performed within a second droplet volume of solution at the first feature, thereby releasing the second plurality of single-stranded polynucleotides in the second droplet volume of solution, and
wherein step (g) comprises transferring the second droplet volume of solution to the second feature comprising the second plurality of support-bound oligonucleotides.

7. The method of claim 6 wherein the first droplet volume of solution is subjected first to annealing conditions and second to stringent wash and wherein the second droplet volume of solution is subjected to conditions promoting primer extension.

8. A method for producing at least one high fidelity target polynucleotide having a predefined sequence, the method comprising the steps of:
(a) providing a support having a plurality of discrete addressable features at predetermined locations of the support, the support comprising at least a first plurality of support-bound oligonucleotides at a first feature and a second plurality of support-bound oligonucleotides at a second feature, each plurality of support-bound oligonucleotides having a different predefined sequence,
wherein the first plurality of support-bound oligonucleotides has at least a 5' end sequence region N, a sequence regions (N−1) and a sequence region (N−2), and a 3' end sequence region, and
wherein the first and second pluralities of support-bound oligonucleotides are single-stranded oligonucleotides,
(b) providing a first plurality of single-stranded polynucleotides in solution at the first feature comprising the first plurality of support-bound oligonucleotides, wherein the first plurality of single-stranded polynucleotides comprises sequences regions complementary at least in part to the sequences region (N−1) and the sequence region (N−2), and wherein the first plurality of single-stranded polynucleotides has a 3' end that is complementary to a 3' end of the first plurality of support-bound oligonucleotides;
(c) hybridizing the first plurality of single-stranded polynucleotides with the first plurality of support-bound oligonucleotides under hybridizing conditions, wherein the 3' end of the first plurality of single-stranded polynucleotides hybridize to the sequence regions (N−1) and the sequence region (N−2) of the first plurality of support-bound oligonucleotides, thereby forming partially double-stranded polynucleotides;
(d) subjecting the partially double-stranded polynucleotides to stringent wash under conditions sufficient to denature partially double-stranded polynucleotides having at least one mismatch in a complementary region without denaturing the partially double-stranded polynucleotides that do not comprise a mismatch in the complementary region, thereby releasing single-stranded polynucleotides dissociated from the error-containing partially-double stranded polynucleotides in solution;
(e) removing the single-stranded polynucleotides released in solution in step (d);
(f) generating a first plurality of complementary oligonucleotides by template-dependent synthesis under condition promoting extension of the partially double-stranded polynucleotides, thereby forming double-stranded extension products;
(g) dissociating the double-stranded extension products, thereby releasing a second plurality of polynucleotides in solution;
(h) transferring, in a predetermined order, the second plurality of polynucleotides in droplet volume form the first feature to the second feature and annealing the second plurality of polynucleotides to the second plurality of support-bound oligonucleotides; and
(i) optionally repeating the cycles of stringent wash, extension, dissociation and annealing until the target polynucleotide is synthesized.

9. The method of claim 8 wherein in step (a), the (N−1) sequence region is adjacent to the 5' end sequence region and the (N−2) sequence region is adjacent to the (N−1) sequence region.

10. The method of claim 8 wherein in step (a) each plurality of support-bound oligonucleotides comprises at least three different sequences regions (N−1), (N−2) and (N−3) between the 5' end and the 3' end sequence regions, and wherein in step (b) each plurality of single-stranded polynucleotides hybridize to the (N−1), (N−2) and (N−3) sequences regions of the pluralities of support-bound oligonucleotides.

11. The method of claim 8 wherein each plurality of single-stranded polynucleotides is a product of at least two consecutive extension chain reactions using the sequences (N−2) and (N−1) as templates.

12. The method of claim 8 wherein the double-stranded extension products are subjected to a shuffling process before undergoing a next cycle of extension.

13. The method of claim 12 wherein the shuffling process comprises:
(i) denaturing the double-stranded extension products, thereby releasing single-stranded extension products in solution;
(ii) re-annealing single-stranded extension products to the support-bound oligonucleotides, thereby producing re-annealed double-stranded products;
(iii) subjecting the re-annealed double-stranded products to stringent wash under conditions sufficient to dissociate error-containing double-stranded products;
(iv) removing single-stranded extension products dissociated from the error-containing double-stranded products; and
(v) dissociating error-free double-stranded products, thereby releasing error-free single-stranded extension products in solution.

14. The method of claim 8 wherein in step (a), the 3' end sequence region of the at least first and second pluralities of support-bound oligonucleotides is a spacer sequence, and wherein the spacer sequence comprises a primer binding site.

15. The method of claim 8 wherein in step (f), each plurality of support-bound oligonucleotides is designed to serve as a template in a different chain extension reaction, thereby forming pluralities of double-stranded extension products, wherein each plurality of double-stranded extension products has a substantially identical melting temperature.

16. The method of claim 15 wherein the difference in melting temperature between the pluralities of double-stranded extension products is less than 10° C.

17. A method for producing at least one double-stranded polynucleotide having a predefined sequence, the method comprising:
(i) synthesizing a polynucleotide on a discrete feature of a support according to the method of claim 1;
(ii) providing at least a third plurality of support-bound oligonucleotides at a third feature of the support, wherein the at least third plurality of support-bound oligonucleotides has a predefined sequence that is different from the predefined sequences of the first and second pluralities of support-bound oligonucleotides, the third plurality of support-bound oligonucleotides comprising a primer binding sequence at its 3' end and a sequence region at its 5' end substantially identical to a 5' end of the polynucleotide synthesized in step (i);
(iii) annealing a primer to the third plurality of support-bound oligonucleotides at the primer binding sequence and extending the primer in a chain extension reaction to produce a third plurality of complementary oligonucleotides, and thereby generating a third double-stranded extension product;
(iv) removing the primer from the third double-stranded extension product;
(v) dissociating the third double-stranded extension product thereby releasing the third plurality of complementary oligonucleotides, wherein the third plurality of complementary oligonucleotides is complementary to the 5' end of the polynucleotide synthesized in step (i);
(vi) contacting the polynucleotide of step (i) with the third plurality of complementary oligonucleotides;
(vii) annealing the third plurality of complementary oligonucleotides to the polynucleotide-such that the annealed oligonucleotides serves as a primer for extension in a chain extension reaction, thereby producing a double-stranded polynucleotide.

18. The method of claim 17 wherein the polynucleotide comprises a 3' terminal sequence region complementary to a 5' region of a fourth plurality of support-bound oligonucleotides at a discrete fourth feature and a 5' terminal region that is not complementary to the fourth plurality of support-bound oligonucleotides.

19. The method of claim 17 wherein the primer sequence comprises at least one Uracil and wherein the primer is removed using a mixture of Uracil DNA glycosylase (UDG) and the DNA glycosylase-lyase Endonuclease VIII.

20. A method for producing at least one double-stranded polynucleotide having a predefined sequence, the method comprising
(i) synthesizing a polynucleotide at a selected discrete feature according to claim 1;
(ii) synthesizing a complementary oligonucleotide at a different discrete feature, wherein the 3' terminal region of the complementary oligonucleotide is complementary to the 5' terminal region of the polynucleotide;
(iii) transferring the complementary oligonucleotide to the selected discrete feature; and
(iv) hybridizing the complementary oligonucleotide to the polynucleotide.

21. The method of claim 8
wherein steps (b) through (d) are performed within a first droplet volume of solution at the first feature,
wherein step (e) is performed by removing the first droplet volume of solution,
wherein steps (f) and (g) are performed within a second droplet volume of solution at the first feature, thereby releasing the second plurality of single-stranded polynucleotides in the second droplet volume of solution, and
wherein step (h) comprises transferring the second droplet volume of solution to the second feature comprising the second plurality of support-bound oligonucleotides.

22. The method of claim 1 wherein the solution is an aqueous solution.

23. The method of claim 1, wherein the droplet volume is a microvolume.

24. The method of claim 5, wherein the droplet volume is a microvolume.

25. The method of claim 8, wherein the droplet volume is a microvolume.

* * * * *

SEQUENCE LISTING

```
<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
```

-continued

```
<223> OTHER INFORMATION: Oligonucleotide

<400> SEQUENCE: 1
agtcagtcag tcagtcagtc                                                    20
```